US012703849B2

(12) United States Patent
Geisler

(10) Patent No.: US 12,703,849 B2
(45) Date of Patent: Aug. 11, 2026

(54) THERAPEUTIC ENGINEERED MICROBIAL CELL SYSTEM AND METHODS FOR TREATING HYPERURICEMIA AND GOUT

(71) Applicant: UNLOCKED LABS INC., Laramie, WY (US)

(72) Inventor: Christoph Geisler, Laramie, WY (US)

(73) Assignee: Unlocked Labs, Laramie, WY (US)

( * ) Notice: Subject to any disclaimer, the term of this patent is extended or adjusted under 35 U.S.C. 154(b) by 0 days.

(21) Appl. No.: 17/792,064

(22) PCT Filed: Jan. 8, 2021

(86) PCT No.: PCT/US2021/070014

§ 371 (c)(1),
(2) Date: Jul. 11, 2022

(87) PCT Pub. No.: WO2021/142491

PCT Pub. Date: Jul. 15, 2021

(65) Prior Publication Data

US 2023/0042430 A1 Feb. 9, 2023

Related U.S. Application Data

(60) Provisional application No. 62/959,991, filed on Jan. 12, 2020.

(51) Int. Cl.

| | |
|---|---|
| ***C12N 1/21*** | (2006.01) |
| ***A61K 9/00*** | (2006.01) |
| ***A61K 38/44*** | (2006.01) |
| ***A61P 19/06*** | (2006.01) |
| ***C12N 1/145*** | (2026.01) |
| ***C12N 1/20*** | (2006.01) |
| ***C12N 9/06*** | (2006.01) |

(52) U.S. Cl.
CPC ............ *C12N 1/145* (2021.05); *A61K 9/0053* (2013.01); *A61P 19/06* (2018.01); *C12N 1/20* (2013.01); *C12N 9/0048* (2013.01); *C12Y 107/03003* (2013.01); *C12N 2510/02* (2013.01)

(58) Field of Classification Search
None
See application file for complete search history.

(56) References Cited

U.S. PATENT DOCUMENTS

| | | | | |
|---|---|---|---|---|
| 2012/0066778 A1* | 3/2012 | Kemmer | C12N 9/16 435/325 |
| 2014/0065123 A1 | 3/2014 | Zhang et al. | |
| 2018/0127776 A1* | 5/2018 | Wang | C12N 5/0636 |
| 2019/0309269 A1 | 10/2019 | Hoffman et al. | |
| 2022/0226395 A1 | 7/2022 | Falb et al. | |

FOREIGN PATENT DOCUMENTS

| | | | |
|---|---|---|---|
| CN | 101390969 A * | 3/2009 | |
| WO | 2009120707 A1 | 10/2009 | |
| WO | WO-2010133298 A1 * | 11/2010 | A61P 19/06 |
| WO | WO-2021137829 A1 * | 7/2021 | C12N 15/63 |
| WO | WO-2021173808 A1 * | 9/2021 | A61K 35/74 |

OTHER PUBLICATIONS

O'Loughlin et al., "In Vivo and in Vitro Degradation of Urea and Uric Acid by Encapsulated Genetically Modified Microorganisms", Tissue Engineering 10:1446-1455, 2004 (Year: 2004).*
Koyama et al., "Cloning, Sequence Analysis, and Expression in *Escherichia coli* of the Gene Encoding the Candida utilis Urate Oxidase (Uricase)", J. Biochem. 120:969-973, 1996 (Year: 1996).*
Liang et al., "Development of a novel uric-acid-responsive regulatory system in *Escherichia coli*", Appl. Microbiol. Biotechnol. 99: 2267-2275, 2015 (Year: 2015).*
Machine translation of CN 101390969 A, obtained from Google Patents on Sep. 19, 2023, 20 pages (Year: 2023).*
Gencer, G., Engineering Probiotic and Commensal Bacteria for Detection and Elimination of Disease Biomarkers Through Human Gastrointestinal Tract, Dissertation, Cornell University, Aug. 2019 (Year: 2019).*
Sarayli, S., "Developing Synthetic Biology Enabled Whole Cell Biosensors," Thesis, Bilkent University, Dec. 2017 (Year: 2017).*
Gu et al., "A rapid and reliable strategy for chromosomal integration of gene(s) with multiple copies," Scientific Reports 5:9684, 2014, 9 pages (Year: 2014).*
Stoffer-Bittner et al., FEBS Open Bio 8:1322-1331, 2018 (Year: 2018).*
Coussa et al., "Oral Microencapsulated Live*Saccharomyces cerevisiae* Cells forUse in Renal Failure Uremia: Preparation and In Vivo Analysis," J. Biomed. Biotechnol. 2010:620827, 2010, 7 pages (Year: 2010).*
Leung et al., "Expression and purification of a functional uric acid-xanthine transporter (UapA)," Protein Expr. Purif. 72:139-146, 2010 (Year: 2010).*
Baghban et al., "Yeast Expression Systems: Overview and Recent Advances," Mol. Biotechnol. 61:365-384, 2019 (Year: 2019).*
Su et al., "Microbial biosensors: A review," Biosens. Bioelectron. 26:1788-1799, 2011 (Year: 2011).*
Cheng et al., Intern. Med. 2:4, 2012, 4 pages (Year: 2012).*
Bentley et al., Biotech. Bioengineer. 35:668-681, 1990 (Year: 1990).*

(Continued)

*Primary Examiner* — David Steadman
(74) *Attorney, Agent, or Firm* — Patent Law Works LLP

(57) ABSTRACT

The present disclosure relates to engineered microbial cells that have been engineered to include a uricase, a uric acid transporter, or both a uricase and a uric acid transporter. The engineered microbial cells of the present disclosure are useful in degrading uric acid inside the engineered microbial cell. The engineered microbial cells of the present disclosure are useful in methods of treating hyperuricemia. The engineered microbial cells of the present disclosure are also useful in methods of treating gout, and in particular chronic refractory gout.

15 Claims, 2 Drawing Sheets

Specification includes a Sequence Listing.

(56) References Cited

OTHER PUBLICATIONS

"Uric Acid Degradation in Man." Nutrition Reviews 18, Feb. 1960, vol. 18, No. 2, pp. 42-45.
Benn, Caroline L et al. "Physiology of Hyperuricemia and Urate-Lowering Treatments." Frontiers in Medicine (2018) vol. 5, pp. 160-160.
Ganson, Nancy J et al. "Control of Hyperuricemia in Subjects with Refractory Gout and Induction of Antibody against Poly(Ethylene Glycol) (Peg) in a Phase I Trial of Subcutaneous Pegylated Urate Oxidase." Arthritis Research Therapy, vol. 8 (2005) pp. 1-10. https://doi.org/10.1186/ar1861.
Gliozzi, Micaela et al. "The Treatment of Hyperuricemia." International Journal of Cardiology (2016) 213, pp. 23-27. https://doi.org/10.1016/j.ijcard.2015.08.087.
Guttmann, Allison et al. "Pegloticase in Gout Treatment—Safety Issues Latest Evidence and Clinical Considerations." Therapeutic Advances in Drug Safety (2017) vol. 8, No. 12, pp. 379-388.
Hosomi, Atsushi et al. "Extra-Renal Elimination of Uric Acid Via Intestinal Efflux Transporter Bcrp/abcg2." Plos One (2012) 7(2) pp. e30456-e30456.
Huang, Su-Hua and Tung-Kung Wu. "Modified Colorimetric Assay for Uricase Activity and a Screen for Mutant Bacillus Subtilis Uricase Genes Following Step Mutagenesis." European Journal of Biochemistry (2004) vol. 271, pp. 517-523.
Kelley, William N and Weiner Irwin M. Uric Acid. Berlin Heidelberg: Springer Berlin Heidelberg; Handbook of Experimental Pharmacology, 51, 1978.
Krypotou, Emilia and George Diallinas. "Transport Assays in Filamentous Fungi: Kinetic Characterization of the Uapc Purine Transporter of Aspergillus Nidulans." Fungal Genetics and Biology : Fg B (2014) vol. 63, pp. 1-8.
Leach M et al. "Efficacy of Urate Oxidase (Uricozyme) in Tumour Lysis Induced Urate Nephropathy." Clinical Laboratory Haematology (1998) vol. 20, pp. 169-172.
Nishida, Y et al. "Hypouricaemic Effect After Oral Administration in Chickens of Polyethylene Glycol-Modified Uricase Entrapped in Liposomes." The Journal of Pharmacy and Pharmacology (1984) 36, 198405, pp. 354-355.
Seegmiller, J E et al. "Uric acid production in gout." The Journal of clinical investigation vol. 40,7 (1961): 1304-14. doi:10.1172/JCI104360.
Sherman, Merry R et al. "Peg-Uricase in the Management of Treatment-Resistant Gout and Hyperuricemia." Advanced Drug Delivery Reviews (2008) vol. 60, pp. 59-68.
Sorensen, Leif B and Dennis J Levinson. "Origin and Extrarenal Elimination of Uric Acid in Man." Nephron (1975) vol. 14: pp. 7-20.
Sorensen, Leif B. "Role of the Intestinal Tract in the Elimination of Uric Acid." Arthritis Rheumatism 1965: vol. 8, pp. 694-706. https://doi.org/10.1002/art.1780080429.
Suzuki, Koji et al. "Molecular Cloning and Expression of Uricase Gene from Arthrobacter Globiformis in *Escherichia coli* and Characterization of the Gene Product." Journal of Bioscience and Bioengineering (2004) vol. 98, No. 3, pp. 153-158.
Szczurek, Paulina et al. "Oral Uricase Eliminates Blood Uric Acid in the Hyperuricemic Pig Model." Plos One (2017), 12(6): pp. e0179195-e0179195. https://doi.org/10.1371/journal.pone.0179195.
Tan, Philip K et al. "Mechanism of High Affinity Inhibition of the Human Urate Transporter Urat1." Scientific Reports (2016) 6, pp. 34995-34995.
Terkeltaub, Robert. "Update on Gout: New Therapeutic Strategies and Options." Nature Reviews. Rheumatology (2010) vol. 6, pp. 30-38. https://doi.org/10.1038/nrrheum.2009.236.
Ueng, Sis. "Rasburicase (Elitek): A Novel Agent for Tumor Lysis Syndrome." Proceedings (Baylor University. Medical Center Proceedings) 2005: 18, pp. 275-279.
Xu, Xianxiang et al. "Uric Acid Transporters Hiding in the Intestine." Pharmaceutical Biology (2016) vol. 54, No. 12, pp. 3151-3155.
Nyborg, Andrew C., et al., "A Therapeutic Uricase with Reduced Immunogenicity Risk and Improved Development Properties." PLOS ONE, Dec. 21, 2016; vol. 11, Nr:12, pp. 0167935, https://www.ncbi.nlm.nih.gov/pmc/articles/PMC5176304/pdf/pone.0167935.pdf.
Papakostas, Konstantinos, et al., "Substrate Selectivity of YgfU, a Uric Acid Transporter from *Escherichia coli*." Journal of Biological Chemistry, American Society for Biochemistry and Molecular Biology, (May 4, 2012) vol. 287, No. 19, pp. 15684-15695.
PCT International Search Report and Written Opinion; Application No. PCT/US21/70014 Therapeutics, LLC, International filing date of Jan. 8, 2021, date of mailing Oct. 29, 2021, 13 pages.
O'Loughlin, Jill A., et al. "Oral Administration of Biochemically Active Microcapsules to Treat Uremia: New Insights into an Old Approach." Journal of Biomaterials Science. Polymer Ed., vol. 15, No. 11, 2004, pp. 1447-1461.

* cited by examiner

SEQUENCE LISTING

```
<160> NUMBER OF SEQ ID NOS: 26

<210> SEQ ID NO 1
<211> LENGTH: 313
<212> TYPE: PRT
<213> ORGANISM: Candida utilis

<400> SEQUENCE: 1

Met Ser Thr Thr Leu Ser Ser Ser Thr Tyr Gly Lys Asp Asn Val Lys
1               5                   10                  15

Phe Leu Lys Val Lys Lys Asp Pro Gln Asn Pro Lys Lys Gln Glu Val
            20                  25                  30

Met Glu Ala Thr Val Thr Cys Leu Leu Glu Gly Gly Phe Asp Thr Ser
        35                  40                  45

Tyr Thr Glu Ala Asp Asn Ser Ser Ile Val Pro Thr Asp Thr Val Lys
    50                  55                  60

Asn Thr Ile Leu Val Leu Ala Lys Thr Thr Glu Ile Trp Pro Ile Glu
65                  70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
            100                 105                 110

Ala Val Asp Gly Lys Pro His Asp His Ser Phe Ile His Glu Gly Gly
        115                 120                 125

Glu Lys Arg Ile Thr Asp Leu Tyr Tyr Lys Arg Ser Gly Asp Tyr Lys
    130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
                165                 170                 175

Thr Asp Arg Ile Leu Ser Thr Asp Val Asp Ala Thr Trp Val Trp Asp
            180                 185                 190

Asn Lys Lys Ile Gly Thr Val Tyr Asp Ile Ala Lys Ala Ala Asp Lys
        195                 200                 205

Gly Ile Phe Asp Asn Val Tyr Asn Gln Ala Arg Glu Ile Thr Leu Thr
    210                 215                 220

Thr Phe Ala Leu Glu Asn Ser Pro Ser Val Gln Ala Thr Met Phe Asn
225                 230                 235                 240

Met Ala Thr Gln Ile Leu Glu Lys Ala Cys Ser Val Tyr Ser Val Ser
```

```
                245                 250                 255

Tyr Ala Leu Pro Asn Lys His Tyr Phe Leu Ile Asp Leu Lys Trp Lys
            260                 265                 270

His Tyr Phe Leu Ile Asp Leu Lys Trp Lys Gly Leu Glu Asn Asp Asn
        275                 280                 285

Glu Leu Phe Tyr Pro Ser Pro His Pro Asn Gly Leu Ile Lys Cys Thr
    290                 295                 300

Val Val Arg Lys Glu Lys Thr Lys Leu
305                 310


<210> SEQ ID NO 2
<211> LENGTH: 302
<212> TYPE: PRT
<213> ORGANISM: Unknown
<220> FEATURE:
<223> OTHER INFORMATION: Aspergillus flavus

<400> SEQUENCE: 2

Met Ser Ala Val Lys Ala Ala Arg Tyr Gly Lys Asp Asn Val Arg Val
1               5                   10                  15

Tyr Lys Val His Lys Asp Glu Lys Thr Gly Val Gln Thr Val Tyr Glu
            20                  25                  30

Met Thr Val Cys Val Leu Leu Glu Gly Glu Ile Glu Thr Ser Tyr Thr
        35                  40                  45

Lys Ala Asp Asn Ser Val Ile Val Ala Thr Asp Ser Ile Lys Asn Thr
    50                  55                  60

Ile Tyr Ile Thr Ala Lys Gln Asn Pro Val Thr Pro Pro Glu Leu Phe
65                  70                  75                  80

Gly Ser Ile Leu Gly Thr His Phe Ile Glu Lys Tyr Asn His Ile His
                85                  90                  95

Ala Ala His Val Asn Ile Val Cys His Arg Trp Thr Arg Met Asp Ile
            100                 105                 110

Asp Gly Lys Pro His Pro His Ser Phe Ile Arg Asp Ser Glu Glu Lys
        115                 120                 125

Arg Asn Val Gln Val Asp Val Val Glu Gly Lys Gly Ile Asp Ile Lys
    130                 135                 140

Ser Ser Leu Ser Gly Leu Thr Val Leu Lys Ser Thr Asn Ser Gln Phe
145                 150                 155                 160

Trp Gly Phe Leu Arg Asp Glu Tyr Thr Thr Leu Lys Glu Thr Trp Asp
                165                 170                 175

Arg Ile Leu Ser Thr Asp Val Asp Ala Thr Trp Gln Trp Lys Asn Phe
            180                 185                 190

Ser Gly Leu Gln Glu Val Arg Ser His Val Pro Lys Phe Asp Ala Thr
        195                 200                 205

Trp Ala Thr Ala Arg Glu Val Thr Leu Lys Thr Phe Ala Glu Asp Asn
    210                 215                 220

Ser Ala Ser Val Gln Ala Thr Met Tyr Lys Met Ala Glu Gln Ile Leu
225                 230                 235                 240

Ala Arg Gln Gln Leu Ile Glu Thr Val Glu Tyr Ser Leu Pro Asn Lys
                245                 250                 255

His Tyr Phe Glu Ile Asp Leu Ser Trp His Lys Gly Leu Gln Asn Thr
            260                 265                 270

Gly Lys Asn Ala Glu Val Phe Ala Pro Gln Ser Asp Pro Asn Gly Leu
        275                 280                 285

Ile Lys Cys Thr Val Gly Arg Ser Ser Leu Lys Ser Lys Leu
```

```
    290                 295                 300


<210> SEQ ID NO 3
<211> LENGTH: 302
<212> TYPE: PRT
<213> ORGANISM: Arthrobacter globiformis

<400> SEQUENCE: 3

Met Thr Ala Thr Ala Glu Thr Ser Thr Gly Thr Lys Val Val Leu Gly
1               5                   10                  15

Gln Asn Gln Tyr Gly Lys Ala Glu Val Arg Leu Val Lys Val Thr Arg
            20                  25                  30

Asn Thr Ala Arg His Glu Ile Gln Asp Leu Asn Val Thr Ser Gln Leu
        35                  40                  45

Arg Gly Asp Phe Glu Ala Ala His Thr Ala Gly Asp Asn Ala His Val
    50                  55                  60

Val Ala Thr Asp Thr Gln Lys Asn Thr Val Tyr Ala Phe Ala Arg Asp
65                  70                  75                  80

Gly Phe Ala Thr Thr Glu Glu Phe Leu Leu Arg Leu Gly Lys His Phe
                85                  90                  95

Thr Glu Gly Phe Asp Trp Val Thr Gly Gly Arg Trp Ala Ala Gln Gln
            100                 105                 110

Phe Phe Trp Asp Arg Ile Asn Asp His Asp His Ala Phe Ser Arg Asn
        115                 120                 125

Lys Ser Glu Val Arg Thr Ala Val Leu Glu Ile Ser Gly Ser Glu Gln
    130                 135                 140

Ala Ile Val Ala Gly Ile Glu Gly Leu Thr Val Leu Lys Ser Thr Gly
145                 150                 155                 160

Ser Glu Phe His Gly Phe Pro Arg Asp Lys Tyr Thr Thr Leu Gln Glu
                165                 170                 175

Thr Thr Asp Arg Ile Leu Ala Thr Asp Val Ser Ala Arg Trp Arg Tyr
            180                 185                 190

Asn Thr Val Glu Val Asp Phe Asp Ala Val Tyr Ala Ser Val Arg Gly
        195                 200                 205

Leu Leu Leu Lys Ala Phe Ala Glu Thr His Ser Leu Ala Leu Gln Gln
    210                 215                 220

Thr Met Tyr Glu Met Gly Arg Ala Val Ile Glu Thr His Pro Glu Ile
225                 230                 235                 240

Asp Glu Ile Lys Met Ser Leu Pro Asn Lys His His Phe Leu Val Asp
                245                 250                 255

Leu Gln Pro Phe Gly Gln Asp Asn Pro Asn Glu Val Phe Tyr Ala Ala
            260                 265                 270

Asp Arg Pro Tyr Gly Leu Ile Glu Ala Thr Ile Gln Arg Glu Gly Ser
        275                 280                 285

Arg Ala Asp His Pro Ile Trp Ser Asn Ile Ala Gly Phe Cys
    290                 295                 300


<210> SEQ ID NO 4
<211> LENGTH: 304
<212> TYPE: PRT
<213> ORGANISM: Artificial Sequence
<220> FEATURE:
<223> OTHER INFORMATION: synthetic construct / Chimeric porcine / baboon

<400> SEQUENCE: 4

Met Ala His Tyr Arg Asn Asp Tyr Lys Lys Asn Asp Glu Val Glu Phe
1               5                   10                  15
```

```
Val Arg Thr Gly Tyr Gly Lys Asp Met Ile Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Leu His Gly Asp Asn Ser Asp
    50                  55                  60

Val Ile Pro Thr Asp Thr Ile Lys Asn Thr Val Asn Val Leu Ala Lys
65                  70                  75                  80

Phe Lys Gly Ile Lys Ser Ile Glu Thr Phe Ala Val Thr Ile Cys Glu
                85                  90                  95

His Phe Leu Ser Ser Phe Lys His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile Tyr Thr Pro Thr Gly Thr His Phe Cys Glu Val Glu
    130                 135                 140

Gln Ile Arg Asn Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Gln
            180                 185                 190

Val Tyr Cys Lys Trp Arg Tyr His Gln Gly Arg Asp Val Asp Phe Glu
        195                 200                 205

Ala Thr Trp Asp Thr Val Arg Ser Ile Val Leu Gln Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Glu Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300


<210> SEQ ID NO 5
<211> LENGTH: 296
<212> TYPE: PRT
<213> ORGANISM: Schizosaccharomyces pombe

<400> SEQUENCE: 5

Met Ser Glu Thr Thr Tyr Val Lys Gln Cys Ala Tyr Gly Lys Thr Leu
1               5                   10                  15

Val Arg Phe Met Lys Lys Asp Ile Cys Pro Lys Thr Lys Thr His Thr
            20                  25                  30

Val Tyr Glu Met Asp Val Gln Ser Leu Leu Thr Gly Glu Leu Glu Glu
        35                  40                  45

Ser Tyr Thr Lys Ala Asp Asn Ser Ile Val Val Pro Thr Asp Thr Gln
    50                  55                  60

Lys Asn Thr Ile Tyr Val Phe Ala Lys Asn Asn Asp Val Ser Val Pro
65                  70                  75                  80

Glu Val Phe Ala Ala Lys Leu Ala Lys His Phe Val Asp Lys Tyr Lys
```

```
                85                  90                  95

His Ile His Gly Ala Ala Leu Asp Ile Thr Ile Thr Pro Trp Thr Arg
            100                 105                 110

Met Glu Val Gln Gly Lys Pro His Ser His Ser Phe Ile Arg Asn Pro
        115                 120                 125

Gly Glu Thr Arg Lys Thr His Val Val Phe Ser Glu Gly Lys Gly Phe
    130                 135                 140

Asp Val Val Ser Ser Leu Lys Asp Val Leu Val Leu Lys Ser Thr Gly
145                 150                 155                 160

Ser Gly Phe Thr Asn Phe His Lys Cys Glu Phe Thr Thr Leu Pro Glu
                165                 170                 175

Val Thr Asp Arg Ile Phe Ser Thr Ser Ile Asp Cys Asn Tyr Thr Phe
            180                 185                 190

Lys His Phe Asp Thr Phe Glu Glu Leu Ala Gly Phe Asp Phe Asn Ser
        195                 200                 205

Ile Tyr Glu Lys Val Lys Glu Ile Thr Leu Glu Thr Phe Ala Leu Asp
    210                 215                 220

Asp Ser Glu Ser Val Gln Ala Thr Met Tyr Lys Met Ala Asp Thr Ile
225                 230                 235                 240

Ile Asn Thr Tyr Pro Ala Ile Asn Glu Val Tyr Tyr Ala Leu Pro Asn
                245                 250                 255

Lys His Tyr Phe Glu Ile Asn Leu Ala Pro Phe Asn Ile Asp Asn Leu
            260                 265                 270

Gly Ser Asn Cys Ser Leu Tyr Gln Pro Gln Ala Tyr Pro Ser Gly Tyr
        275                 280                 285

Ile Thr Cys Thr Val Ala Arg Lys
    290                 295


<210> SEQ ID NO 6
<211> LENGTH: 494
<212> TYPE: PRT
<213> ORGANISM: Bacillus subtilis

<400> SEQUENCE: 6

Met Phe Thr Met Asp Asp Leu Asn Gln Met Asp Thr Gln Thr Leu Thr
1               5                   10                  15

Asp Thr Leu Gly Ser Ile Phe Glu His Ser Ser Trp Ile Ala Glu Arg
            20                  25                  30

Ser Ala Ala Leu Arg Pro Phe Ser Ser Leu Ser Asp Leu His Arg Lys
        35                  40                  45

Met Thr Gly Ile Val Lys Ala Ala Asp Arg Glu Thr Gln Leu Asp Leu
    50                  55                  60

Ile Lys Lys His Pro Arg Leu Gly Thr Lys Lys Thr Met Ser Gly Asp
65                  70                  75                  80

Ser Val Arg Glu Gln Gln Asn Ala Gly Leu Ser Lys Leu Glu Gln Gln
                85                  90                  95

Glu Tyr Glu Glu Phe Leu Met Leu Asn Glu His Tyr Tyr Asp Arg Phe
            100                 105                 110

Gly Phe Pro Phe Ile Leu Ala Val Lys Gly Lys Thr Lys Gln Asp Ile
        115                 120                 125

His Gln Ala Leu Leu Ala Arg Leu Glu Ser Glu Arg Glu Thr Glu Phe
    130                 135                 140

Gln Gln Ala Leu Ile Glu Ile Tyr Arg Ile Ala Arg Phe Arg Leu Ala
145                 150                 155                 160
```

```
Asp Ile Ile Thr Glu Lys Gly Glu Thr Gln Met Lys Arg Thr Met Ser
                165                 170                 175

Tyr Gly Lys Gly Asn Val Phe Ala Tyr Arg Thr Phe Leu Lys Pro Leu
            180                 185                 190

Thr Gly Val Lys Gln Ile Pro Glu Ser Ser Phe Ala Gly Arg Ser Asn
        195                 200                 205

Thr Val Val Gly Val Asp Val Thr Cys Glu Ile Gly Gly Glu Ala Phe
    210                 215                 220

Leu Pro Ser Phe Thr Asp Gly Asp Asn Thr Leu Val Val Ala Thr Asp
225                 230                 235                 240

Ser Met Lys Asn Phe Ile Gln Arg His Leu Ala Ser Tyr Glu Gly Thr
                245                 250                 255

Thr Thr Glu Gly Phe Leu His Tyr Val Ala His Arg Phe Leu Asp Thr
            260                 265                 270

Tyr Ser His Met Asp Lys Ile Thr Leu Thr Gly Glu Asp Ile Pro Phe
        275                 280                 285

Glu Ala Met Pro Ala Tyr Glu Glu Lys Glu Leu Ser Thr Ser Arg Leu
    290                 295                 300

Val Phe Arg Arg Ser Arg Asn Glu Arg Ser Arg Ser Val Leu Lys Ala
305                 310                 315                 320

Glu Arg Ser Gly Asn Thr Ile Thr Ile Thr Glu Gln Tyr Ser Glu Ile
                325                 330                 335

Met Asp Leu Gln Leu Val Lys Val Ser Gly Asn Ser Phe Val Gly Phe
            340                 345                 350

Ile Arg Asp Glu Tyr Thr Thr Leu Pro Glu Asp Gly Asn Arg Pro Leu
        355                 360                 365

Phe Val Tyr Leu Asn Ile Ser Trp Gln Tyr Glu Asn Thr Asn Asp Ala
    370                 375                 380

Tyr Ala Phe Asp Pro Ser Arg Tyr Val Ala Ala Glu Gln Val Arg Asp
385                 390                 395                 400

Leu Ala Ser Thr Val Phe His Glu Leu Glu Thr Pro Ser Ile Gln Asn
                405                 410                 415

Leu Ile Tyr His Ile Gly Cys Arg Ile Leu Ala Arg Phe Pro Gln Leu
            420                 425                 430

Thr Asp Val Ser Phe Gln Ser Gln Asn His Thr Trp Asp Thr Val Val
        435                 440                 445

Glu Glu Ile Pro Gly Ser Lys Gly Lys Val Tyr Thr Glu Pro Arg Pro
    450                 455                 460

Pro Tyr Gly Phe Gln His Phe Thr Val Thr Arg Glu Asp Ala Glu Lys
465                 470                 475                 480

Glu Lys Gln Lys Thr Ala Glu Lys Cys Arg Ser Leu Lys Ala
                485                 490
```

<210> SEQ ID NO 7
<211> LENGTH: 305
<212> TYPE: PRT
<213> ORGANISM: Unknown
<220> FEATURE:
<223> OTHER INFORMATION: Zygosaccharomyces parabailii

<400> SEQUENCE: 7

```
Met Ser Tyr Leu Ala Asp Ser Thr Tyr Gly Lys Asp Asn Val Lys Phe
1               5                   10                  15

Leu Lys Val Lys Lys Asp Pro Ser Asn Pro Lys Leu Gln Gln Val Met
            20                  25                  30
```

```
Glu Ala Thr Val Lys Val Leu Leu Arg Gly Asn Phe Asp Val Ser Tyr
        35                  40                  45

Thr Glu Ala Asp Asn Ser Pro Ile Val Pro Thr Asp Thr Val Lys Asn
    50                  55                  60

Thr Ile Leu Ile Leu Ala Arg Gln Asn Asp Thr Trp Pro Thr Glu Lys
65                  70                  75                  80

Phe Ala Ala Lys Leu Ala Leu His Phe Thr Gly Lys Tyr Ser His Val
                85                  90                  95

Ser Gly Val Ser Ile Lys Ile Tyr Gln Glu Arg Trp Val Lys Tyr Asp
            100                 105                 110

Val Asp Gly Arg Pro Ser Gln His Ser Phe Val His Gln Gly Pro Glu
        115                 120                 125

Lys Lys Ile Val Glu Leu Glu Tyr Asp Lys Val Asn Gly Pro Thr His
    130                 135                 140

Tyr Lys Leu Ser Thr Ser Ile Lys Asp Leu Thr Val Leu Lys Ser Thr
145                 150                 155                 160

Asn Ser Met Phe Tyr Asp Tyr Asn Val Cys Glu Tyr Thr Thr Leu Lys
                165                 170                 175

Pro Thr Thr Asp Arg Val Leu Ser Thr Asp Ile Phe Ala Val Trp Asp
            180                 185                 190

Trp Ser Ala Ser Lys Leu Gly Pro Leu Thr Ala Ile Ala Ala Gly Ala
        195                 200                 205

Ser Asp Leu Val Phe Asp Lys Val Phe Asn Asp Ala Arg Asp Ile Thr
    210                 215                 220

Leu Asp Ile Phe Ala Lys Glu Asn Ser Val Ser Val Gln Ala Thr Met
225                 230                 235                 240

Tyr Asn Met Gly Val Ala Ile Leu Ala Lys Ala Pro Gln Val Glu Tyr
                245                 250                 255

Val Ser Tyr Glu Leu Pro Asn Lys His Tyr Ile Leu Phe Asp Leu Lys
            260                 265                 270

Trp Phe Gln Gly Leu Ser Asn Asp Asn Glu Leu Phe Tyr Pro Ser Pro
        275                 280                 285

His Pro Asn Gly Leu Ile Arg Cys Lys Val Gly Arg Lys Thr Ser Lys
    290                 295                 300

Leu
305


<210> SEQ ID NO 8
<211> LENGTH: 281
<212> TYPE: PRT
<213> ORGANISM: Unknown
<220> FEATURE:
<223> OTHER INFORMATION: Spirosoma sp. KCTC 42546

<400> SEQUENCE: 8

Met Lys Leu Thr Leu Lys Lys Asn Ala Tyr Gly Lys Asn Ala Val Asn
1               5                   10                  15

Leu Ser Lys Ile Ile Arg His Pro Asn Tyr His Glu Phe Arg Gln Ile
            20                  25                  30

Ser Val Asn Val Ser Leu Glu Gly Asp Phe Glu Thr Ala His Thr Leu
        35                  40                  45

Gly Asp Asn Ser Lys Ile Val Pro Thr Asp Thr Gln Lys Asn Thr Val
    50                  55                  60

Tyr Ala Leu Ala Lys Glu His Phe Val Asp Ser Ile Glu Asn Phe Gly
65                  70                  75                  80
```

```
Leu Tyr Leu Ala Asn Tyr Phe Ile Thr Asn Asn Pro Gln Val Ser Gln
                85                  90                  95

Ala Thr Val His Ile Ile Glu His Pro Trp Ala Arg Met Ala Phe Asp
            100                 105                 110

Gly Glu Pro His His His Ala Tyr Val Gly Gly Gly Ser Glu Lys Arg
        115                 120                 125

Thr Thr Thr Leu Val Gln Thr Thr Glu Ala Ile Arg Val Thr Ser Gly
    130                 135                 140

Ile Lys Asp Leu Leu Ile Leu Lys Thr Thr Asp Ser Gly Phe Glu Gly
145                 150                 155                 160

Tyr Val Lys Asp Gln Tyr Thr Thr Leu Lys Glu Thr Ala Asp Arg Ile
                165                 170                 175

Phe Ala Thr Gln Cys Glu Ala Asn Trp Val Tyr Thr Ser His Asn Leu
            180                 185                 190

Asp Phe Thr Ser Leu Phe Gly Lys Ile Arg Glu Thr Leu Leu Lys Thr
        195                 200                 205

Phe Ala His His Lys Ser Leu Ser Val Gln Gln Thr Leu Leu Ala Met
    210                 215                 220

Gly Ser Ala Val Leu Glu Glu Asn Gln Glu Val Ser Glu Ile Ser Leu
225                 230                 235                 240

Ile Met Pro Asn Lys His His Ile Pro Phe Asn Leu Glu Gln Phe Gly
                245                 250                 255

Met Asp Asn Gln Asn Glu Ile Phe Ile Ala Thr Asp Glu Pro Tyr Gly
            260                 265                 270

Tyr Ile Thr Gly Thr Val Thr Arg Glu
        275                 280


<210> SEQ ID NO 9
<211> LENGTH: 574
<212> TYPE: PRT
<213> ORGANISM: Unknown
<220> FEATURE:
<223> OTHER INFORMATION: Aspergillus nidulans

<400> SEQUENCE: 9

Met Asp Asn Ser Ile His Ser Thr Asp Gly Pro Asp Ser Val Ile Pro
1               5                   10                  15

Asn Ser Asn Pro Lys Lys Thr Val Arg Gln Arg Val Arg Leu Leu Ala
            20                  25                  30

Arg His Leu Thr Thr Arg Glu Gly Leu Ile Gly Asp Tyr Asp Tyr Gly
        35                  40                  45

Phe Leu Phe Arg Pro Glu Leu Pro Phe Met Lys Lys Asp Pro Arg Ala
    50                  55                  60

Pro Pro Phe Phe Gly Leu Asn Glu Lys Ile Pro Val Leu Leu Ala Phe
65                  70                  75                  80

Ile Leu Gly Leu Gln His Ala Leu Ala Met Leu Ala Gly Val Val Thr
                85                  90                  95

Pro Pro Leu Ile Ile Ser Ser Ser Leu Ser Leu Pro Ser Asp Leu Gln
            100                 105                 110

Gln Tyr Leu Val Ser Thr Ser Leu Ile Val Cys Gly Leu Leu Ser Met
        115                 120                 125

Val Gln Ile Thr Arg Phe His Ile Tyr Lys Thr Pro Tyr Tyr Ile Gly
    130                 135                 140

Ser Gly Val Leu Ser Val Met Gly Val Ser Phe Ser Ile Ile Ser Val
145                 150                 155                 160
```

```
Ala Ser Gly Ala Phe Asn Gln Met Tyr Ser Asn Gly Phe Cys Gln Leu
                165                 170                 175

Asp Glu Ala Gly Asn Arg Leu Pro Cys Pro Glu Ala Tyr Gly Ala Leu
            180                 185                 190

Ile Gly Thr Ser Ala Cys Cys Ala Leu Val Glu Ile Leu Leu Ala Phe
        195                 200                 205

Val Pro Pro Lys Val Ile Gln Lys Ile Phe Pro Pro Ile Val Thr Gly
    210                 215                 220

Pro Thr Val Met Leu Ile Gly Ile Ser Leu Ile Gly Thr Gly Phe Lys
225                 230                 235                 240

Asp Trp Ala Gly Gly Ser Ala Cys Met Asp Asp Gly Met Leu Cys Pro
                245                 250                 255

Ser Ala Thr Ala Pro Arg Pro Leu Pro Trp Gly Ser Pro Glu Phe Ile
            260                 265                 270

Gly Leu Gly Phe Leu Val Phe Val Ser Ile Ile Leu Cys Glu Arg Phe
        275                 280                 285

Gly Ala Pro Ile Met Lys Ser Cys Ser Val Val Ile Gly Leu Leu Val
    290                 295                 300

Gly Cys Ile Val Ala Ala Ala Cys Gly Tyr Phe Ser His Ala Asp Ile
305                 310                 315                 320

Asp Ala Ala Pro Ala Ala Ser Phe Ile Trp Val Lys Thr Phe Pro Leu
                325                 330                 335

Ser Val Tyr Gly Pro Met Val Leu Pro Ile Ile Ala Val Phe Ile Ile
            340                 345                 350

Cys Ala Cys Glu Cys Ile Gly Asp Val Thr Ala Thr Cys Asp Val Ser
        355                 360                 365

Arg Leu Glu Val Arg Gly Gly Thr Phe Glu Ser Arg Ile Gln Gly Ala
    370                 375                 380

Val Leu Ala Asp Gly Ile Asn Ser Val Val Ala Ala Leu Ala Thr Met
385                 390                 395                 400

Thr Pro Met Thr Thr Phe Ala Gln Asn Asn Gly Val Ile Ala Leu Thr
                405                 410                 415

Arg Cys Ala Asn Arg Trp Ala Gly Tyr Cys Cys Cys Leu Ile Leu Ile
            420                 425                 430

Val Ala Gly Ile Phe Ala Lys Phe Ala Ala Ala Ile Val Ala Ile Pro
        435                 440                 445

Asn Ser Val Met Gly Gly Met Lys Thr Phe Leu Phe Ala Ser Val Val
    450                 455                 460

Ile Ser Gly Gln Ala Ile Val Ala Lys Ala Pro Phe Thr Arg Arg Asn
465                 470                 475                 480

Arg Phe Ile Leu Thr Ala Ser Met Ala Leu Gly Tyr Gly Ala Thr Leu
                485                 490                 495

Val Pro Thr Trp Phe Gly Asn Val Phe Pro Gln Thr Glu Asn Arg Asp
            500                 505                 510

Leu Glu Gly Phe Glu Asn Ala Ile Glu Leu Val Leu Glu Thr Gly Phe
        515                 520                 525

Ala Val Thr Ala Phe Val Ala Met Leu Leu Asn Ala Ile Met Pro Ala
    530                 535                 540

Glu Val Glu Glu Ile Gly Ala Val Thr Pro Met Pro Val Ser Ala His
545                 550                 555                 560

Asp Asn Arg Asp Gly Glu Ala Glu Tyr Gln Ser Lys Gln Ala
                565                 570
```

<210> SEQ ID NO 10
<211> LENGTH: 580
<212> TYPE: PRT
<213> ORGANISM: Unknown
<220> FEATURE:
<223> OTHER INFORMATION: Aspergillus nidulans

<400> SEQUENCE: 10

```
Met Asp Gly Pro Asp Gln Ile Gly Pro Asp Val Arg Pro Arg Arg Thr
1               5                   10                  15

Phe Gly Asp Arg Val Arg Arg Ala Ala Arg Ala Phe Thr Thr Arg Asp
            20                  25                  30

Gly Leu Ile Gly Asp Tyr Asp Tyr Gly Phe Leu Phe Thr Pro Arg Leu
        35                  40                  45

Pro Phe Val Lys Gln Lys Arg Arg Ala Ala Pro Phe Phe Gly Leu Glu
    50                  55                  60

Asp Lys Ile Pro Leu Val Leu Ala Leu Leu Leu Gly Leu Gln His Ala
65                  70                  75                  80

Leu Ala Met Leu Ala Gly Val Ile Thr Pro Pro Ile Leu Leu Ala Gly
                85                  90                  95

Ser Ser Gly Ala Asn Phe Gly Ala Asp Glu Ser Gln Tyr Leu Val Ser
            100                 105                 110

Thr Ser Leu Ile Val Ser Gly Leu Leu Ser Ala Val Gln Met Phe Arg
        115                 120                 125

Leu His Val Tyr Lys Thr Arg Tyr Tyr Val Gly Thr Gly Leu Val Ser
    130                 135                 140

Val Val Gly Thr Ser Phe Ala Thr Ile Thr Val Ala Thr Gly Thr Phe
145                 150                 155                 160

Asn Gln Met Tyr Ser Thr Gly Tyr Cys Pro Val Asp Gly Ser Gly Asn
                165                 170                 175

Arg Leu Pro Cys Pro Lys Gly Tyr Gly Ala Leu Leu Ala Thr Ser Cys
            180                 185                 190

Leu Cys Ser Leu Leu Glu Ile Gly Leu Ser Phe Met Ser Ser Arg Leu
        195                 200                 205

Leu Lys Ala Leu Phe Pro Pro Ile Val Thr Gly Pro Thr Val Phe Leu
    210                 215                 220

Ile Gly Ala Ser Leu Ile Gly Asn Ala Met Lys Asp Trp Ala Gly Gly
225                 230                 235                 240

Ser Gly Thr Cys Ser Ser Asn Pro Gly Asn Gly Ala Leu Cys Pro Ser
                245                 250                 255

Ala Asp Ala Pro His Pro Leu Pro Trp Gly Ser Ala Glu Phe Ile Gly
            260                 265                 270

Leu Gly Phe Leu Val Phe Ala Thr Ile Ile Leu Cys Glu Arg Phe Gly
        275                 280                 285

Ser Pro Ile Met Lys Ser Cys Ala Val Ile Val Gly Leu Leu Val Gly
    290                 295                 300

Cys Ile Val Ala Ala Ala Cys Gly Tyr Phe Asp Arg Ser Gly Ile Asp
305                 310                 315                 320

Ala Ala Pro Val Ala Ser Phe Ile Trp Val Lys Thr Phe Pro Leu Thr
                325                 330                 335

Ile Tyr Ala Pro Leu Ile Leu Pro Leu Leu Ala Val Tyr Met Val Ile
            340                 345                 350

Met Met Glu Ser Ile Gly Asp Ile Thr Ala Thr Cys Asp Val Ser Arg
        355                 360                 365

Leu Gln Val Glu Gly Ala Thr Phe Asp Ser Arg Ile Gln Gly Gly Val
```

```
    370                 375                 380

Leu Gly Asn Gly Ile Thr Cys Leu Leu Ala Gly Leu Cys Thr Ile Thr
385                 390                 395                 400

Pro Met Ser Val Phe Ala Gln Asn Asn Gly Val Ile Ala Leu Thr Arg
                405                 410                 415

Cys Ala Asn Arg Lys Ala Gly Tyr Cys Cys Cys Phe Phe Leu Val Val
            420                 425                 430

Met Gly Ile Phe Ala Lys Phe Ala Ala Ala Leu Val Ala Ile Pro Ser
        435                 440                 445

Ser Val Leu Gly Gly Met Thr Thr Phe Leu Phe Ser Ser Val Ala Ile
    450                 455                 460

Ser Gly Val Arg Ile Met Cys Ser Val Asp Trp Thr Arg Arg Asn Arg
465                 470                 475                 480

Phe Ile Leu Thr Ala Ser Phe Ala Val Gly Met Ala Ala Thr Leu Val
                485                 490                 495

Pro Asp Trp Phe Ser Tyr Phe Phe Thr Tyr Ser Gly Asp Asn His Ala
            500                 505                 510

Leu Glu Gly Leu Leu Gln Ala Val Glu Leu Val Met Ala Asn Gly Phe
        515                 520                 525

Ala Val Thr Gly Phe Leu Gly Leu Leu Leu Asn Leu Ile Leu Pro Glu
    530                 535                 540

Asp Met Glu Glu Asp Val Val Glu Ser Glu Glu Asp Tyr Glu Ala Thr
545                 550                 555                 560

Thr Val Val Gly Met Gln Gly Gly Ser Glu Pro Gly Ser Ser Gly Gln
                565                 570                 575

Asn Val Lys Ala
            580


<210> SEQ ID NO 11
<211> LENGTH: 583
<212> TYPE: PRT
<213> ORGANISM: Unknown
<220> FEATURE:
<223> OTHER INFORMATION: Aspergillus fumigatus

<400> SEQUENCE: 11

Met Asp Gly Pro Asp Arg Ile Gly Pro Asp His Ser Pro Arg Arg Thr
1               5                   10                  15

Leu Arg Asp Lys Ala Arg Arg Leu Val Lys Thr Trp Thr Thr Lys Glu
            20                  25                  30

Gly Leu Val Gly Asp Tyr Asn Tyr Ala Tyr Leu Phe Thr Pro Arg Ile
        35                  40                  45

Pro Phe Thr Lys Asn Ile Arg Arg Thr Ala Pro Phe Phe Gly Leu His
    50                  55                  60

Asp Arg Leu Pro Val Leu Leu Ala Phe Ile Leu Gly Leu Gln His Ala
65                  70                  75                  80

Leu Ala Met Leu Ala Gly Val Ile Ser Pro Pro Ile Ile Leu Gly Gly
                85                  90                  95

Ser Ser Gly Ala Asn Phe Gly Asp Ala Glu Tyr Gln Tyr Leu Val Ser
            100                 105                 110

Thr Ser Leu Ile Ala Ser Gly Leu Leu Ser Ala Val Gln Met Ala Arg
        115                 120                 125

Leu Arg Ile Trp Lys Thr Arg Tyr Phe Ile Gly Thr Gly Leu Ile Ser
    130                 135                 140

Val Val Gly Thr Ser Phe Ser Thr Ile Thr Val Ala Ser Gly Thr Phe
```

```
145                 150                 155                 160

Ser Gln Met Tyr Ala Ser Gly Tyr Cys Pro Thr Asp Ala Asn Gly Asn
                165                 170                 175

Arg Leu Pro Cys Pro Arg Gly Tyr Gly Ala Ile Leu Gly Thr Ala Cys
            180                 185                 190

Leu Cys Ser Leu Leu Thr Ile Gly Leu Ser Phe Met Ser Pro Arg Ile
        195                 200                 205

Leu Lys Arg Ile Phe Pro Pro Met Val Thr Gly Pro Thr Val Leu Leu
    210                 215                 220

Ile Gly Ala Ser Leu Ile Glu Ser Gly Met Lys Asp Trp Ala Gly Gly
225                 230                 235                 240

Ser Gly Cys Gly Ser Asp Pro Ser Ala Arg Ala Leu Cys Pro Ser Ala
                245                 250                 255

Gly Ala Pro His Ala Leu Pro Trp Gly Ser Ala Glu Phe Ile Gly Leu
            260                 265                 270

Gly Phe Leu Val Phe Val Thr Ile Ile Leu Cys Glu Arg Phe Gly Ser
        275                 280                 285

Pro Ile Met Lys Ser Cys Ala Val Val Val Gly Leu Leu Val Gly Cys
    290                 295                 300

Ile Val Ala Ala Ala Cys Gly Tyr Phe Asp Arg Ser Gly Ile Asp Ser
305                 310                 315                 320

Ala Pro Val Val Ser Phe Ile Trp Val Lys Thr Phe Pro Leu Thr Ile
                325                 330                 335

Tyr Ala Pro Leu Ile Leu Pro Phe Leu Ala Leu Tyr Ile Val Ile Met
            340                 345                 350

Met Glu Ser Ile Gly Asp Ile Thr Ala Thr Cys Asp Val Ser Gln Leu
        355                 360                 365

Glu Val Glu Gly Ala Asp Phe Asp Ser Arg Val Gln Gly Gly Val Leu
    370                 375                 380

Gly Asn Gly Leu Thr Cys Leu Leu Ala Gly Leu Phe Thr Ile Thr Pro
385                 390                 395                 400

Met Ser Val Phe Ala Gln Asn Asn Gly Val Ile Ala Leu Thr Lys Cys
                405                 410                 415

Ala Asn Arg Lys Ala Gly Tyr Cys Cys Cys Phe Phe Leu Val Val Met
            420                 425                 430

Gly Val Phe Ala Lys Phe Ala Ala Ala Ile Val Ala Ile Pro Lys Pro
        435                 440                 445

Val Leu Gly Gly Met Thr Thr Phe Leu Phe Ser Ser Val Ala Ile Ser
    450                 455                 460

Gly Ile Arg Ile Ile Ser Thr Ile Pro Phe Thr Arg Arg Asn Arg Phe
465                 470                 475                 480

Ile Leu Thr Ala Ser Phe Ala Val Gly Met Ala Ala Thr Leu Val Pro
                485                 490                 495

Asp Trp Phe Ser Tyr Phe Phe Thr Tyr Ser Gly Asp Asn His Ala Leu
            500                 505                 510

Glu Gly Leu Leu Asn Ala Val Glu Leu Val Met Glu Asn Gly Phe Ala
        515                 520                 525

Ile Thr Ala Val Ile Gly Leu Val Leu Asn Leu Val Leu Pro Glu Asp
    530                 535                 540

Pro Glu Asp Glu Ala Ala Ile Val Glu Ala Thr Ala Arg Asp Ala Pro
545                 550                 555                 560

Thr Glu Glu Leu Lys Asp Ser Asp Pro Ser Ser Leu Lys Ala Gly Gln
                565                 570                 575
```

```
Pro Ser Gly Ser Leu Ala Val
            580


<210> SEQ ID NO 12
<211> LENGTH: 591
<212> TYPE: PRT
<213> ORGANISM: Candida albicans

<400> SEQUENCE: 12

Met Ser Ala Ile Gln Lys Thr Leu Lys Arg Met Val Arg Lys Trp Thr
1               5                   10                  15

Thr Lys Asp Gly Leu Leu Gly Asp Tyr Asp Tyr Lys Tyr Leu Phe Thr
            20                  25                  30

Pro Asp Ile Pro Phe Ile Thr Lys Glu Leu Lys Thr Gln Pro Phe Phe
        35                  40                  45

Gly Val Asp Thr Asp Met Pro Ile Leu Leu Gly Ala Ile Leu Gly Phe
    50                  55                  60

Gln His Ala Leu Ala Met Leu Ala Gly Ile Val Thr Val Pro Ile Met
65                  70                  75                  80

Val Ala Ser Thr Ala Asn Leu Ser Val Glu Ile Glu Gln Tyr Leu Val
                85                  90                  95

Ser Thr Ser Ser Ile Val Ser Gly Val Leu Ser Leu Ile Gln Ile Thr
            100                 105                 110

Arg Phe His Ile Pro Lys Thr Pro Tyr Tyr Ile Gly Thr Gly Leu Leu
        115                 120                 125

Ser Val Val Gly Thr Ser Phe Ala Thr Ile Thr Ile Val Thr Lys Ala
    130                 135                 140

Phe Pro Met Met Tyr Ala Asp Gly Thr Cys Pro Met Ala Ser Asp Gly
145                 150                 155                 160

Val Thr Lys Leu Pro Cys Pro Asp Gly Tyr Gly Lys Ile Leu Ala Ser
                165                 170                 175

Ala Cys Cys Cys Ala Leu Leu Glu Ile Leu Leu Ser Phe Met Lys Pro
            180                 185                 190

Ser Met Leu Gln Lys Ile Phe Pro Pro Leu Val Thr Gly Pro Val Val
        195                 200                 205

Met Leu Ile Gly Val His Leu Val Glu Ser Gly Phe Thr Asp Trp Val
    210                 215                 220

Gly Gly Ala Gly Cys Gln Asp Ser Asp Thr Cys Thr Tyr Gly Lys Phe
225                 230                 235                 240

Ser Ala Pro Trp Gly Asp Ala Lys Phe Ile Gly Leu Gly Phe Leu Val
                245                 250                 255

Tyr Val Ser Ile Ile Leu Ala Glu Arg Phe Gly Ala Pro Ile Met Lys
            260                 265                 270

Ser Cys Ala Val Ile Phe Gly Leu Leu Ile Gly Cys Ile Val Ala Ala
        275                 280                 285

Ala Ala Gly Tyr Phe Ser Ser Asp Asn Val Asp Ala Ala Pro Ala Ala
    290                 295                 300

Ser Phe Met Trp Val His Thr Phe Lys Leu Thr Val Tyr Gly Pro Val
305                 310                 315                 320

Val Leu Pro Phe Leu Ala Val Tyr Ile Val Leu Met Met Glu Cys Ile
                325                 330                 335

Gly Asp Val Thr Ala Thr Ser Asp Val Ser Arg Leu Pro Val Ser Gly
            340                 345                 350

Glu Met Tyr Glu Ser Arg Ile Gln Gly Gly Val Leu Gly Asp Gly Ile
```

```
        355                 360                 365

Cys Gly Ile Leu Ser Thr Leu Met Thr Met Thr Pro Met Ser Val Phe
    370                 375                 380

Ala Gln Asn Asn Gly Val Ile Ser Ile Thr Lys Cys Ala Asn Arg Lys
385                 390                 395                 400

Val Gly Tyr Trp Cys Ala Phe Phe Leu Ile Val Met Gly Val Phe Ala
                405                 410                 415

Lys Phe Ala Gly Ala Ile Thr Ser Ile Pro Lys Pro Val Leu Gly Gly
            420                 425                 430

Met Thr Ser Phe Leu Phe Cys Ser Val Ala Ile Ser Gly Ile Lys Ile
        435                 440                 445

Ile Ser Thr Thr Glu Phe Thr Arg Arg Asp Arg Phe Val Leu Thr Ala
    450                 455                 460

Ala Val Ser Pro Gly Leu Gly Ala Thr Met Leu Pro Asn Trp Phe Glu
465                 470                 475                 480

His Val Phe Thr Tyr Gln Gly Gly Asn Lys Ser Leu Lys Gly Phe Phe
                485                 490                 495

Asn Ala Ile Ile Val Val Val Glu Ser Gly Phe Cys Leu Ser Gly Val
            500                 505                 510

Ile Ala Val Ile Leu Asn Leu Leu Ile Pro Gln Val Glu Asp Asp Val
        515                 520                 525

Glu Glu Ile Asn Glu Leu Val Leu Asp Val Val Gly Ser Ala Thr Glu
    530                 535                 540

Ser Ala Arg Gln Lys Phe Glu Glu Lys Glu Gly Val Lys Leu Glu Ala
545                 550                 555                 560

Leu Arg Ser Gln Leu Ser Asn Ile Lys Ser Asn Gly Gly Ser Arg Asp
                565                 570                 575

Ala Ile Thr Val Leu His Arg Asn Asp Gly Phe Pro Asp Leu Lys
            580                 585                 590


<210> SEQ ID NO 13
<211> LENGTH: 601
<212> TYPE: PRT
<213> ORGANISM: Schizosaccharomyces pombe

<400> SEQUENCE: 13

Met Ser Glu Ser Ile Gln Asp Gln Asp His Glu Lys Thr Thr Ile Ile
1               5                   10                  15

Glu Lys Thr Arg Arg Phe Val Leu Ser Ile Phe Thr Lys Asp Phe Trp
            20                  25                  30

Ile Gly Asp Tyr Asp Tyr Ser Phe Leu Leu Pro Ala Ile Pro Phe Thr
        35                  40                  45

Lys Gln Lys Pro Lys Ser Pro Pro Phe Phe Ser Leu Asn Ala Lys Val
    50                  55                  60

Pro Val Leu Leu Ala Leu Leu Leu Gly Phe Gln His Ala Leu Ala Met
65                  70                  75                  80

Val Gly Gly Val Thr Ser Pro Pro Arg Ile Ile Ala Ala Ser Ala Asn
                85                  90                  95

Leu Thr Thr Glu Gln Thr Asn Tyr Leu Val Ser Ala Gly Leu Ile Ser
            100                 105                 110

Ser Gly Ile Met Thr Leu Ile Gln Ile Ala Arg Val His Ile Pro Lys
        115                 120                 125

Thr Lys Tyr Tyr Ile Gly Thr Gly Met Leu Ser Val Leu Gly Ile Ser
    130                 135                 140
```

-continued

```
Phe Thr Ser Val Ser Val Ala Pro Lys Val Leu Ser Gln Met Tyr Glu
145                 150                 155                 160

Asn Gly Tyr Cys Pro Lys Asp Glu Asn Gly Thr Lys Leu Pro Cys Pro
                165                 170                 175

Asp Gly Tyr Gly Ala Phe Leu Ala Thr Ala Cys Val Cys Ser Leu Leu
            180                 185                 190

Glu Ile Phe Met Ser Phe Ile Pro Pro Arg Ile Leu Lys Arg Leu Phe
        195                 200                 205

Pro Pro Ile Val Thr Gly Pro Val Val Leu Leu Ile Gly Thr Ser Leu
    210                 215                 220

Ile Ser Ser Gly Leu Asn Asp Trp Ala Gly Gly Glu Gly Ser Cys Thr
225                 230                 235                 240

Gly Arg Pro Thr Glu Ala Glu Ala Pro Gly Tyr Ser Leu Cys Pro Ser
                245                 250                 255

Asp Thr Ser Pro His Ala Leu Gly Trp Gly Ser Ala Gln Phe Ile Gly
            260                 265                 270

Leu Gly Phe Ser Val Phe Ala Thr Ile Ile Ile Ile Glu Arg Phe Gly
        275                 280                 285

Pro Pro Leu Met Lys Thr Thr Ser Val Val Leu Gly Leu Val Val Gly
    290                 295                 300

Met Ile Ile Ser Ala Ala Thr Gly Tyr Trp Asp His Ser Ile Ile Asp
305                 310                 315                 320

Ala Ala Pro Val Val Thr Phe Asn Trp Val His Thr Phe Arg Leu Arg
                325                 330                 335

Ile Tyr Gly Pro Ala Val Leu Pro Met Leu Ala Leu Tyr Ile Val Asn
            340                 345                 350

Met Met Glu Ala Ile Gly Asp Ile Gly Ala Thr Ser Asp Val Ser Met
        355                 360                 365

Leu Glu Val Asp Gly Pro Ala Phe Asp Ala Arg Val Gln Gly Gly Ile
    370                 375                 380

Leu Gly Asp Gly Leu Ala Ser Leu Ile Ala Ser Leu Met Thr Thr Thr
385                 390                 395                 400

Pro Leu Thr Thr Phe Ala Gln Asn Asn Gly Val Ile Ser Leu Thr Lys
                405                 410                 415

Cys Ala Asn Arg Arg Ala Gly Phe Phe Cys Ala Val Ile Leu Phe Phe
            420                 425                 430

Met Gly Leu Phe Ala Lys Phe Ala Ala Val Phe Val Ala Ile Pro Ser
        435                 440                 445

Pro Val Leu Gly Gly Met Thr Thr Phe Leu Phe Ser Ser Val Ala Val
    450                 455                 460

Ser Gly Ile Ala Ile Ile Ser Gln Ile Pro Phe Asn Arg Arg Asn Arg
465                 470                 475                 480

Phe Ile Leu Thr Ala Ser Met Thr Leu Gly Met Gly Ala Ile Leu Val
                485                 490                 495

Pro Asp Trp Phe Thr Tyr Phe Phe Glu Tyr Ser Gly Pro Asn Lys Ala
            500                 505                 510

Leu Val Gly Phe Leu Asp Ala Ile Thr Leu Val Met Glu Asn Gly Phe
        515                 520                 525

Ala Ile Gly Ala Phe Ile Ser Ile Phe Leu Asn Leu Ile Leu Pro Tyr
    530                 535                 540

Glu Phe Asp Pro Asp Leu Thr Asn Asp Ser Pro Gly Leu Ser Thr Thr
545                 550                 555                 560

Asn Gly Val Asn Asn Gly Ile Val Glu Val Arg Gly Ile Asp Pro Asn
```

```
                565                 570                 575

Asp Ser Leu Ser Asn Thr Asp Thr Glu Tyr Ala Asn Glu Asn Lys Lys
            580                 585                 590

Asp Glu Val Asp Val Asp Lys Val Val
        595                 600


<210> SEQ ID NO 14
<211> LENGTH: 430
<212> TYPE: PRT
<213> ORGANISM: Bacillus subtilis

<400> SEQUENCE: 14

Met Lys Glu Gln His Asn Ala Leu Gln Leu Met Met Leu Gly Leu Gln
1               5                   10                  15

His Met Leu Ala Met Tyr Ala Gly Ala Ile Leu Val Pro Leu Ile Val
            20                  25                  30

Gly Ala Ala Ile Gly Leu Asn Ala Gly Gln Leu Thr Tyr Leu Ile Ala
        35                  40                  45

Ile Asp Leu Phe Met Cys Gly Ala Ala Thr Leu Leu Gln Leu Trp Arg
    50                  55                  60

Asn Arg Tyr Phe Gly Ile Gly Leu Pro Val Val Leu Gly Cys Thr Phe
65                  70                  75                  80

Thr Ala Val Gly Pro Met Ile Ser Ile Gly Ser Thr Tyr Gly Val Pro
                85                  90                  95

Ala Ile Tyr Gly Ala Ile Ile Ala Ala Gly Leu Ile Val Val Leu Ala
            100                 105                 110

Ala Gly Phe Phe Gly Lys Leu Val Arg Phe Phe Pro Pro Val Val Thr
        115                 120                 125

Gly Ser Val Val Met Ile Ile Gly Ile Ser Leu Ile Pro Thr Ala Met
    130                 135                 140

Asn Asn Leu Ala Gly Gly Glu Gly Ser Lys Glu Phe Gly Ser Leu Asp
145                 150                 155                 160

Asn Val Leu Leu Gly Phe Gly Val Thr Ala Phe Ile Leu Leu Leu Phe
                165                 170                 175

Tyr Phe Phe Lys Gly Phe Ile Arg Ser Ile Ala Ile Leu Leu Gly Leu
            180                 185                 190

Ile Ala Gly Thr Ala Ala Ala Tyr Phe Met Gly Lys Val Asp Phe Ser
        195                 200                 205

Glu Val Leu Glu Ala Ser Trp Leu His Val Pro Ser Leu Phe Tyr Phe
    210                 215                 220

Gly Pro Pro Thr Phe Glu Leu Pro Ala Val Val Thr Met Leu Leu Val
225                 230                 235                 240

Ala Ile Val Ser Leu Val Glu Ser Thr Gly Val Tyr Phe Ala Leu Ala
                245                 250                 255

Asp Ile Thr Asn Arg Arg Leu Ser Glu Lys Asp Leu Glu Lys Gly Tyr
            260                 265                 270

Arg Ala Glu Gly Leu Ala Ile Leu Leu Gly Gly Leu Phe Asn Ala Phe
        275                 280                 285

Pro Tyr Thr Ala Phe Ser Gln Asn Val Gly Ile Val Gln Leu Ser Lys
    290                 295                 300

Met Lys Ser Val Asn Val Ile Ala Ile Thr Gly Ile Ile Leu Val Ala
305                 310                 315                 320

Ile Gly Leu Val Pro Lys Ala Ala Ala Leu Thr Thr Val Ile Pro Thr
                325                 330                 335
```

```
Pro Val Leu Gly Gly Ala Met Ile Val Met Phe Gly Met Val Ile Ser
            340                 345                 350

Tyr Gly Ile Lys Met Leu Ser Ser Val Asp Leu Asp Ser Gln Gly Asn
        355                 360                 365

Leu Leu Ile Ile Ala Ser Ser Val Ser Leu Gly Leu Gly Ala Thr Thr
    370                 375                 380

Val Pro Ala Leu Phe Ser Ser Leu Ser Gly Ala Ala Ser Val Leu Ala
385                 390                 395                 400

Gly Ser Gly Ile Val Ile Gly Ser Leu Thr Ala Ile Ala Leu His Ala
                405                 410                 415

Phe Phe Gln Thr Lys Gln Pro Asn Ser Ala Asp Ile Lys Thr
            420                 425                 430


<210> SEQ ID NO 15
<211> LENGTH: 450
<212> TYPE: PRT
<213> ORGANISM: Bacillus subtilis

<400> SEQUENCE: 15

Met Val Lys Lys Arg Ser Phe Lys Val Phe Thr Leu Gly Leu Gln His
1               5                   10                  15

Val Leu Ala Met Tyr Ala Gly Ala Ile Leu Val Pro Leu Leu Val Gly
            20                  25                  30

Arg Ala Leu Asn Val Thr Thr Glu Gln Leu Ser Tyr Leu Leu Ala Ile
        35                  40                  45

Asp Leu Leu Thr Cys Gly Val Ala Thr Leu Leu Gln Thr Leu Arg Gly
    50                  55                  60

Ala Tyr Ile Gly Ile Gly Leu Pro Val Met Leu Gly Ser Ser Phe Val
65                  70                  75                  80

Ala Val Thr Pro Met Ile Ala Ile Gly Ser Asn Tyr Gly Ile His Ala
                85                  90                  95

Ile Tyr Gly Ser Ile Ile Ala Ala Gly Val Phe Ile Phe Leu Phe Ala
            100                 105                 110

Arg Phe Phe Gly Lys Leu Thr Val Leu Phe Pro Pro Val Val Thr Gly
        115                 120                 125

Thr Val Val Thr Leu Ile Gly Leu Ser Leu Val Pro Thr Gly Val Lys
    130                 135                 140

Asn Met Ala Gly Gly Glu Lys Ile Asn Gly Ser Ala Asn Pro Glu Tyr
145                 150                 155                 160

Gly Ser Leu Glu Asn Leu Leu Leu Ser Val Gly Val Leu Val Leu Ile
                165                 170                 175

Leu Val Leu Asn Arg Phe Leu Lys Gly Phe Ala Arg Thr Leu Ser Val
            180                 185                 190

Leu Ile Gly Ile Ala Ala Gly Thr Ala Ala Ala Ala Ile Met Gly Lys
        195                 200                 205

Val Ser Phe Ser Ser Val Thr Glu Ala Pro Phe Phe Gln Ile Pro Lys
    210                 215                 220

Pro Phe Tyr Phe Gly Ala Pro Thr Phe Glu Ile Gly Pro Ile Leu Thr
225                 230                 235                 240

Met Leu Ile Val Gly Ile Val Ile Ile Val Glu Ser Thr Gly Val Phe
                245                 250                 255

Tyr Ala Ile Gly Lys Ile Cys Gly Arg Pro Leu Thr Glu Lys Asp Leu
            260                 265                 270

Val Lys Gly Tyr Arg Ala Glu Gly Ile Ala Ile Leu Ile Gly Gly Leu
        275                 280                 285
```

```
Phe Asn Ala Phe Pro Tyr Asn Thr Phe Ala Gln Asn Ala Gly Leu Leu
    290                 295                 300

Gln Leu Thr Lys Val Lys Thr Arg Asn Ile Val Val Thr Ala Gly Cys
305                 310                 315                 320

Ile Leu Val Cys Leu Gly Leu Ile Pro Lys Ile Ala Ala Leu Ala Ser
                325                 330                 335

Ala Val Pro Ala Ala Val Leu Gly Gly Ala Thr Val Val Met Phe Gly
            340                 345                 350

Met Val Ile Ala Ser Gly Val Lys Met Leu Ser Thr Ala Asp Leu Lys
        355                 360                 365

Asn Gln Tyr His Leu Leu Thr Ile Ala Cys Ser Ile Ala Leu Gly Ile
    370                 375                 380

Gly Ala Ser Thr Ala Pro Gly Ile Phe Ala Glu Phe Pro Ala Pro Ile
385                 390                 395                 400

Arg Ile Leu Val Ser Asp Gly Thr Ile Thr Gly Ser Leu Thr Ala Ile
                405                 410                 415

Phe Leu Asn Leu Phe Phe Ser Leu Arg Asp Lys Lys Glu Leu Thr Ala
            420                 425                 430

Gln Gln Thr Glu Leu Pro Val Leu Glu His Thr Leu Ala Leu Glu Lys
        435                 440                 445

Glu Val
    450


<210> SEQ ID NO 16
<211> LENGTH: 525
<212> TYPE: PRT
<213> ORGANISM: Escherichia coli

<400> SEQUENCE: 16

Met Pro Pro Gln Phe Leu Ser Leu Thr Pro Leu Pro Arg Lys Asn Trp
1               5                   10                  15

His Ser Thr Ser Met Cys Leu Asp Ser Phe Met Asn Ile Asn Gly Cys
            20                  25                  30

Phe Leu Leu Trp Arg Ala Lys Gly Glu Thr Leu Met Asn Ala Ile Asp
        35                  40                  45

Ser Gln Leu Pro Ser Ser Ser Gly Gln Asp Arg Pro Thr Asp Glu Val
    50                  55                  60

Asp Arg Ile Leu Ser Pro Gly Lys Leu Ile Ile Leu Gly Leu Gln His
65                  70                  75                  80

Val Leu Val Met Tyr Ala Gly Ala Val Ala Val Pro Leu Met Ile Gly
                85                  90                  95

Asp Arg Leu Gly Leu Ser Lys Glu Ala Ile Ala Met Leu Ile Ser Ser
            100                 105                 110

Asp Leu Phe Cys Cys Gly Ile Val Thr Leu Leu Gln Cys Ile Gly Ile
        115                 120                 125

Gly Arg Phe Met Gly Ile Arg Leu Pro Val Ile Met Ser Val Thr Phe
    130                 135                 140

Ala Ala Val Thr Pro Met Ile Ala Ile Gly Met Asn Pro Asp Ile Gly
145                 150                 155                 160

Leu Leu Gly Ile Phe Gly Ala Thr Ile Ala Ala Gly Phe Ile Thr Thr
                165                 170                 175

Leu Leu Ala Pro Leu Ile Gly Arg Leu Met Pro Leu Phe Pro Pro Leu
            180                 185                 190

Val Thr Gly Val Val Ile Thr Ser Ile Gly Leu Ser Ile Ile Gln Val
```

```
        195                 200                 205

Gly Ile Asp Trp Ala Ala Gly Gly Lys Gly Asn Pro Gln Tyr Gly Asn
    210                 215                 220

Pro Val Tyr Leu Gly Ile Ser Phe Ala Val Leu Ile Phe Ile Leu Leu
225                 230                 235                 240

Ile Thr Arg Tyr Ala Lys Gly Phe Met Ser Asn Val Ala Val Leu Leu
                245                 250                 255

Gly Ile Val Phe Gly Phe Leu Leu Ser Trp Met Met Asn Glu Val Asn
            260                 265                 270

Leu Ser Gly Leu His Asp Ala Ser Trp Phe Ala Ile Val Thr Pro Met
        275                 280                 285

Ser Phe Gly Met Pro Ile Phe Asp Pro Val Ser Ile Leu Thr Met Thr
    290                 295                 300

Ala Val Leu Ile Ile Val Phe Ile Glu Ser Met Gly Met Phe Leu Ala
305                 310                 315                 320

Leu Gly Glu Ile Val Gly Arg Lys Leu Ser Ser His Asp Ile Ile Arg
                325                 330                 335

Gly Leu Arg Val Asp Gly Val Gly Thr Met Ile Gly Gly Thr Phe Asn
            340                 345                 350

Ser Phe Pro His Thr Ser Phe Ser Gln Asn Val Gly Leu Val Ser Val
        355                 360                 365

Thr Arg Val His Ser Arg Trp Val Cys Ile Ala Ser Gly Ile Ile Leu
    370                 375                 380

Ile Leu Phe Gly Met Val Pro Lys Met Ala Val Leu Val Ala Ser Ile
385                 390                 395                 400

Pro Gln Phe Val Leu Gly Gly Ala Gly Leu Val Met Phe Gly Met Val
                405                 410                 415

Leu Ala Thr Gly Ile Arg Ile Leu Ser Arg Cys Asn Tyr Thr Thr Asn
            420                 425                 430

Arg Tyr Asn Leu Tyr Ile Val Ala Ile Ser Leu Gly Val Gly Met Thr
        435                 440                 445

Pro Thr Leu Ser His Asp Phe Phe Ser Lys Leu Pro Ala Val Leu Gln
    450                 455                 460

Pro Leu Leu His Ser Gly Ile Met Leu Ala Thr Leu Ser Ala Val Val
465                 470                 475                 480

Leu Asn Val Phe Phe Asn Gly Tyr Gln His His Ala Asp Leu Val Lys
                485                 490                 495

Glu Ser Val Ser Asp Lys Asp Leu Lys Val Arg Thr Val Arg Met Trp
            500                 505                 510

Leu Leu Met Arg Lys Leu Lys Lys Asn Glu His Gly Glu
        515                 520                 525


<210> SEQ ID NO 17
<211> LENGTH: 594
<212> TYPE: PRT
<213> ORGANISM: Unknown
<220> FEATURE:
<223> OTHER INFORMATION: zygosaccharomyces parabailii

<400> SEQUENCE: 17

Met Asp Ser Val Leu Glu Gln Pro Thr Asn Ser Pro Ser Gln Lys Ile
1               5                   10                  15

Lys Gly Tyr Phe Ser Trp Leu Arg Phe Lys Phe Thr Thr Arg Asp Gly
            20                  25                  30

Leu Leu Gly Asp Tyr Asp Tyr Lys Tyr Leu Phe Thr Pro Ser Tyr Pro
```

-continued

```
        35                  40                  45

Phe His Asp Phe Ile Cys Arg Leu Arg Gly Val Glu Val Val Val Arg
    50                  55                  60

Asp Gln Pro Phe Phe Gly Leu Asn Glu Glu Val Pro Val Leu Leu Gly
65                  70                  75                  80

Met Ile Leu Gly Phe Gln His Ala Leu Ala Met Leu Ala Gly Val Ile
                85                  90                  95

Thr Pro Pro Met Met Ile Ala Ser Ala Ala Asn Leu Asp Ser Val Leu
            100                 105                 110

Thr Asn Tyr Leu Val Ser Ala Ser Leu Ile Thr Ser Gly Ile Leu Ser
        115                 120                 125

Ala Val Gln Ile Thr Arg Phe His Ile Pro Lys Thr Asn Tyr Tyr Ile
    130                 135                 140

Gly Ser Gly Val Leu Ser Ile Val Gly Thr Ser Phe Ala Val Leu Gly
145                 150                 155                 160

Ile Val Asp Lys Ser Val Pro Leu Met Tyr Ser Thr Gly Tyr Cys Pro
                165                 170                 175

Gly Gly Ala Asn Ser Lys Glu Ala Cys Pro Asp Gly Tyr Gly Ala Leu
            180                 185                 190

Leu Gly Thr Ala Ala Cys Cys Ala Leu Leu Glu Met Leu Leu Ser Phe
        195                 200                 205

Thr Pro Pro His Ile Leu Gln Lys Ile Phe Pro Lys Gln Val Thr Gly
    210                 215                 220

Pro Val Val Leu Thr Ile Ala Val Pro Leu Ile Gln Ser Gly Phe Glu
225                 230                 235                 240

Asp Trp Val Gly Gly Ser Gly Cys Val Gly Ala Ile Cys Pro Ser Glu
                245                 250                 255

Gly Ala Pro Gln Ala Ala Pro Trp Gly Ser Ala Lys Phe Ile Gly Leu
            260                 265                 270

Gly Phe Leu Val Tyr Thr Thr Ile Ile Leu Cys Glu Lys Tyr Gly Pro
        275                 280                 285

Pro Ile Leu Lys Ser Cys Ala Val Ile Val Gly Leu Leu Val Gly Cys
    290                 295                 300

Ile Val Ala Ala Ala Cys Gly Tyr Phe Gln His Asp Met Ile Asp Val
305                 310                 315                 320

Ala Pro Ala Ala Thr Phe Leu Trp Lys His Thr Phe Arg Leu Arg Val
                325                 330                 335

Tyr Gly Pro Ala Val Leu Pro Phe Leu Val Met Phe Ile Val Leu Ala
            340                 345                 350

Gln Glu Cys Ile Gly Asp Ile Thr Ala Thr Ser Asp Val Ser Arg Leu
        355                 360                 365

Glu Val Glu Gly Glu Ala Tyr Glu Ser Arg Ile Gln Gly Ala Val Leu
    370                 375                 380

Ser Asp Gly Ile Gly Gly Ile Leu Ser Ser Leu Phe Thr Val Thr Pro
385                 390                 395                 400

Met Ser Thr Phe Ala Gln Asn Asn Gly Val Ile Ser Leu Thr Lys Cys
                405                 410                 415

Ala Ser Arg Gln Ala Gly Tyr Trp Thr Cys Phe Tyr Met Leu Ile Met
            420                 425                 430

Gly Ile Phe Ala Lys Phe Gly Ala Ala Ile Val Gln Ile Pro Lys Pro
        435                 440                 445

Val Leu Gly Gly Met Thr Thr Phe Leu Phe Thr Thr Val Ala Val Ala
    450                 455                 460
```

```
Gly Ile Lys Ile Ile Ser Glu Ile Pro Phe Thr Arg Arg Asp Arg Phe
465                 470                 475                 480

Val Leu Thr Gly Ala Leu Leu Pro Gly Phe Gly Ser Ile Leu Val Ser
                485                 490                 495

Asp Trp Phe Asp Tyr Val Phe Thr Tyr Lys Gly Asn Asn His Ala Leu
            500                 505                 510

Glu Gly Phe Phe Asn Ala Ile Ile Leu Ile Met Glu Thr Ser Phe Thr
        515                 520                 525

Val Cys Gly Leu Thr Ala Ile Ile Leu Asn Leu Leu Ile Pro Gln Glu
    530                 535                 540

Leu Asp Glu Glu Leu Leu Asp Asp Ile Glu Val Gln Gln Glu Asn Leu
545                 550                 555                 560

Ser Val Leu Glu Gly Arg Lys Ser Pro Leu Ile Gly Pro Val Met Ser
                565                 570                 575

Gly Lys Glu Ile Glu Ala Phe Glu Leu Ser Ser Glu Gln Arg Thr Ser
            580                 585                 590

Asp Pro


<210> SEQ ID NO 18
<211> LENGTH: 451
<212> TYPE: PRT
<213> ORGANISM: Unknown
<220> FEATURE:
<223> OTHER INFORMATION: Spirosoma sp. KCTC 42546

<400> SEQUENCE: 18

Met Ser Glu Pro Val Asn Ala Gln Ser Thr Arg Leu Val Tyr Gly Leu
1               5                   10                  15

Glu Asp Lys Val Pro Leu Val Pro Ala Leu Leu Val Ser Leu Gln Gln
            20                  25                  30

Val Gly Ala Met Val Val Gly Thr Ile Thr Pro Ala Leu Ile Leu Ser
        35                  40                  45

Gly Ile Leu His Phe Asp Pro Gln Asp Thr Ala Tyr Leu Val Ser Met
    50                  55                  60

Ala Leu Val Ala Ser Ala Leu Gly Thr Phe Leu Gln Thr Met Arg Leu
65                  70                  75                  80

Gly Phe Ile Gly Ser Gly Leu Leu Ser Ile Thr Gly Thr Ser Phe Ala
                85                  90                  95

Phe Leu Ala Pro Leu Ile Gln Ala Gly Val Thr Gly Gly Leu Pro Leu
            100                 105                 110

Met Val Gly Met Ser Leu Ala Gly Thr Pro Val Gln Leu Ala Leu Ala
        115                 120                 125

Pro Phe Leu Pro Lys Leu Lys Arg Val Phe Thr Pro Leu Val Ser Gly
    130                 135                 140

Ile Val Val Leu Leu Ile Gly Leu Ser Leu Ile Pro Thr Gly Met Arg
145                 150                 155                 160

Ser Ile Ala Gln Leu Pro Ala Glu Gly Ala Pro Ala Trp Ser Gly Gly
                165                 170                 175

Leu Val Ala Leu Ile Val Ile Val Val Met Ile Ile Ala Gln Ser Ile
            180                 185                 190

Gly Lys Ala Trp Ala Arg Met Ala Ala Val Leu Val Gly Val Val Thr
        195                 200                 205

Gly Tyr Thr Ile Cys Gly Leu Met Gly Trp Leu Gln Ser Pro Ala Pro
    210                 215                 220
```

```
Ser Asn Gly Ser Trp Leu Thr Leu Pro Gln Leu Phe Pro Tyr Gly Leu
225                 230                 235                 240

Ala Phe Lys Trp Glu Leu Leu Phe Pro Phe Ala Phe Ile Tyr Leu Val
                245                 250                 255

Cys Val Leu Glu Ala Met Gly Asp Ile Thr Ala Thr Ser Gln Leu Ser
            260                 265                 270

Gly Leu Pro Thr Asp Gly Pro Asp His Trp Ala Arg Ile Arg Gly Gly
        275                 280                 285

Ile Leu Ala Asp Gly Leu Thr Cys Ile Gly Ser Thr Leu Ile Gly Gly
    290                 295                 300

Phe Pro Ser Ala Thr Tyr Ala Gln Asn Asn Gly Val Ile Gln Met Thr
305                 310                 315                 320

Gly Val Ala Ala Arg Arg Ile Gly Trp Ile Met Ala Val Ile Leu Leu
                325                 330                 335

Cys Leu Gly Leu Phe Pro Pro Val Gly Arg Trp Ile Thr Val Met Pro
            340                 345                 350

Ser Cys Val Leu Gly Ala Leu Ala Ile Met Leu Phe Gly Leu Val Ala
        355                 360                 365

Val Ser Gly Leu Arg Leu Met Val Ser Gly Gly Leu Ser Gln Arg Asp
    370                 375                 380

Ala Leu Ile Ala Ala Ile Ser Leu Gly Val Gly Ile Gly Val Pro Ser
385                 390                 395                 400

Gln Glu Glu Trp Leu Lys Thr Leu Pro Thr Val Val Gln Thr Phe Leu
                405                 410                 415

Glu Ser Gly Val Ser Ala Gly Gly Leu Ala Ala Leu Leu Leu Asn Leu
            420                 425                 430

Leu Leu Pro Ala Glu Gly Arg Lys Lys Met Met Gly Lys Glu Pro Ala
        435                 440                 445

Glu Met Leu
    450


<210> SEQ ID NO 19
<211> LENGTH: 9930
<212> TYPE: DNA
<213> ORGANISM: Artificial Sequence
<220> FEATURE:
<223> OTHER INFORMATION: synthetic contrsuct / Exemplary Saccharomyces
      shuttle vector

<400> SEQUENCE: 19

cggatcccgg gcgagtttat cattatcaat actgccattt caaagaatac gtaaataatt      60

aatagtagtg attttcctaa ctttatttag tcaaaaaatt ggccttttaa ttctgctgta     120

acccgtacat gcccaaaata gggggcgggt tacacagaat atataacatc ataggtgtct     180

gggtgaacag tttattcctg gcatccacta aatataatgg agcccgcttt ttaagctggc     240

atccagaaaa aaaaagaatc ccagcaccaa aatattgttt tcttcaccaa ccatcagttc     300

ataggtccat tctcttagcg caactacaca gaacaggggc acaaacaggc aaaaaacggg     360

cacaacctca atggagtgat gcaacctgct tggagtaaat gatgacacaa ggcaattgac     420

ctacgcatgt atctatctca ttttcttaca ccttctatta ccttctgctc tctctgattt     480

ggaaaaagct gaaaaaaaag gttgaaacca gttccctgaa attattcccc tatttgacta     540

ataagtatat aaagacggta ggtattgatt gtaattctgt aaatctattt cttaaacttc     600

ttaaattcta cttttatagt tagtcttttt tttagtttta aaacactaag aacttagttt     660

cgaagttaac atttaaatca aacaaaatgt caacaacgct ctcatcatcc acttacggca     720
```

```
aggacaacgt caagttcctc aaggtcaaga aagatccgca gaacccaaag aagcaggagg    780
ttatggaggc caccgtcacg tgtctgcttg aaggtgggtt cgacacctcg tacacggagg    840
ctgacaactc gtccatcgtg ccaacagaca ccgtgaagaa caccattctc gtgttggcaa    900
agaccacgga gatttggcca attgagagat ttgcagccaa gctggccacg cactttgttg    960
agaagtactc gcacgtctct ggcgtctccg tcaagattgt ccaggacaga tgggtcaagt   1020
acgccgttga cggcaagcca cacgaccact cttttatcca cgaaggtggt gagaagagaa   1080
tcactgacct gtactacaag agatccggtg attacaagct gtcatctgcc atcaaggact   1140
tgacggtgct gaagtccacc ggctcgatgt tctacggcta caacaagtgt gacttcacca   1200
ccttgcaacc aaccactgac agaatcttgt ccaccgacgt cgatgccacc tgggtttggg   1260
ataacaagaa gattggcact gtctacgaca tcgccaaggc tgcagacaag gggatctttg   1320
acaacgttta caaccaggct agagagatca ccttgaccac cttcgccctg gagaactctc   1380
catctgtgca ggccacgatg ttcaacatgg ctactcagat cttggaaaag gcatgctctg   1440
tctactcggt ttcatacgcc ttgccaaaca agcactactt cctcattgac ttgaaatgga   1500
aaggtttgga gaacgacaac gagttgttct acccatctcc acatccaaat ggtttgatca   1560
agtgtactgt tgtccgtaag gagaagacca agttgtaatc acatatgaaa gtatataccc   1620
gcttttgtac actatgtagc tataattcaa tcgtattatt gtagctccgc acgaccatgc   1680
cttagaaata tccgcagcgc gggatccgat atcctactta ttcccttcga gattatatct   1740
aggaacccat caggttggtg gaagattacc cgttctaaga cttttcagct tcctctattg   1800
atgttacacc tggacacccc ttttctggca tccagttttt aatcttcagt ggcatgtgag   1860
attctccgaa attaattaaa gcaatcacac aattctctcg gataccacct cggttgaaac   1920
tgacaggtgg tttgttacgc atgctaatgc aaaggagcct atatacctt ggctcggctg    1980
ctgtaacagg gaatataaag ggcagcataa tttaggagtt tagtgaactt gcaacattta   2040
ctattttccc ttcttacgta aatatttttc tttttaattc taaatcaatc tttttcaatt   2100
ttttgtttgt attcttttct tgcttaaatc tataactaca aaaaacacat acataaacta   2160
aaagtgttga caattaatca tcggcatagt atatcggcat agtataatac gacaaggtga   2220
ggaactaaac catgggtaag gaaaagactc acgtttcgag gccgcgatta aattccaaca   2280
tggatgctga tttatatggg tataaatggg ctcgcgataa tgtcgggcaa tcaggtgcga   2340
caatctatcg attgtatggg aagcccgatg cgccagagtt gtttctgaaa catggcaaag   2400
gtagcgttgc caatgatgtt acagatgaga tggtcagact aaactggctg acggaattta   2460
tgcctcttcc gaccatcaag cattttatcc gtactcctga tgatgcatgg ttactcacca   2520
ctgcgatccc cggcaaaaca gcattccagg tattagaaga atatcctgat tcaggtgaaa   2580
atattgttga tgcgctggca gtgttcctgc gccggttgca ttcgattcct gtttgtaatt   2640
gtccttttaa cagcgatcgc gtatttcgtc tcgctcaggc gcaatcacga atgaataacg   2700
gtttggttga tgcgagtgat tttgatgacg agcgtaatgg ctggcctgtt gaacaagtct   2760
ggaaagaaat gcataagctt ttgccattct caccggattc agtcgtcact catggtgatt   2820
tctcacttga taaccttatt tttgacgagg ggaaattaat aggttgtatt gatgttggac   2880
gagtcggaat cgcagaccga taccaggatc ttgccatcct atggaactgc ctcggtgagt   2940
tttctccttc attacagaaa cggctttttc aaaaatatgg tattgataat cctgatatga   3000
ataaattgca gtttcatttg atgctcgatg agtttttcta atcagtactg acaataaaaa   3060
```

-continued

```
gattcttgtt ttcaagaact tgtcatttgt atagtttttt tatattgtag ttgttctatt   3120
ttaatcaaat gttagcgtga tttatatttt ttttcgcctc gacatcatct gcccagatgc   3180
gaagttaagt gcgcagaaag taatatcatg cgtcaatcgt atgtgaatgc tggtcgctat   3240
actgctgtcg attcgatact aacgccgcca tccagtttaa acgagctcga attcatcgat   3300
gatatcagat ccactagtgg cctatgcggc cgcatcagtt ctggaccagc gagctgtgct   3360
gcgactcgtg gcgtaatcat ggtcatagct gtttcctgtg tgaaattgtt atccgctcac   3420
aattccacac aacatacgag ccggaagcat aaagtgtaaa gcctggggtg cctaatgagt   3480
gagctaactc acattaattg cgttgcgctc actgcccgct ttccagtcgg gaaacctgtc   3540
gtgccagctg cattaatgaa tcggccaacg cgcggggaga ggcggtttgc gtattgggcg   3600
ctcttccgct tcctcgctca ctgactcgct gcgctcggtc gttcggctgc ggcgagcggt   3660
atcagctcac tcaaaggcgg taatacggtt atccacagaa tcaggggata acgcaggaaa   3720
gaacatgtga gcaaaaggcc agcaaaaggc caggaaccgt aaaaaggccg cgttgctggc   3780
gtttttccat aggctccgcc cccctgacga gcatcacaaa aatcgacgct caagtcagag   3840
gtggcgaaac ccgacaggac tataaagata ccaggcgttt ccccctggaa gctccctcgt   3900
gcgctctcct gttccgaccc tgtcgcttac cggatacctg tccgcctttc tcccttcggg   3960
aagcgtggcg ctttctcata gctcacgctg taggtatctc agttcggtgt aggtcgttcg   4020
ctccaagctg ggctgtgtgc acgaaccccc cgttcagccc gaccgctgcg ccttatccgg   4080
taactatcgt cttgagtcca acccggtaag acacgactta tcgccactgg cagcagccac   4140
tggtaacagg attagcagag cgaggtatgt aggcggtgct acagagttct tgaagtggtg   4200
gcctaactac ggctacacta gaagaacagt atttggtatc tgcgctctgc tgaagccagt   4260
taccttcgga aaaagagttg gtagctcttg atccggcaaa caaaccaccg ctggtagcgg   4320
tggttttttt gtttgcaagc agcagattac gcgcagaaaa aaaggatctc aagaagatcc   4380
tttgatcttt tctacggggt ctgacgctca gtggaacgaa aactcacgtt aagggatttt   4440
ggtcatgaga ttatcaaaaa ggatcttcac ctagatcctt ttaaattaaa aatgaagttt   4500
taaatcaatc taaagtatat atgagtaaac ttggtctgac agttaccaat gcttaatcag   4560
tgaggcacct atctcagcga tctgtctatt tcgttcatcc atagttgcct gactccccgt   4620
cgtgtagata actacgatac gggagggctt accatctggc cccagtgctg caatgatacc   4680
gcgagaccca cgctcaccgg ctccagattt atcagcaata aaccagccag ccggaagggc   4740
cgagcgcaga agtggtcctg caactttatc cgcctccatc cagtctatta attgttgccg   4800
ggaagctaga gtaagtagtt cgccagttaa tagtttgcgc aacgttgttg ccattgctac   4860
aggcatcgtg gtgtcacgct cgtcgtttgg tatggcttca ttcagctccg gttcccaacg   4920
atcaaggcga gttacatgat cccccatgtt gtgcaaaaaa gcggttagct ccttcggtcc   4980
tccgatcgtt gtcagaagta agttggccgc agtgttatca ctcatggtta tggcagcact   5040
gcataattct cttactgtca tgccatccgt aagatgcttt tctgtgactg gtgagtactc   5100
aaccaagtca ttctgagaat agtgtatgcg gcgaccgagt tgctcttgcc cggcgtcaat   5160
acgggataat accgcgccac atagcagaac tttaaaagtg ctcatcattg gaaaacgttc   5220
ttcggggcga aaactctcaa ggatcttacc gctgttgaga tccagttcga tgtaacccac   5280
tcgtgcaccc aactgatctt cagcatcttt tactttcacc agcgtttctg ggtgagcaaa   5340
aacaggaagg caaaatgccg caaaaaaggg aataagggcg acacggaaat gttgaatact   5400
catactctac ctttttcaat attattgaag catttatcag ggttattgtc tcatgagcgg   5460
```

```
atacatattt gaatgtattt agaaaaataa acaaataggg gttccgcgca catttccccg   5520

aaaagtgcca cctgacgtct aagaaaccat tattatcatg acattaacct ataaaaatag   5580

gcgtatcacg aggccctttc gtctcgcgcg tttcggtgat gacggtgaaa acctctgaca   5640

catgcagctc ccggagacgg tcacagcttg tctgtaagcg gatgccggga gcagacaagc   5700

ccgtcagggc gcgtcagcgg gtgttggcgg gtgtcggggc tggcttaact atgcggcatc   5760

agagcagatt gtactgagag tgcaccaaat gcggtgtgaa ataccgcaca gatgcgtaag   5820

gagaaaatac cgcatcaggc gccattcgcc attcaggctg cgcaactgtt gggaagggcg   5880

atcggtgcgg gcctcatcgc tattacgcca gctggcgaaa gggggatgtg ctgcaaggcg   5940

attaagttgg gtaacgccag ggttttccca gtcacgacgt tgtaaaacga cggccagtgc   6000

aacgcgatga cgatggatag cgattcatcg ataacgaagc atctgtgctt catttgtag   6060

aacaaaaatg caacgcgaga gcgctaattt ttcaaacaaa gaatctgagc tgcattttta   6120

cagaacagaa atgcaacgcg aaagcgctat tttaccaacg aagaatctgt gcttcatttt   6180

tgtaaaacaa aaatgcaacg cgagagcgct aatttttcaa acaaagaatc tgagctgcat   6240

ttttacagaa cagaaatgca acgcgagagc gctattttac caacaaagaa tctatacttc   6300

ttttttgttc tacaaaaatg catcccgaga gcgctatttt tctaacaaag catcttagat   6360

tacttttttt ctcctttgtg cgctctataa tgcagtctct tgataacttt ttgcactgta   6420

ggtccgttaa ggttagaaga aggctacttt ggtgtctatt ttctcttcca taaaaaaagc   6480

ctgactccac ttcccgcgtt tactgattac tagcgaagct gcgggtgcat tttttcaaga   6540

taaaggcatc cccgattata ttctataccg atgtggattg cgcatacttt gtgaacagaa   6600

agtgatagcg ttgatgattc ttcattggtc agaaaattat gaacggtttc ttctattttg   6660

tctctatata ctacgtatag gaaatgttta cattttcgta ttgttttcga ttcactctat   6720

gaatagttct tactacaatt tttttgtcta aagagtaata ctagagataa acataaaaaa   6780

tgtagaggtc gagtttagat gcaagttcaa ggagcgaaag gtggatgggt aggttatata   6840

gggatatagc acagagatat atagcaaaga gatacttttg agcaatgttt gtggaagcgg   6900

tattcgcaat attttagtag ctcgttacag tccggtgcgt ttttggtttt ttgaaagtgc   6960

gtcttcagag cgcttttggt tttcaaaagc gctctgaagt tcctatactt tctagagaat   7020

aggaacttcg gaataggaac ttcaaagcgt ttccgaaaac gagcgcttcc gaaaatgcaa   7080

cgcgagctgc gcacatacag ctcactgttc acgtcgcacc tatatctgcg tgttgcctgt   7140

atatatatat acatgagaag aacggcatag tgcgtgttta tgcttaaatg cgtacttata   7200

tgcgtctatt tatgtaggat gaaaggtagt ctagtacctc ctgtgatatt atcccattcc   7260

atgcggggta tcgtatgctt ccttcagcac taccctttag ctgttctata tgctgccact   7320

cctcaattgg attagtctca tccttcaatg ctatcatttc ctttgatatt ggatcataaa   7380

gcttataacc taggaagctt gggcccgaat tcattttcaa catcgtattt tccgaagcgt   7440

tgcataatga aaatgtgata ataaggcagt gagctacttt gtcacaacaa agtacgagaa   7500

cagatgaggt tccgtggtgt ttttggggca accgcactat ttggagcgct gtatatattt   7560

atatcctact acaaaaaatc ataaatgaca ctgaattgga cacatgctag cgtcaaatac   7620

cttgcctggt aaagttgtgt gctagtgtct cccgtcttct gtctaagcct gcttgctctg   7680

atactccgcc tcgccatccc gattatcatg agcagagacc ggcatagggg tgacggcacc   7740

gatctcttcg acttcagcag gcatgattgc gttcaagagc atagcaacaa atgccgtgac   7800
```

```
cgcaaacccc gtctcaagca cgagctcgat cgcattttca aacccctcca ggtctctatt   7860

ctcggtctga gggaatacat tcccaaacca agtgggcacc agcgtcgccc cgtatcccag   7920

ggccattgac gcggtgagga taaaccgatt tcgccttgtg aacggcgcct tggccacgat   7980

cgcctgtccg ctaataacga ccgaagcgaa gagaaacgtc ttcatcccgc ccatgacact   8040

gttgggtatg gcaacaatgg ctgcagcgaa tttagcaaag ataccggcta ctatcaatat   8100

cagacagcag cagtatccgg cccagcggtt tgcgcagcga gtgagggcaa tcacgccgtt   8160

gttctgcgca aaggtcgtca tgggggtcat tgtcgcaagg gcagcgacta ccgagttgat   8220

cccgtctgct aggacggcgc cctggatgcg cgactcgaat gtgccgccgc ggacttcgag   8280

acgcgagacg tcgcaggtgg cggttacatc accgatgcac tcgcaggcgc agatgatgaa   8340

aaccgcgatg atcgggagaa ccatcggacc atagacagag agagggaaag tcttgaccca   8400

gatgaatgag gcggcagggg cagcgtcaat atcggcgtgg ctgaagtagc cgcaggctgc   8460

agcgactata caaccgacga gcagcccgat gacaacagaa caggacttca taatcggggc   8520

tccaaatcgt tcgcagagga tgatcgatac aaagactaga aaacccaggc cgatgaactc   8580

tggactcccc cacgggagag ggcgcggtgc agttgcggac gggcacagca tcccgtcatc   8640

catacacgcc gagccgccag cccagtcttt gaacccagtt ccaatcagac ttatcccgat   8700

aagcattaca gtgggaccag tgacgatggg cgggaagatt ttctgtatca ctttgggagg   8760

cacgaaagcg aggaggatct ccaccaaagc acagcaggcc gaggtgccaa tcaaggcgcc   8820

gtacgcttcg gggcaaggga gtctgtttcc agcctcgtcg agttgacaga acccgttcga   8880

gtacatctgg ttgaaggcgc cgctggcgac ggagatgatg gagaacgaga cccccataac   8940

tgagaggacg ccactgccga tatagtacgg tgtcttgtag atatgaaatc gcgttatctg   9000

gaccatcgac agcagcccgc agacgataag cgaggtcgaa acgagatact gctggagatc   9060

ggacggcagg ctcagcgagc ttgatatgat cagaggagga gtgaccacac ccgccaacat   9120

ggcaagcgca tgctgaagac ccaggataaa cgccaacagc acgggaatct tctcgttgag   9180

gccaaaaaaa ggcggcgccc gtggatcttt cttcatgaag ggtagctcgg gccggaaaag   9240

gaagccatag tcatagtcgc cgatcaggcc ctcgcgggtc gtcagatgcc tagccagcaa   9300

gcggactctc tgtcggacgg tcttcttggg gttggagttg gggatgacgg agtcggggcc   9360

gtcggttgaa tggatggagt tgtccattgt tttatatttg ttgtaaaaag tagataatta   9420

cttccttgat gatctgtaaa aaagagaaaa agaaagcatc taagaacttg aaaaactaag   9480

aattagaaaa gaccaaatat gtatttcttg cattgaccaa tttatgcaag tttatatata   9540

tgtaaatgta agtttcacga ggttctacta aactaaacca ccccccttggt tagaagaaaa   9600

gagtgtgtga gaacaggctg ttgttgtcac acgattcgga caattctgtt tgaaagagag   9660

agagtaacag tacgatcgaa cgaactttgc tctggagatc acagtgggca tcatagcatg   9720

tggtactaaa ccctttcccg ccattccaga accttcgatt gcttgttaca aaacctgtga   9780

gccgtcgcta ggaccttgtt gtgtgacgaa attggaagct gcaatcaata ggaagacagg   9840

aagtcgagcg tgtctgggtt ttttcagttt tgttcttttt gcaaacaaat cacgagcgac   9900

ggtaatttct ttctcgataa gaggcggtac                                    9930
```

<210> SEQ ID NO 20
<211> LENGTH: 1272
<212> TYPE: DNA
<213> ORGANISM: Artificial Sequence
<220> FEATURE:
<223> OTHER INFORMATION: synthetic construct / Exemplary E. coli malE/K expression cassette

<400> SEQUENCE: 20

```
gcggccgctt gcaagcaaca tcacgaaatt ccttacatga cctcggttta gttcacaggg      60
taccagttgt tcttattggt ggtgttgctt tatggttgca tcgtagtaaa tggttgtaac     120
aaaagcaatt tttccggctg tctgtataca aaaacgccgc aaagtttgag cgaagtcaat     180
aaactctcta cccattcagg gcaatatctc tcttggatcc aaagtgaact ctagaaataa     240
ttttgtttaa ctttaagaag gagatataca tatgactgcc accgcagaaa cctcaaccgg     300
caccaaggtc gtgctcggac agaaccagta cggcaaggcc gaagtccgcc tcgtcaaggt     360
cacgcgcaat accgcccggc acgagatcca ggacctgaat gtcacctcgc agctgcgcgg     420
cgacttcgag gccgcacaca ccgccggcga caacgcgcac gtggtcgcca ccgacacgca     480
gaagaacacc gtctacgcct tcgcccgcga cggcttcgcc accaccgagg agttcctgct     540
ccggctgggc aaacacttca ccgagggctt cgactgggta accggcgggc gctgggcggc     600
gcagcagttc ttctgggacc gcatcaacga ccacgaccac gccttctccc ggaacaagag     660
cgaggtccgc accgccgtgc tcgagatctc gggcagcgag caggccatcg tcgccgggat     720
cgagggcctg acggtcctga agtccaccgg ttcggaattc cacggcttcc cgcgggacaa     780
gtacaccacc ctgcaggaaa ccaccgaccg tatcctcgcc acggatgtca gcgcccgctg     840
gcgctacaac accgtcgagg ttgacttcga cgccgtctac gcgagcgtcc gcgggctgct     900
gctcaaggcc ttcgccgaga cccactcgct ggccctgcag cagaccatgt atgagatggg     960
ccgggccgtc atcgagacgc acccggaaat cgacgaaatc aagatgtccc tgccgaacaa    1020
gcaccatttc ctggtggacc tgcagccctt cggacaggac aacccgaatg aggtgttcta    1080
cgccgccgac cgtccctacg gactgatcga agccaccatc cagcgcgagg gctcgcgcgc    1140
cgaccacccg atctggtcga acatcgccgg attctgctag cgcaaaaaac cccgcttcgg    1200
cggggttttt tcgcaagccg cgttctcatc ctcccgcctc ctcccccata aaaaagccag    1260
gggggcggcc gc                                                        1272
```

<210> SEQ ID NO 21
<211> LENGTH: 1960
<212> TYPE: DNA
<213> ORGANISM: Artificial Sequence
<220> FEATURE:
<223> OTHER INFORMATION: synthetic construct / Exemplary E. coli LacZ expression cassette

<400> SEQUENCE: 21

```
gcggccgcga cgccattgct gccaggcgct gatgtgtccg gcttctgacc atgcggtcgc      60
gtttggttgc actacgcgta ccgttagcca gagtcacatt tccccgaaaa gtgccacctg     120
catcgatggc cccggtacca gttgttctta ttggtggtgt tgctttatgg ttgcatcgta     180
gtaaatggtt gtaacaaaag caatttttcc ggctgtctgt atacaaaaac gccgtaaagt     240
ttgagcgaag tcaataaact ctctacccat tcagggcaat atctctcttg gatccaaagt     300
gaactctaga aataattttg tttaacttta agaaggagat atacatatgt gtttagacag     360
tttcattaac gtaaacggtt gcttttttatt ctggcgggcg aaaggagaaa cactgatgag     420
cgccatagat tcccaacttc cctcatcttc tgggcaagac cgcccaactg atgaggttga     480
ccgcatatta tcaccaggaa agctgatcat actcggtctg caacacgtcc ttgtcatgta     540
cgcaggtgca gtcgctgttc ctcttatgat tggtgaccga ctgggcctct caaaagatgc     600
```

```
tattgcgatg ctcattagct cggatctctt ttgctgcggg atcgtcacat tattgcaatg    660

tatcggtatc ggccgcttta tggggatccg cctgccggtg attatgtcgg tgacctttgc    720

tgctgtaaca ccaatgatag ccattgggat gaacccggat atcggcctgc tggggatatt    780

tggtgccact atcgccgcgg gttttatcac cacattatta gcgccactta ttggtcgctt    840

gatgccttta ttcccgccac tggttaccgg tgtggttatt acttctattg ggcttagcat    900

cattcaggtg ggtattgact gggccgctgg aggtaaaggg aatccgcaat atggtaatcc    960

cgtttattta ggtatctcct ttgccgtctt aatttttatc ttgctcatta ctcgctatgc   1020

gaaaggattt atgtccaacg tcgccgtatt actggggatt gtatttggct ttttactttc   1080

gtggatgatg aatgaagtca atttatccgg gctacatgat gcctcgtggt ttgcgattgt   1140

caccccgatg tcgtttggta tgccgatttt cgatcccgtt tccattctga ccatgactgc   1200

cgtgttaatc atcgtgttta tcgagtcgat ggggatgttc ctggcactgg gtgaaatagt   1260

cggtcgtaaa ctctcttcac acgatattat ttgcgggctg cgtgtcgatg gcgtagggac   1320

aatgataggc ggcacgttta acagcttccc ccacacgtca ttttctcaaa acgttggcct   1380

ggttagcgtg atgcgcgttc atagccgctg ggtgtgtatt tcttcgggaa ttatattaat   1440

cctgtttggc atggtgccaa aaatggcggt gctggtagcc tccattccgc aatttgtgct   1500

gggcggcgct ggtctagtga tgttcggcat ggtactggcg acagggattc gaattctgtc   1560

gcgctgtaac tacaccacca accgttacaa cctctatatt gtggcgatca gtctcggcgt   1620

tggcatgact ccgacgctct ctcacgattt cttttctaag ttaccggccg tactgcaacc   1680

gctgctacat agcggcatta tgctcgcaac ccttagcgcc gttgtgctga acgtcttctt   1740

taatggctat cagcatcatg ctgacctggt gaaggaatcc gtctctgata aagatttaga   1800

agtcaggaca gtacgtatgt ggcttctgat gcgcaagctg aagaaaaatg agcatggaga   1860

ataaaaaaaa aaaccccgcc cctgacaggg cggggttttt tttttgccgt tttcatcata   1920

tttaatcagc gactgatcca cccagtccca gaccggccgc                         1960
```

```
<210> SEQ ID NO 22
<211> LENGTH: 11378
<212> TYPE: DNA
<213> ORGANISM: Artificial Sequence
<220> FEATURE:
<223> OTHER INFORMATION: synthetic construct / Exemplary Bacteroides
      transformation vector

<400> SEQUENCE: 22
```

```
ggagagctgt atgtggggtg gaagaagcta tcgtaaaaat gctggagcag cttgatcctc     60

attctaccta ttctgatccg gaggaagtga agagaatgaa cgagccgttg cagggaaact    120

tcgaaggtat cggtatacag tttaatatgg cggaggacac tttgctggtg atacagcctg    180

tatcgggcgg accgtccgaa aaagtcggta ttctggccgg tgatcgtatc gtcatggtgg    240

aagatacgct gatagccggt gtaaagatga gtaccgagga tattatgcgt cgcctccgtg    300

gtcctaaaga ttcaaaagtg aatctgaaaa tacttcgccg aggggtgaag gaactgctcc    360

cctttacggt gaaaagggat aaaaccgttt tgccgccact acccatgagg agttcaagaa    420

agcgctgacc gggttgcaga agaaaggaat gaaagacttg attcttgatt tgcagggcaa    480

tggcgggggg tatttgaatg ctgctatcga tattgccaat gaatttttgg gtaaaaagga    540

actgattgtc tatacggagg gccgtcgtaa tcctcgtagc gagtttttttg ccaaaggtac    600

gggcgagttt cagaacggtc gtctgatggt attggttgat gaattttcgg cttctgccag    660
```

```
tgagattgtg accggagctg ttcaggattg ggacagaggc gttgtggtag gccgtcgcag    720
ttttggtaaa ggcttggtgc agcgtcccat tgatttgccg gacggttcga tgatccgtct    780
gacggtggcc cgctattata cgcctgccgg acgttgtatc cagaaacctt acgagagcat    840
tgaaaagtat aatgaagacc tgatagaccg ttataataaa ggagaaatga tgagtgaaga    900
cagcatccac tttccggatt cactgaagtt caagactcat aggttggccc gtacggtata    960
tggtggcgga gggatcatgc ccgattattt tgtgccgatt gatacgactc tctatactaa   1020
ataccatcgt cagttgcgtg ataaaggagc attgatgaaa gctcatttcc attttattga   1080
tgcccatcgt aaagaatggc tgggcaaata caagactttc aatgagttct acaaacgttt   1140
tgaagtgact ccggatatgt tgacacaact ggttgctacc ggcaaggaga tgggagtgga   1200
atataatgaa gaagagtatc aaaaggccct gcctctgctg aggttgcaga tgaaagcatt   1260
gatagcccgt gatttatggg atatgaatga atattatcac gtcattaatg acgcgaatga   1320
aagtatcagg aaagcgctgg aactgttgga gcaaccggac tttgaggggc tgctgttgaa   1380
aaagcgatag tcaagacttt atattaactg caggggcgca tagttgcact cctgcagttg   1440
tctgaaaaac ttgtaggata aaacgaaagg ctcagtcgaa agactgggcc tttcgtttta   1500
caattgggct acctttttt tgttttgttt gcaatggtta atctattgtt aaaatttaaa   1560
gtttcacttg aactttcaaa taatgttctt atatttgcag tgtcgaaaga aacaaagtag   1620
cctggcatct taatcaattt taaactcacc aaatcaaaat atgaaaaaaa aaaataataa   1680
aatgaagctc accttgaaaa aaaatgcgta cggaaagaat gccgtgaacc tgtcaaaaat   1740
cattcggcac cctaactacc atgaattcag acagatctcc gtcaacgtat cgctggaagg   1800
agactttgaa acggcccaca cgctcggcga caattcaaaa atagtaccta ccgatacgca   1860
gaaaaacacg gtgtatgcgc tggccaaaga gcattttgtg gattctatcg aaaatttcgg   1920
cctctattta gccaattatt ttatcaccaa taatccgcag gtatcgcagg ccaccgtcca   1980
tattatcgag catccctggg ctcgcatggc cttcgatgga gagccgcatc atcatgccta   2040
tgtgggtggc ggttctgaaa aacggacaac aaccttagta cagactaccg aagcaattcg   2100
tgtgacctcg ggcatcaaag atctgctgat tctaaaaaca accgattcgg gatttgaggg   2160
ctacgtcaaa gaccaataca caaccctgaa agaaacggcc gaccgcattt tcgcgaccca   2220
atgcgaggcc aactgggtgt acacttccca caaccttgac tttacgagtc tgttcggcaa   2280
aatccgcgaa acgctactaa aaaccttcgc gcatcacaag agtctgtcgg tgcagcaaac   2340
gttgctggct atgggatcgg ccgtcttgga agagaatcag gaagtaagcg aaataagcct   2400
gatcatgccc aacaaacatc acatcccgtt taacctggaa cagttcggca tggacaacca   2460
aaacgagatt ttcatagcca ccgacgagcc gtacgggtac attacgggaa cggtgacgag   2520
ggagtaaaaa ttataaataa attaataaac ttttattaaa aaaaaattac aaaatgagcg   2580
aacccgttaa cgcgcaatct acccgtctcg tttacggtct ggaagacaag gttcctttgg   2640
ttccggcgct tttagtgagt ttacaacagg ttggggctat ggtggtcggc accatcacac   2700
cagcgctgat attgtcgggt atccttcact ttgacccaca ggataccgct tatttagtaa   2760
gcatggcgtt ggtagcgtcg gcactgggta cgtttttgca aacgatgcgg ctcggtttca   2820
ttggctctgg cttactgagc atcacgggta ccagcttcgc ttttttggca ccgcttattc   2880
aggcgggtgt aacgggcggc ttgccgctta tggtcggtat gtcgctggca ggaacgccgg   2940
tacagctggc attagcccct tttctgccca aactaaaacg agtcttcaca cccttagttt   3000
cgggaattgt ggtgttgcta atcggccttt cattgattcc gacgggtatg cgaagtattg   3060
```

```
cccaattgcc ggccgaaggt gccccggcct ggagtggtgg tctggttgcc ctgattgtca   3120
ttgtggtcat gatcattgct caatcgattg gcaaagcctg ggctcgaatg gctgctgtac   3180
tcgttggcgt ggttacgggt tatacgattt gtggactcat gggttggctt caatctcctg   3240
ctccgagcaa tggttcctgg ctcacccttc cgcagctgtt tccatatggc ttggccttta   3300
aatgggaatt actgtttcca ttcgcgttta tatacctcgt ttgcgtgctg gaagcgatgg   3360
gcgatattac agccacctct caactgtcag gcttaccgac cgatggccct gaccattggg   3420
ctcgaattcg tgggggtatc ctagccgacg gactgacctg cattggatcg acgttgattg   3480
gtggctttcc gagtgctacc tacgcccaga acaacggggt gattcaaatg acaggagttg   3540
cggctcgccg aatcggctgg atcatggcgg ttattctact atgtctgggc ctctttccac   3600
cagttgggcg ctggattacc gtaatgccat cctgtgtact cggcgcgctg gctatcatgc   3660
tttttggctt agtggccgtt tcgggacttc gcctgatggt atctggcggg ttatcgcaac   3720
gggatgcgct gattgctgcg atttctttag gcgttggcat tggggttcca tcgcaggagg   3780
agtggttaaa aacgcttccc accgttgtgc agacgttcct ggaatcgggc gtttcggcag   3840
gtggattagc ggccttactg ctcaatctgt tactaccagc agaaggacga aagaagatga   3900
tgggaaaaga acctgccgaa atgttataga ataatgaata atgaataatg aataatgaat   3960
aatgaataat gaataatgaa taatgaataa tgaataatga ataatgaata atgaataatg   4020
aataatgaat aatgaataat gaataatgaa taatgaataa tgaataatgt accagacaat   4080
cgttcattgt tatctggatg acctatttat ttgctagtgc cgttagggtt cctagctgat   4140
tagaaggcca tcctgacgga tggccttttt tttgactctg ttgtgtcttc ttttaggtgt   4200
ggaataattt tccaaccatc actttatctg tctcccgaac agcaccttat tcagccatcg   4260
gttcacatac acgttcacga aagcacatcc tactccgata gcggctcctg ccactacatc   4320
actgggatag tgcacccctt ggttcatccg ggcaaaccct actccgcaag cccatacggc   4380
tgaaggggcg ataacatacc acttaggata agtgatggag agtgaggtgg ctaaagaaaa   4440
agctgccgca gtgtgtcctg aagggaatga cggactatcg gcatccggtg ctccgtatgc   4500
atgaatctta tccggatact ttacaaaagg ccggtcacga cctattatat gtttggcggc   4560
gtatgtaatc cccactgctt caatcacact ggttcctatg taaatggcat ctttcagcat   4620
cggctggtct ttctttatca atgcatagag tcccatggct gtaggtattc ctacgggtag   4680
aatcactccg ctagcggaca atccgcggct cagtccgtgt acatcccatc ggttgatggt   4740
tttcaacgtg ttgatgtcta tattctgtgc gctgaggctg aatgtaaaac aggctgtcag   4800
tataagaaaa ataatccttt ggcgtttcat ttagtttggc atttgttcag tgcaaagata   4860
ggaaaataat gtaattcgca tttacccttc cccgaattaa agaataattt ccataattcc   4920
ttgtattatc gctagaattc ctttactttt gcatcgtgaa tacacagctt ttaacagaat   4980
ttttagttct aacaattaaa taatttaaat tcaatcattt atgtggttaa gtaattcatc   5040
tattggaagg aaagtggtga tgagtgtcac aggtatcgcc cttgtcctgt ttctgacgtt   5100
tcacatggcg atgaaccttg ttgcgctctt ctcggaagat gcttacaaca tgatttgtga   5160
attcttggga gctaactggt acgcgttggt tgcaactgcc gggctggctg ctctgtttgt   5220
aattcacatc atctacgctt tctggttgac catgcagaac cgtgcagctc gcggtagcga   5280
acgttatgca gtgaacgtta aacctaaaac tgtggaatgg gcatctcaga acatgcttgt   5340
cctgggtatt gtcgttattg ccggattggc tcttcatttt gccaatttct ggtacaaaat   5400
```

```
gcagtttgcc gaaattatcg gtgttcatga tttgggcgca ttcggtccta cagacggtgc   5460
cgcttacatt cgtgaaacat tcggatgccc tgtatttaca gtgctttacc tcatttggtt   5520
agcagctttg tggttccacc tgactcacgg attctggagt gctttgcaga ctttgggctg   5580
gagcaataaa atctggttcg agcgttggaa gactattggt aacatctact ctactttggt   5640
agttcttggt tttgcagcag tagtcgttat ctacttcgct atgactggcg cgcctgatag   5700
gtgggctgcc cttcctggtt ggcttggttt catcagccat ccgcttgccc tcatctgtta   5760
cgccggcggt agccggccag cctcgcagag caggattccc gttgagcacc gccaggtgcg   5820
aataagggac agtgaagaag gaacacccgc tcgcgggtgg gcctacttca cctatcctgc   5880
ccggctgacg ccgttggata caccaaggaa agtctacacg aaccctttgg caaaatcctg   5940
tatatcgtgc gaaaaaggat ggatataccg aaaaaatcgc tataatgacc ccgaagcagg   6000
gttatgcagc ggaaaagcgg gattaaaagt cggggattgg tgaacaaaaa ggtgtttctc   6060
tctttaagag aaatatcgtt ttgctaaaca gttgatattg aggtatcatt ttatcgtaaa   6120
agacattttt gctcaacaat tgcttgacgg aaatcaacaa attttagcat tttgtaaaaa   6180
agtcgctata taatttggtg aattggagtt attttcatat ttttgcatcc cgaagagttt   6240
ctcttaaaga gagaaacatc ttttgcatac cttttccgac cgaattttta tgtcgtaaag   6300
aggggctttg caggggggtgg actcagaaag atgagaatag atgactattg tagttgaaac   6360
acatagaaag ttgctgatat acagaccgat acgcatatcg ggatgaacca tgagtacgtt   6420
cttttctcaa aaaacataaa tattcgaaaa gagatgcaat aaattaagga gaggttataa   6480
tgaacaaagt aaatataaaa gatagtcaaa atttattac ttcaaaatat cacatagaaa   6540
aaataatgaa ttgcataagt ttagatgaaa aagataacat ctttgaaata ggtgcaggga   6600
aaggtcattt tactgctgga ttggtaaaga gatgtaattt tgtaacggcg atagaaattg   6660
attctaaatt atgtgaggta actcgtaata agctcttaaa ttatcctaac tatcaaatag   6720
taaatgatga tatactgaaa tttacatttc ctagccacaa tccatataaa atatttggca   6780
gcatacctta caacataagc acaaatataa ttcgaaaaat tgtttttgaa agttcagcca   6840
caataagtta tttaatagtg gaatatggtt ttgctaaaat gttattagat acaaacagat   6900
cactagcatt gctgttaatg gcagaggtag atatttctat attagcaaaa attcctaggt   6960
attatttcca tccaaaacct aaagtggata gcacattaat tgtattaaaa agaaagccag   7020
caaaaatggc atttaaagag agaaaaaaat atgaaacttt tgtaatgaaa tgggttaaca   7080
aagagtacga aaaactgttt acaaaaaatc aatttaataa agctttaaaa catgcgagaa   7140
tatatgatat aaacaatatt agtttcgaac aatttgtatc gctatttaat agttataaaa   7200
tatttaacgg ctaaaaacaa taggccacat gcaactgtaa atgtttacgc gggtaccgac   7260
accgcggtgg aggggaattg tgttacaacc aattaaccaa ttctgattag aaaaactcat   7320
cgagcatcaa atgaaactgc aatttattca tatcaggatt atcaatacca tatttttgaa   7380
aaagccgttt ctgtaatgaa ggagaaaact caccgaggca gttccatagg atggcaagat   7440
cctggtatcg gtctgcgatt ccgactcgtc caacatcaat acaacctatt aatttcccct   7500
cgtcaaaaat aaggttatca agtgagaaat caccatgagt gacgactgaa tccggtgaga   7560
atggcaaaag cttatgcatt tctttccaga cttgttcaac aggccagcca ttacgctcgt   7620
catcaaaatc actcgcatca accaaaccgt tattcattcg tgattgcgcc tgagcgaggc   7680
gaaatacgcg atcgctgtta aaaggacaat tacaaacagg aatcgaatgc aaccggcgca   7740
ggaacactgc cagcgcatca acaatatttt cacctgaatc aggatattct tctaatacct   7800
```

```
ggaatgctgt tttcccgggg atcgcagtgg tgagtaacca tgcatcatca ggagtacgga   7860
taaaatgctt gatggtcgga agaggcataa attccgtcag ccagtttagt ctgaccatct   7920
catctgtaac atcattggca acgctacctt tgccatgttt cagaaacaac tctggcgcat   7980
cgggcttccc atacaatcga tagattgtcg cacctgattg cccgacatta tcgcgagccc   8040
atttataccc atataaatca gcatccatgt tggaatttaa tcgcggcctg gagcaagacg   8100
tttcccgttg aatatggctc ataacacccc ttgtattact gtttatgtaa gcagacagtt   8160
ttattgttca tgatgatata tttttatctt gtgcaatgta acatcagaga ttttgagaca   8220
caacgtggct ttgttgaata aatcgaactt ttgctgagtt gaaggatcag agcctacgtt   8280
ccgaatacgg tcaaaaaaaa ggccatccgt caggatggcc ttcgcattaa tatgccgctt   8340
cgaattcttt taggaagcgt gtatcgtttt cagagaacat acggaggtct ttcacctgat   8400
atttcaggtt tgtgatacgc tcgataccca taccgagtcc ataaccgctg tatattttgc   8460
tgtctatacc atttgattca agtacgttcg ggtctaccat accgcaaccg aggatttcta   8520
cccagccggt gtgtttacag aacggacatc ctttaccgcc gcagatatta cagctgatat   8580
ccatttccgc acttggttca gcaaacggga agtaagacgg acgcagacgg atctttgtat   8640
cagcaccgaa catttctttg gcaaagagca gcaatacctg cttcaagtcg gtgaatgata   8700
cgtttttatc tacatacagc gcttctacct gatggaagaa acagtgtgcg cgatagctga   8760
tagcttcgtt acgatataca cgtcccggac agatgatgcg gataggaggc tgtgaagttt   8820
ccatcacacg agtctgtaca gaagaagtat gtgtacgcaa tactacgtcc gggtgagctt   8880
cgataaagaa agtgtcctgc atatcgcgtg ccggatgatc ttcggcaaag ttcagtgccg   8940
agaacacgtg ccagtcatct tcaatttccg gaccttcggc aatgctgaat cccagacggg   9000
caaagatatc aatgatttcg ttctttacaa tggtgagcgg gtggcgtgta ccgagttcta   9060
caggataagc cgaacgcgtc aaatccagtc cgtcacaatc gttgtcctga ctttcaaaca   9120
tttctttcag cgcgttgatt ttgtcctgcg cttttgtttt cagttcattc agtctcatgc   9180
cgacttcttt tttctgttcg gcagctacat tacggaaatc tgccattaag tcgttaatgg   9240
ctcccttctt acttaggtat ttgatgcgga gagcttcgag ttcttcggca ttggaggcgt   9300
gtaaggcttc cacctctttc agaagttgtt caatcttagc tatcattttt taatattttt   9360
agcggccccg ttaaacaaaa ttatttgtag aggctgtttc gtcctcacgg actcatcaga   9420
ccggaaagca catccggtga cagctcaggc tactttgttt ctttcgacac tgcaaatata   9480
agaacattat ttgaaagttc aagtgaaact ttaaatttta acaatagatt aaccattgca   9540
aacaaaacaa aaaaaaggta gcccaattgt aaaacgaaag gcccagtctt tcgactgagc   9600
ctttcgtttt atcctacagt cgctcggcga tcgaaggctt cggaaaaaaa aggccatccg   9660
tcaggatggc cttcgcatta atatgccgct tcgaattctt ttaggaagcg tgtatcgttt   9720
tcagagaaca tacggaggtc tttcacctga tatttcaggt ttgtgatacg ctcgataccc   9780
ataccgagtc cataaccgct gtatattttg ctgtctatac catttgattc aagtacgttc   9840
gggtctacca taccgcaacc gaggatttct acccagccgg tgtgtttaca gaacggacat   9900
cctttaccgc cgcagatatt acagctgata tccatttccg cacttggttc agcaaacggg   9960
aagtaagacg gacgcagacg gatctttgta tcagcaccga acatttcttt ggcaaagagc  10020
agcaatacct gcttcaagtc ggtgaatgat acgtttttat ctacatacag cgcttctacc  10080
tgatggaaga aacagtgtgc gcgatagctg atagcttcgt tacgatatac acgtcccgga  10140
```

```
cagatgatgc ggataggagg ctgtgaagtt tccatcacac gagtctgtac agaagaagta  10200
tgtgtacgca atactacgtc cgggtgagct tcgataaaga aagtgtcctg catatcgcgt  10260
gccggatgat cttcggcaaa gttcagtgcc gagaacacgt gccagtcatc ttcaatttcc  10320
ggaccttcgg caatgctgaa tcccagacgg gcaaagatat caatgatttc gttctttaca  10380
atggtgagcg ggtggcgtgt accgagttct acaggataag ccgaacgcgt caaatccagt  10440
ccgtcacaat cgttgtcctg actttcaaac atttctttca gcgcgttgat tttgtcctgc  10500
gcttttgttt tcagttcatt cagtctcatg ccgacttctt ttttctgttc ggcagctaca  10560
ttacggaaat ctgccattaa gtcgttaatg gctcccttct tacttaggta tttgatgcgg  10620
agagcttcga gttcttcggc attggaggcg tgtaaggctt ccacctcttt cagaagttgt  10680
tcaatcttag ctatcatttt ttaatatttt tagcggcccc gttaaacaaa attatttgta  10740
gaggctgttt cgtcctcacg gactcatcag accggaaagc acatccggtg acagctcagg  10800
ctactttgtt tctttcgaca ctgcaaatat aagaacatta tttgaaagtt caagtgaaac  10860
tttaaatttt aacaatagat taaccattgc aaacaaaaca aaaaaaaggt agcccaattg  10920
taaaacgaaa ggcccagtct ttcgactgag cctttcgttt tatcctagga tcagctgtac  10980
gtactcgcag ttcaacctgt tgatagtacg tactaagctc tcatgtttca cgtactaagc  11040
tctcatgttt aacgtactaa gctctcatgt ttaacgaact aaaccctcat ggctaacgta  11100
ctaagctctc atggctaacg tactaagctc tcatgtttca cgtactaagc tctcatgttt  11160
gaacaataaa attaatataa atcagcaact taaatagcct ctaaggtttt aagttttata  11220
agaaaaaaaa gaatatataa ggcttttaaa gcttttaagg tttaacggtt gtggacaaca  11280
agccagggat gtaacgcact gagaagccct tagagcctct caaagcaatt ttgagtgaca  11340
caggaacact taacggctga catggggcgg ccgcgtag                          11378
```

<210> SEQ ID NO 23
<211> LENGTH: 6047
<212> TYPE: DNA
<213> ORGANISM: Artificial Sequence
<220> FEATURE:
<223> OTHER INFORMATION: synthetic construct / Exemplary Bacillus transformation vector

<400> SEQUENCE: 23

```
ggatccacaa tgatcattca tacgaagtac catggccaaa tgaacataaa agaagaacaa     60
atcattcttt ttgaaagcgg gattccaggc tttttagaag aaaaacagtt cgtcatactt    120
ccgctttcag aagactctcc attcgtggca ctgcagtccg tcacttcaga aaatcttgcg    180
tttatcgtcg taagtccgtt tatctttttt aagaattatg aatttgatct tgatgaatca    240
actgctgaac ttttggatat cgataatatt caagacgtag aagtcatgac aatattgact    300
atggcagagc catttgaaaa gtctactgcg aatttattgg ctcccattat tgtgaatcgc    360
aagaacatga tggctaagca agtcgtttta cacgactcct catatacgac aaagcatccg    420
attggaggag aatcatgcta gttttatcgc ggaaaataaa cgaagcgatt caaataggtg    480
ctgatattga agtaaaagtg attgcggttg aaggggatca agtgaagctt ggaattgacg    540
ccccaaagca tattgatatt cacaggaaag aaatttactt gaccattcag gaagaaaata    600
accgtgcagc agcgttatcc agcgatgtga tctccgcatt atcctcacaa aaaaagtgag    660
gattttttta tttttgtatt aacaaaatca gagacaatcc gatattaatg atgtagccgg    720
gaggaggcgc aaaagactca gccagttaca aaataagggc acaagaacgt gccttaacaa    780
```

```
catattcagg gaggaacaaa acaatgatgt atgcaggtgc gattttggtg cccctgcttg    840

tcggcagggc gctgaatgta acaactgaac agctgtccta cctattggcg attgacctgt    900

taacatgcgg cgtcgctacg cttttgcaaa ccttgcgcgg aacatacatc ggcatcgggc    960

ttcccgtcat gcttggcagt tcatttgtgg ccgtcacccc aatgattgca atcggcagca   1020

attacggcat tcacgcgatt tatggttcca tcattgcggc cggtgtgttc atctttttgt   1080

ttgcgcgttt tttcggcaag ctgactgtgt tatttcctcc tgtcgtaaca ggtaccgttg   1140

tgaccttgat cggcctttca cttgttccga caggtgtgaa aaatatggct ggcggcgaaa   1200

aaataaacgg cagcgccaac cccgaatacg gttcgctcga aaaccttctt ctctctgtcg   1260

gtgtccttgt tctgatctta gtcctcaacc gctttctcaa aggatttgcc cgaacactgt   1320

ccgttctgat cggcatcgcc gccggaacag cggcagcagc gatcatgggc aaagtcagct   1380

tttcttctgt tacagaagca ccgttcttcc aaatcccgaa gcctttttac ttcggagccc   1440

ctgcgtttga aatcggtccg atcttaacga tgctgatcgt cggaatcgtc attattgtgg   1500

aatcaaccgg cgtttttttac gcaatcggaa agatatgcgg cagaccttta actgacaaag   1560

atctcgtcaa aggctatcga gcggaaggaa tcgccattct catcggcggg ctgttcaatg   1620

cctttcctta taatacctttt gcgcaaaacg ccggcttatt gcagctgacc aaagtgaaaa   1680

caagaaacat cgtcgttacc gcaggctgta tccttgtctg tctcggactg attccgaaga   1740

ttgccgccct tgcatctgcc gttcctgctg ctgtacttgg cggcgcgacc gtcgtcatgt   1800

tcggcatggt gattgcctcc ggcgtcaaaa tgctcagcac agcggatctc aaaaatcaat   1860

accacctcct gaccatcgca tgctcaatcg cactcggcat cggcgccagc acggcccccg   1920

ggatttttgc tgaattcccc gctccgatcc ggattctggt cagtgacggc accatcaccg   1980

gaagcctaac cgccatcttt ttgaatctat ttttcagctt gcgcgacaaa aaagaattaa   2040

cagcacagca aacagaactt ccggtattag aacatacact cgcattagaa aaagaggtgt   2100

aaaaaagatg aaggaacagc acaatgcctt acagctaatg atgctggggc ttcagcacat   2160

gcttgccatg tatgcgggag ccattctcgt tccgttgatc gtcggagcag cgatcgggct   2220

gaatgcgggg cagctgacgt atttaatcgc gattgatttg tttatgtgcg gggcggcaac   2280

tcttttgcag ctctggagaa accgatattt cggcatcggc cttcccgttg tgctcggatg   2340

cacgtttacc gcagtcggcc cgatgatttc catcggaagc acttacggtg tcccagcgat   2400

atatggtgcc attatcgccg caggactgat tgtcgtctta gccgcgggct tcttcgggaa   2460

gcttgtccgt ttttttccgc ctgtcgtaac cggatcagtc gtcatgatca tcggcatcag   2520

cctgattcca acggcaatga ataacctggc cggaggtgaa ggaagcaaag aattcggctc   2580

actcgacaac gtgctcctcg ggtttggcgt cacagctttt atcttattgc tgttttattt   2640

ctttaaaggc tttatccgct ccatagcgat tttactcggt cttatcgcag gaacagcggc   2700

tgcatatttc atgggaaagg tcgatttttc tgaggttttg gaggcgtctt ggcttcatgt   2760

tccgtctctg ttttatttcg gaccgccaac ctttgagctg ccggctgttg tcacgatgct   2820

tctcgttgca attgtcagcc tcgttgaatc gacaggcgtt tattttgccc tcgctgatat   2880

cacaaaccgc aggctgtcgg agaaggatct ggaaaaaggc taccgggcag aaggccttgc   2940

gattttgctg ggcggcttat ttaacgcgtt tccctataca gctttctcgc agaatgtcgg   3000

catcgttcag ctctcaaaga tgaaaagtgt caacgtcatc gccatcacag gaatcatact   3060

ggtcgcgatc gggctggttc caaaagcagc ggccctgaca acagtgatcc ccaccccagt   3120

tctcggcggc gcaatgatcg tcatgttcgg catggtcatt tcttacggga tcaaaatgct   3180
```

```
atccagcgtt gaccttgatt cgcaaggcaa cctgctgatt atcgcctctt ccgtcagctt   3240
ggggcttggc gctacaacag ttcccgcgtt gttttcatct ctttcgggcg cggcctctgt   3300
cttggcagga agcggaattg tgatcggcag tttgacggcc attgcactgc acgctttttt   3360
tcaaaccaaa cagccgaata gcgcagacat aaaaacgtaa aggaagatgc caatgttcac   3420
aatggatgac ctgaaccaaa tggacacaca aacactgaca gacacacttg gctctatttt   3480
tgaacactct tcatggattg cggagagatc cgcagcacta cggccgtttt cgtccctttc   3540
tgatcttcac cgcaaaatga ctggcattgt aaaagctgcg gatcgcgaga cacagcttga   3600
tttaatcaaa aagcatcccc ggctcggaac aaagaaaaca atgagcgatg actcggtacg   3660
agagcagcag aacgcagggc tcggcaaatt agaacagcag gaatacgagg agtttctcat   3720
gctgaatgaa cactattatg atcgcttcgg ctttcctttt attttagcgg tgaagggaaa   3780
gacgaaacag gacattcacc aagccctgct ggcaaggctt gagagcgaac gagaaacgga   3840
gttccagcag gcccttatag aaatttaccg aatcgcccgc tttcgtctgg ctgacatcat   3900
cactgaaaaa ggagagacgc aaatgaaaag aaccatgtct tatggcaaag gaaatgtatt   3960
tgcataccga acgtatttaa aaccgctcac tggagtgaag caaatcccgg aatcatcttt   4020
tgccggaaga gataataccg ttgtcggcgt tgatgtgaca tgcgaaattg gcggagaagc   4080
cttcctgcca tcatttacag acggagacaa cactctcgtc gtggcaacgg attcaatgaa   4140
aaactttatc cagcgccatc tcgcatccta tgaaggaacg acaaccgagg ggttcctaca   4200
ctatgtagct caccgatttt tagataccta ttctcatatg gacacgatca ctctgactgg   4260
cgaagacatt ccgtttgaag caatgcctgc atacgaggag aaagagctca gcacaagccg   4320
cctcgtcttc agaagatcgc gtaatgaacg aagccgctct gtgctgaaag cagaacgaag   4380
cgggaatacc ataacgatta cagagcaata cagcgaaatc atggatcttc agctcgtcaa   4440
ggtgagcggc aactccttcg tcggcttcat ccgggacgaa tatacgactc tcccggaaga   4500
cggcaaccgc ccgctgtttg tctatttaaa catcagctgg caatatgaaa atacaaatga   4560
ctcatacgct tctgatccag cacgctacgt tgcggctgaa caagtccgcg acttagcgag   4620
caccgttttt cacgagctcg aaaccccttc aatccaaaac ctaatctatc atatcggctg   4680
cagaatatta gcgaggttcc cgcagctcac tgatgtcagc ttccaatctc aaaatcacac   4740
gtgggatacg gttgtcgaag aaatcccggg ctcaaaagga aaagtctaca ccgaaccgcg   4800
cccgccatac ggtttccaac attttaccgt gacaagagaa gacgccgaga aagaaaaaca   4860
gaaagccgct gaaaaatgtc ggagcctgaa agcctgatgg gaaaactgac aacccatatt   4920
ttagatttaa cctgcggcaa accagcggcg aacgtaaaaa ttggattgaa gcggctgggc   4980
gaaagtatta tgaaagaggt atacactaac aatgacggca gggtcgatgt ccctctgctg   5040
gctggtgaag agctgatgtc aggagagtat gtgatggaat ttcatgcagg agactatttt   5100
gcgagtaaaa acatgaacgc agccgatcag ccgtttttaa ccatcgtcac cgtccgtttt   5160
cagctagcag atccagatgc acattatcat atcccgctct tgctgtcgcc gtttggttat   5220
caggtgtata gggggagtta ataattttaa aaaagacctt ggcgttgcca gggtctttta   5280
atttaaattt ctatctccta atcattcctc atcctgtcac taactcatga tataataacc   5340
ggattctcca ctaacttttt ataaatgtat ttccatacaa gaaatctaaa acagaagatt   5400
tttttccaaa aatatgtgta atcttatctc gacttagtcg atataaacga tagattgggg   5460
catagggat gatcaattga acattgaaag gctcactacg ttacaacctg tttgggatcg   5520
```

```
ttatgatact caaatacata atcagaaaga taatgataac gaggttcctg ttcatcaagt   5580

ttcatatacc aatcttgctg aaatggtggg ggaaatgaac aagcttttgg aaccttcgca   5640

agttcatctg aagttcgagc ttcatgacaa gttaaatgaa tactatgtaa aggtaataga   5700

ggactctaca aatgaagtga tccgcgaaat tccaccaaaa cggtggcttg atttttatgc   5760

ggctatgact gaatttcttg ggttatttgt agatgaaaaa aagtagaata ggagtggttt   5820

gagatggtca caagaataac aggtctggcg tcaggaatgg atatagatga tatcgtatca   5880

aagctgatgc agacagaaag agcgccgctt gataagctga cacaaaaaaa gcagactctt   5940

gaatggcagc gtgacagcta tcgtgaagta aactcaaaaa taaaagaatt gcaagattat   6000

atgtctaaaa atacgttgac atatccgagc acgtatcaga gggatcc                 6047
```

<210> SEQ ID NO 24
<211> LENGTH: 8128
<212> TYPE: DNA
<213> ORGANISM: Artificial Sequence
<220> FEATURE:
<223> OTHER INFORMATION: synthetic construct / Exemplary Kluyveromyces transformation vector

<400> SEQUENCE: 24

```
ggcgcgccga aagtgattga agaaccctca aacttgctgg atatttcctt acccttgacc     60

tttaggcttt caattttacc caacaatttg tccaagacaa attgcaatcc actggattca    120

actgagacat aacgtttacc gtcgttgatc ttggtaggtt tttctgctgt ctctgtaaca    180

aaatctggta cctttaatgg aagttcggct tggccccagg caatttcatg acctgccttt    240

agaacaccag catcatcctt taacacggca acaacataag tggtatcaga aggaatagta    300

acagattctt ctggctttaa agctggaacg tcgattgtct ttcccgtgtc cttgtcgata    360

aacaataagt gatctgtcgt aatgaagtcg tgcttatttg tgattgttac agatccgtgc    420

gcaattttaa tatgaacggg ttcaataacc ttcttatact ctacaaggcc cggagtagga    480

ttatgctcac tgttacacaa accatccatg atgaacactc cgtcatgaac ctcttcctta    540

aagtcaccac cataagcata agctttatgc aacttaccat ctgcagtact aacatcttcg    600

aattcaatac cgtgatttgc ccattcccag ataaagccac cttggtaaaa cttctccttg    660

tagaacaact cttgatattc tttcaaagaa cccgggccgt tacccattgc atgaccgtac    720

tcacacaaga tcaaaggctt ttcaaactta ccattttcat cagtgtggtt cttcctccac    780

ctttccataa tttcaaatgt tgggtacatg aaactaaaga tatctgcact caaagcgttc    840

aagtcaccct cataatgcac cagtctggta ggatccaatt gcttaagcca gtcacgtgtg    900

aaacacgtga ctatacttac cctcacatta ccctcactct ttcacattac cctccccacc    960

atatcttccc cccccagctt cctgtcttcc actatccctg caaccaccac caccacacaa   1020

caaacagccc caaacaaccc ccaacagccc ggaaaaatcc acgcctcctc ccgaacacac   1080

gaagcccgcc ccggcttcca ctccaacact gccaacactg gaaccccgca ccacgtaacc   1140

acccacttta gtggctgccc gcccctcctg cgcttccctt gcgcttccct tgggaccaca   1200

ctccggtggc atggccctcg cttgctacat gctacctttt ttttgccctt ttctggcctt   1260

ttctggcttt tctggcctca ccacagtgta gtggtgtacc acagtgtaat ggtgtaacat   1320

tgtcgaatgg tattgtagcc tgttgtagcc tgttgtagcc tgttgtagcc tggtgtaatg   1380

tctggcatag tctggtgtct ggtgtctggt gtcttttgga aactgaacag tggaaagtgg   1440

aagtgaaaaa ttgtataaat ataggtgtcc cattcgtggt ttggtggatg tgtccttgac   1500
```

```
attgcaggtt tctctctgtt tcattgtgtt aagacttgtt aagacttgat aagtatttcc   1560
ctagtaatac cccaccaacc atcggttgat acattttaat acacactacc tatataaaga   1620
tacaaaatgg acaactccat ccattcaacc gacggccccg actccgtcat ccccaactcc   1680
aaccccaaga agaccgtccg acagagagtc cgcttgctgg ctaggcatct gacgacccgc   1740
gagggcctga tcggcgacta tgactatggc ttccttttcc ggcccgagct acccttcatg   1800
aagaaagatc cacgggcgcc gcctttttttt ggcctcaacg agaagattcc cgtgctgttg   1860
gcgtttatcc tgggtcttca gcatgcgctt gccatgttgg cgggtgtggt cactcctcct   1920
ctgatcatat caagctcgct gagcctgccg tccgatctcc agcagtatct cgtttcgacc   1980
tcgcttatcg tctgcgggct gctgtcgatg gtccagataa cgcgatttca tatctacaag   2040
acaccgtact atatcggcag tggcgtcctc tcagttatgg gggtctcgtt ctccatcatc   2100
tccgtcgcca gcggcgcctt caaccagatg tactcgaacg ggttctgtca actcgacgag   2160
gctggaaaca gactcccttg ccccgaagcg tacggcgcct tgattggcac ctcggcctgc   2220
tgtgctttgg tggagatcct cctcgctttc gtgcctccca aagtgataca gaaaatcttc   2280
ccgcccatcg tcactggtcc cactgtaatg cttatcggga taagtctgat tggaactggg   2340
ttcaaagact gggctggcgg ctcggcgtgt atggatgacg ggatgctgtg cccgtccgca   2400
actgcaccgc gccctctccc gtgggggagt ccagagttca tcggcctggg ttttctagtc   2460
tttgtatcga tcatcctctg cgaacgattt ggagccccga ttatgaagtc ctgttctgtt   2520
gtcatcgggc tgctcgtcgg ttgtatagtc gctgcagcct gcggctactt cagccacgcc   2580
gatattgacg ctgcccctgc cgcctcattc atctgggtca agactttccc tctctctgtc   2640
tatggtccga tggttctccc gatcatcgcg gttttcatca tctgcgcctg cgagtgcatc   2700
ggtgatgtaa ccgccacctg cgacgtctcg cgtctcgaag tccgcggcgg cacattcgag   2760
tcgcgcatcc agggcgccgt cctagcagac gggatcaact cggtagtcgc tgcccttgcg   2820
acaatgaccc ccatgacgac ctttgcgcag aacaacggcg tgattgccct cactcgctgc   2880
gcaaaccgct gggccggata ctgctgctgt ctgatattga tagtagccgg tatctttgct   2940
aaattcgctg cagccattgt tgccataccc aacagtgtca tgggcgggat gaagacgttt   3000
ctcttcgctt cggtcgttat tagcggacag gcgatcgtgg ccaaggcgcc gttcacaagg   3060
cgaaatcggt ttatcctcac cgcgtcaatg gccctgggat acggggcgac gctggtgccc   3120
acttggtttg ggaatgtatt ccctcagacc gagaatagag acctggaggg gtttgaaaat   3180
gcgatcgagc tcgtgcttga gacggggttt gcggtcacgg catttgttgc tatgctcttg   3240
aacgcaatca tgcctgctga agtcgaagag atcggtgccg tcacccctat gccggtctct   3300
gctcatgata atcgggatgg cgaggcggag tatcagagca agcaggctta gtctgatctg   3360
cttactttac taacgacaaa aaaaatcaaa aaaaaaaaaa aaacaatcag tccttctctt   3420
cttacgatat gatatgatta aatgatgcta tgaaatcatc ttcttcttaa ctttcttaaa   3480
tcttacacgt cacttactct atatacccgt ttagctttgc ctggtcacag cgacatttta   3540
tataagtgta cgtattttct tttttttttt aaaaaatttc tattctaacc ttagaaaggt   3600
gtccagcgaa tatacagcgt gaataatgga atggccttgt attcgttttt tccgagagaa   3660
aaaaacgggc ttcggtgaaa atcgggtgaa tatgcaacta gcgggacgaa tgctctggaa   3720
atgcatatcc tatgcaacta gcgggatgaa caaatctcac cccagaattc gcaggaaaaa   3780
acaggaaaaa aaaaaagaag gccaccacgg ccacaaagac cacaaagacc acaaaaaaaa   3840
acaaaaaaca accgtcccag cttccagtgt ttggaatact ggaacacagg aagccgcata   3900
```

```
agagtgggcg ttgcacagga agccaggccc agaagcccca gagttacttt tttttttttg   3960
tttttccctt ctgttcgctg tgcccgcatc agatgatgcg cctttattta cgatgccaat   4020
gcgaatagca ccagtgagag caccagtaaa agcatacgca tacacataca cacatagagc   4080
aagcaagcag gctagcaacc aggaaaggct gccagtgact gctactgggt gtctaagaac   4140
cgtagggcgg attattgttg cggtggttgg ttgcgggtgg ttatgcgatg gtacggtgca   4200
gaatcgtacg gtgttggtta tggaattagt atgggtatgt gatatgtggt aatatgtgat   4260
attgggttat tgtgatttgg aatactgaat atcgaatatg ggatatggaa tatggccatg   4320
gcatggtatg gtatgggatg ggagtattct attttatttt attttattct ggttcctgcg   4380
tttagggtag ggtaggaaga aggtgagtgc ttttgtatat aagtggagtg tctggatcag   4440
ttttgtggat tgtgaatgtt agtttcccct ttaatgtata tttgtattat ttgcttttga   4500
gtactcaata accaagcaca actactagtt ttaaaggatc catcctctta aacagtacaa   4560
atcgcaaaga aaagctccac acccaaacca aataattgca tgtcaacaac gctctcatca   4620
tccacttacg gcaaggacaa cgtcaagttc ctcaaggtca agaaagatcc gcagaaccca   4680
aagaagcagg aggttatgga ggccaccgtc acgtgtctgc ttgaaggtgg gttcgacacc   4740
tcgtacacgg aggctgacaa ctcgtccatc gtgccaacag acaccgtgaa gaacaccatt   4800
ctcgtgttgg caaagaccac ggagatttgg ccaattgaga gatttgcagc caagctggcc   4860
acgcactttg ttgagaagta ctcgcacgtc tctggcgtct ccgtcaagat tgtccaggac   4920
agatgggtca agtacgccgt tgacggcaag ccacacgacc actcttttat ccacgaaggt   4980
ggtgagaaga gaatcactga cctgtactac aagagatccg gtgattacaa gctgtcatct   5040
gccatcaagg acttgacggt gctgaagtcc accggctcga tgttctacgg ctacaacaag   5100
tgtgacttca ccaccttgca accaaccact gacagaatct tgtccaccga cgtcgatgcc   5160
acctgggttt gggataacaa gaagattggc actgtctacg acatcgccaa ggctgcagac   5220
aaggggatct ttgacaacgt ttacaaccag gctagagaga tcaccttgac caccttcgcc   5280
ctggagaact ctccatctgt gcaggccacg atgttcaaca tggctactca gatcttggaa   5340
aaggcatgct ctgtctactc ggtttcatac gccttgccaa acaagcacta cttcctcatt   5400
gacttgaaat ggaaaggttt ggagaacgac aacgagttgt tctacccatc tccacatcca   5460
aatggtttga tcaagtgtac tgttgtccgt aaggagaaga ccaagttgta agtgcatcat   5520
tgacctttct aatgaaacca cacgtgaatt aaaggaaagc gcgcagcagc agcagcagct   5580
tttctttcct tcttcaaatc atacctttc tctatttcaa cgttcttttc atttcaccat   5640
gaaatgagtt gaattgttgc tttgagttta cgacgataca taaatattaa ttaaaatacg   5700
aaaaatacac actacttatt cccttcgaga ttatatctag gaacccatca ggttggtgga   5760
agattacccg ttctaagact tttcagcttc ctctattgat gttacacctg gacacccctt   5820
ttctggcatc cagtttttaa tcttcagtgg catgtgagat tctccgaaat taattaaagc   5880
aatcacacaa ttctctcgga taccacctcg gttgaaactg acaggtggtt tgttacgcat   5940
gctaatgcaa aggagcctat atacctttgg ctcggctgct gtaacaggga atataaaggg   6000
cagcataatt taggagttta gtgaacttgc aacatttact attttccctt cttacgtaaa   6060
tatttttctt tttaattcta aatcaatctt tttcaatttt ttgtttgtat tcttttcttg   6120
cttaaatcta taactacaaa aaacacatac ataaactaaa agtgttgaca attaatcatc   6180
ggcatagtat atcggcatag tataatacga caaggtgagg aactaaacca tgggtaagga   6240
```

```
aaagactcac gtttcgaggc cgcgattaaa ttccaacatg gatgctgatt tatatgggta   6300

taaatgggct cgcgataatg tcgggcaatc aggtgcgaca atctatcgat tgtatgggaa   6360

gcccgatgcg ccagagttgt ttctgaaaca tggcaaaggt agcgttgcca atgatgttac   6420

agatgagatg gtcagactaa actggctgac ggaatttatg cctcttccga ccatcaagca   6480

ttttatccgt actcctgatg atgcatggtt actcaccact gcgatccccg gcaaaacagc   6540

attccaggta ttagaagaat atcctgattc aggtgaaaat attgttgatg cgctggcagt   6600

gttcctgcgc cggttgcatt cgattcctgt ttgtaattgt ccttttaaca gcgatcgcgt   6660

atttcgtctc gctcaggcgc aatcacgaat gaataacggt ttggttgatg cgagtgattt   6720

tgatgacgag cgtaatggct ggcctgttga acaagtctgg aaagaaatgc ataagctttt   6780

gccattctca ccggattcag tcgtcactca tggtgatttc tcacttgata accttatttt   6840

tgacgagggg aaattaatag gttgtattga tgttggacga gtcggaatcg cagaccgata   6900

ccaggatctt gccatcctat ggaactgcct cggtgagttt tctccttcat tacagaaacg   6960

gctttttcaa aaatatggta ttgataatcc tgatatgaat aaattgcagt ttcatttgat   7020

gctcgatgag tttttctaat cagtactgac aataaaaaga ttcttgtttt caagaacttg   7080

tcatttgtat agttttttta tattgtagtt gttctatttt aatcaaatgt tagcgtgatt   7140

tatatttttt ttcgcctcga catcatctgc ccagatgcga agttaagtgc gcagaaagta   7200

atatcatgcg tcaatcgtat gtgaatgctg gtcgctatac tgtgcttaat tagcttgtac   7260

atggctttgt ggtttctgcc ataacaagct tcgttaccca aggaccagat aataatcgaa   7320

ggatgattga catctcttag gacaagttgg gaagctctgt ctaagtacgc gacctcgtac   7380

tctggattat ctgataagta atgggcatta acatcgtaga gtttattttt ggtatctgga   7440

tattcagcct ccaagttcgt atgacgatta aatggctctt gaacaccgtg agtttcaaga   7500

tctgcctcat caatgaccca gaagcctagt ttatcgaaga ggtcatacac cttaggatgg   7560

tttggataat gcgagttacg aacagcattg atgttaaact tcttcattag aatcaagtct   7620

ctaacaacaa aatctaatgg cacagctcta ccgaaccttg gatggtgatc atgcctgttg   7680

acacctctaa agagaatgtc tttgccatta acagtaatgt taccgtcctt caactccact   7740

tgtctgaaac caacatggtg cttaatagat tgaatcacac tgccatcaga tccaattaaa   7800

tccaactggt acttgtacaa agtaggattt tctgcggtcc aatgttctgg ggccttgacg   7860

ttgatcttga aagctgtttc ttcgtccttt ttggtcgaaa aggaaataaa ttctttagtt   7920

gaaaacgtcg tgttcccatt ctcctcgttc aacaaagagc ttgcatcgta aactttagat   7980

ccatcttcag gttcgtaaag tgtgaaattg atgtgatcat aagaagaacc ctggacatca   8040

actttcacag aaagctctgc atcctgatac tgagagtcca caaaagttgt agtgacccta   8100

acgtcttcaa tatgggcctt ggcgcgcc                                       8128
```

<210> SEQ ID NO 25
<211> LENGTH: 970
<212> TYPE: DNA
<213> ORGANISM: Artificial Sequence
<220> FEATURE:
<223> OTHER INFORMATION: synthetic construct / Zygosaccharomyces parabailii uricase

<400> SEQUENCE: 25

```
taagaactta gtttcgaagt taacatttaa atcaaacaaa atgtcctacc tcgcagactc     60

gacttacggt aaagataatg tcaaattcct caaagttaag aaggaccctt ccaaccctaa    120
```

gttacaacaa gtgatggagg ctactgtcaa agttttgctc agaggtaact ttgatgtttc 180
ttacaccgag gctgacaact ccccaattgt gcctaccgac actgtgaaga acaccatctt 240
gattctagcc agacagaacg atacttggcc cactgaaaaa tttgctgcca agttagccct 300
tcactttaca ggcaagtaca gccatgtttc tggtgtctct atcaagatct accaagagcg 360
ttgggtaaaa tacgatgttg atggaagacc tagccagcat tcttttgtgc accaaggacc 420
tgaaaagaaa atcgtagaac tagaatatga caaggttaac ggtcctactc actacaaatt 480
gagcaccagc atcaaggact tgacagtgct caaatcgacc aactcgatgt tctacgacta 540
caacgtctgc gagtacacta ctttgaagcc taccaccgat cgtgttttgt ccaccgacat 600
ctttgccgta tgggactggt ctgcctcgaa gttgggtcct ctaaccgcta tcgctgcagg 660
cgcatctgac cttgtctttg acaaggtgtt taatgatgcc cgtgatatta ctttggatat 720
cttcgccaag gagaactctg tatcggtaca ggctaccatg tacaacatgg gtgttgccat 780
cttagccaag gcacctcaag tcgaatacgt ttcttacgaa ttgcccaaca agcactatat 840
tctgtttgat ttgaaatggt tccaaggatt gtccaacgac aacgagctct tctatccatc 900
tcctcatcct aatgggttga tcagatgtaa ggttggccgt aagacttcca agctatagtc 960
acatatgaaa 970

<210> SEQ ID NO 26
<211> LENGTH: 2410
<212> TYPE: DNA
<213> ORGANISM: Artificial Sequence
<220> FEATURE:
<223> OTHER INFORMATION: synthetic construct / Zygosaccharomyces parabailii uric acid transporter

<400> SEQUENCE: 26
ctaatcccgg gatccggtac cgcctcttat cgagaaagaa attaccgtcg ctcgtgattt 60
gtttgcaaaa agaacaaaac tgaaaaaacc cagacacgct cgacttcctg tcttcctatt 120
gattgcagct tccaatttcg tcacacaaca aggtcctagc gacggctcac aggttttgta 180
acaagcaatc gaaggttctg gaatggcggg aaagggttta gtaccacatg ctatgatgcc 240
cactgtgatc tccagagcaa agttcgttcg atcgtactgt tactctctct ctttcaaaca 300
gaattgtccg aatcgtgtga caacaacagc ctgttctcac acactctttt cttctaacca 360
agggggtggt ttagtttagt agaacctcgt gaaacttaca tttacatata tataaacttg 420
cataaattgg tcaatgcaag aaatacatat ttggtctttt ctaattctta gtttttcaag 480
ttcttagatg ctttcttttt ctctttttta cagatcatca aggaagtaat tatctacttt 540
ttacaacaaa tataaaacaa tggactctgt acttgaacaa ccaacaaatt ctccttctca 600
gaagatcaag ggatacttct catggttgcg cttcaaattc acaaccagag atggtctctt 660
aggtgactat gactacaaat atctattcac accctcatac ccatttcacg atttcatctg 720
cagactcagg ggcgttgagg tggtcgtgag ggatcaacct ttctttggac tgaacgaaga 780
agtccctgta cttcttggaa tgattctagg cttccagcat gcattggcta tgcttgcagg 840
tgtcataaca cctcctatga tgatagcgag tgcagcaaac ctggattccg tactgaccaa 900
ctatctcgtc tctgcatctt tgattacatc tggtatccta tctgctgtgc aaattacacg 960
ttttcatatc cccaagacta attattacat aggatctggt gtcctttcta ttgtgggaac 1020
ctcctttgcc gtgctgggaa tcgtggacaa atctgtgcct ctcatgtact caacgggata 1080
ctgtccaggg ggtgccaata gtaaagaggc ctgcccagat ggctatggtg cgttgcttgg 1140

-continued

```
tactgcagcg tgctgtgctc tgttggaaat gcttctatca ttcactcctc ctcatattct   1200

gcaaaagatc ttccccaagc aggtcacagg ccccgttgtt ctgaccattg ctgttccctt   1260

gatccagagt ggatttgaag attgggttgg aggctctggc tgcgttggtg caatttgtcc   1320

ttccgaaggt gctccgcagg cggcgccttg gggtctgcc aaattcattg gtttaggttt    1380

cctggtttac acgacaatta ttctctgtga gaaatacggc ccccccattc taaaatcctg   1440

tgctgtcatc gttggcttgt tggtgggatg tatcgtggct gccgcatgtg gctactttca   1500

gcatgatatg attgatgtag cacctgcagc aacatttcta tggaaacaca cgtttagact   1560

gagggtatat gggccagcgg tgctaccatt tcttgtgatg tttattgtgc ttgcccagga   1620

gtgtattggt gatattacag cgacaagtga tgtgtcgcgg ttggaagtcg agggcgaggc   1680

gtatgagtca agaattcaag gtgcagtcct atctgatggt attggtggta tcttatcttc   1740

acttttcaca gtgactccca tgagtacctt cgctcagaac aacggtgtca tttctttgac   1800

caagtgtgct agtcgtcaag cgggttattg gacttgcttc tacatgctta tcatgggtat   1860

ctttgcaaaa ttcggtgcag ccatcgtgca gatccccaaa cctgtcctgg gcggtatgac   1920

aactttcctt ttcaccacag tggccgtggc aggtatcaaa atcatatcag aaattccttt   1980

tacgagaagg gacagatttg tgttgactgg agctctccta ccaggttttg gctctattct   2040

tgtaagcgac tggtttgact acgtctttac ctacaagggt aacaaccatg cattagaggg   2100

gtttttcaat gccattattt tgattatgga gaccagtttc accgtatgcg gtttgaccgc   2160

tatcatccta aaccttttga taccgcaaga gcttgacgaa gagctattgg acgatatcga   2220

ggtacaacaa gaaaacttaa gtgttttgga gggtagaaaa agccccttga ttggacctgt   2280

gatgtctggc aaggaaattg aagcatttga gctaagcagc gaacaaagga cttctgatcc   2340

atgaacagaa gacgggagac actagcacac aactttacca ggcaaggtat ttgacgctag   2400

catgtgtcca                                                           2410
```

THERAPEUTIC ENGINEERED MICROBIAL CELL SYSTEM AND METHODS FOR TREATING HYPERURICEMIA AND GOUT

CROSS REFERENCE TO RELATED APPLICATIONS

This application is a national phase entry under 35 U.S.C. § 371 of International Patent Application PCT/US2021/070014, filed Jan. 8, 2021, designating the United States of America and published in English as International Patent Publication WO 2021/142491 on Jul. 15, 2021, which claims the benefit under Article 8 of the Patent Cooperation Treaty to U.S. Provisional Patent Application Ser. No. 62/959,991, filed Jan. 12, 2020, the entireties of which are hereby incorporated by reference.

STATEMENT REGARDING FEDERALLY SPONSORED RESEARCH OR DEVELOPMENT

This invention was made in part with government support under National Science Foundation Grant 2014679 awarded by the National Science Foundation. The government has certain rights in the invention. 35 USC § 202 (c)(6).

BACKGROUND

Uric acid has been identified as a marker for a number of metabolic and hemodynamic abnormalities (Stack et al. Curr. Med. Res. Opin. Suppl 2:21-26 (2015)).

Gout is a painful, debilitating and progressive metabolic and inflammatory disease caused by abnormally elevated levels of uric acid in the blood stream. Gout is marked by recurrent attacks of red, tender, hot, and/or swollen joints. This leads to the deposition of painful, needle-like uric acid crystals in and around the connective tissue of the joints and in the kidneys, resulting in inflammation, the formation of disfiguring nodules, intermittent attacks of severe pain and kidney damage. In addition, evidence suggests that the chronic elevation of uric acid associated with gout, known as hyperuricemia, may also have systemic consequences, including an increased risk for kidney dysfunction and cardiovascular disease. After years of repetitive attacks, patients suffer the development of a chronic arthritis associated with the deposition of urate crystals and the build up to tophi in the joints (as well as in the tissues of the kidney and heart). The involved joints tend to become chronically deformed and painful and the risk for developing kidney stones, chronic renal insufficiency, and cardiovascular disease increases. This later stage, more involved clinical presentation is generally referred to as chronic tophaceous gout. Once patients reach this stage, they generally suffer multiple attacks every year.

Gout most often affects middle-aged to elderly men and postmenopausal women. The disease is typically associated with hyperuricemia (serum urate level >=6.8 mg per deciliter, which is the upper limit of solubility) and painful episodic acute flares which generally resolve in one to two weeks. Disease prevalence is increasing, and the number of patients suffering could be as high as 6-8 million in the United States, although the relapsing and remitting nature of the disease makes it difficult to estimate a precise number. Prevalence increases with age and risk factors include insulin resistance and obesity, as well as a purine rich diet (meat and seafood). Gout is the most common form of inflammatory arthritis in men over the age of 40 and represents a significant unmet medical need with limited treatment options.

While many patients are well controlled with diet and lifestyle changes, as well as generic medications for acute attacks, many patients still experience poor urate control and progressive symptoms. Patients who experience two attacks per year, or who present with tophi are considered candidates for urate lowering therapy. Three classes of drugs are approved for lowering urate levels: xanthine oxidase inhibitors, uricosuric agents, and uricase agents.

The first line standard of care for chronic disease remains xanthine oxidase inhibition (e.g., febuxostat, allopurinol) which blocks uric acid synthesis, and for many this is an effective treatment option. Alternatively, uricosurics may be prescribed. Uricosuric agents (e.g., probenecid, lesinurad, benzbromarone) are oral drugs that inhibit the urate/anion exchanger URAT1, which is the transporter that mediates reuptake of uric acid from the proximal tubules of the kidney, and thus drive renal elimination of urate Some patients fail all therapy and are thus considered chronic refractory. These patients are candidates for uricase (also known as urate oxidase) agents which break down uric acid directly. KRYSTEXXA® (pegloticase) is a pegylated engineered porcine/baboon hybrid uricase that was approved by the FDA for the treatment of chronic refractory gout in September 2010. Other uricases used to treat hyperuricemia and/or gout are non-engineered *Aspergillus flavus* uricase ('uricozyme') and engineered *Aspergillus flavus* uricase expressed in *S. cerevisiae* ('rasburicase').

Uricase converts uric acid into allantoin which is then excreted. While physicians describe Krystexxa as effective, in the pivotal program the primary endpoint was achieved in only 42% of biweekly cohort and 35% of monthly cohort (v. 0% for placebo). Infusion reactions occurred in 26% of patients receiving q2 week dosing and 40% of patients receiving q4 dosing. Infusion reaction related discontinuation of therapy occurred in 11 and 13% and the label includes a boxed warning for anaphylaxis. Perhaps most concerning, there were eight serious cardiovascular events in patients in the Phase III trials versus one in the placebo arm. Krystexxa administration is inconvenient with patients having to undergo a 4-hour premedication/infusion process once every two weeks.

Overall, treatment options for the majority of the chronic refractory gout population are limited. There remains a need in the art for improved ways to treat hyperuricemia and gout, and in particular, to treat chronic refractory gout.

SUMMARY OF THE INVENTION

The present invention provides microbial cells that have been engineered to comprise a uric acid degrading polypeptide. The engineered microbial cells of the invention are expected to overcome the limitations of existing therapies, and bring relief from debilitating and crippling pain to millions of patients suffering from hyperuricemia, gout, and in particular from refractory gout.

In particular, the present disclosure relates to non-pathogenic microbial cells that are engineered to comprise a uric acid degrading polypeptide (e.g., uricase), a uric acid transporter, or both a uric acid degrading polypeptide and a uric acid transporter. The engineered microbial cells can be probiotic cells. The engineered cells can be eukaryotic, e.g., fungal, e.g., *Saccharomyces boulardii*. The engineered cells can be bacterial, e.g., from the genus *Lactobacillus*, or can be archaeal. In one embodiment, the engineered microorganism constitutively expresses the polypeptide(s). In another embodiment, the microorganism is probiotic.

The engineered microbial cells are useful in the treatment of diseases and conditions associated with hyperuricemia, and in particular, gout. The present disclosure is based in part on the selection of a uric acid degrading polypeptide (e.g., uricase) and optionally together with a uric acid transporter that, when expressed in a microbial cell, increase uricolytic activity.

In some embodiments, pharmaceutical compositions comprising the engineered microbial cells described herein are administered to a subject (e.g., a human subject) for treatment of a disease or disorder. For example, the pharmaceutical composition may be administered orally to the subject. In some embodiments, the engineered microbial cells shield the uric acid degrading polypeptide and/or uric acid transporter from the harsh conditions encountered in the subject's gastrointestinal tract, unlike current uricase treatments. Such harsh conditions include but are not limited to low pH, presence of proteases, bile acids, and other factors promoting the denaturation and degradation of proteins. These engineered microbial cells may act as metabolic factories in the gastrointestinal tract to effectively reduce serum uric acid levels in the subject, working longer and more effectively than naked uricase subjected to the conditions of the gastrointestinal tract.

In one aspect, the disclosure features a microbial cell engineered to degrade uric acid, comprising a first exogenous polypeptide comprising a uric acid degrading polypeptide, or a variant thereof. In one embodiment, the uric acid degrading polypeptide is a uricase, or a variant thereof.

In one embodiment, the engineered microbial cell is a fungal cell, e.g. *Saccharomyces boulardii.*

In one embodiment of the above aspects and embodiments, the uricase is a fungal uricase. In one embodiment, the fungal uricase is derived from *Candida utilis*. In one embodiment, the uricase derived from *Candida utilis* comprises an amino acid sequence that is at least 95% identical to the amino acid sequence set forth in SEQ ID NO: 1. In one embodiment, the fungal uricase is derived from *Aspergillus flavus*. In one embodiment, the uricase derived from *Aspergillus flavus* comprises an amino acid sequence that is at least 95% identical to the amino acid sequence set forth in SEQ ID NO: 2. In one embodiment of the above aspects and embodiments, the uricase is a bacterial uricase. In one embodiment, the bacterial uricase is derived from *Arthrobacter globiformis*. In one embodiment, the uricase derived from *Arthrobacter globiformis* comprises an amino acid sequence that is at least 95% identical to the amino acid sequence set forth in SEQ ID NO: 3. In one embodiment, the uricase is a porcine/baboon uricase chimera. In one embodiment, the porcine/baboon uricase chimera comprises an amino acid sequence that is at least 95% identical to the amino acid sequence set forth in SEQ ID NO: 4. In one embodiment, the fungal uricase is derived from *Schizosaccharomyces pombe*. In one embodiment, the uricase derived from *Schizosaccharomyces pombe* comprises an amino acid sequence that is at least 95% identical to the amino acid sequence set forth in SEQ ID NO: 5. In one embodiment, the bacterial uricase is derived from *Bacillus subtilis*. In one embodiment, the uricase derived from *Bacillus subtilis* comprises an amino acid sequence that is at least 95% identical to the amino acid sequence set forth in SEQ ID NO: 6. In one embodiment, the fungal uricase is derived from *Zygosaccharomyces parabailii*. In one embodiment, the uricase derived from *Zygosaccharomyces parabailii* comprises an amino acid sequence that is at least 95% identical to the amino acid sequence set forth in SEQ ID NO: 7.

In one embodiment, the fungal uricase is derived from *Spirosoma* sp. KCTC 42546. In one embodiment, the uricase derived from *Spirosoma* sp. KCTC 42546 comprises an amino acid sequence that is at least 95% identical to the amino acid sequence set forth in SEQ ID NO: 8.

In one embodiment of the above aspects and embodiments, the uricase is a mutant uricase that retains the uricolytic activity of the wild type uricase. In one embodiment of the above aspects and embodiments, the first exogenous polypeptide is expressed inside the engineered microbial cell. In one embodiment of the above aspects and embodiments, the engineered microbial cell further comprises a second exogenous polypeptide comprising a uric acid transporter, or a variant thereof.

In one embodiment, the uric acid transporter is a fungal uric acid transporter. In one embodiment, the uric acid transporter is a bacterial uric acid transporter.

In one embodiment, the uric acid transporter is selected from the group consisting of: *Aspergillus nidulans* UapA, *Aspergillus nidulans* UapC, *Aspergillus fumigatus* UapC, *Candida albicans* Xut1, *Schizosaccharomyces pombe* Q9HE12, *Bacillus subtilis* PucK, *Bacillus subtilis* PucJ, *Escherichia coli* YgfU, or *Zygosaccharomyces parabailii* AQZ18664, or *Spirosoma* sp. KCTC 42546 WP_142773020.

In one embodiment, *Aspergillus nidulans* UapA comprises an amino acid sequence that is at least 95% identical to the amino acid sequence set forth in SEQ ID NO: 9; wherein *Aspergillus nidulans* UapC comprises an amino acid sequence that is at least 95% identical to the amino acid sequence set forth in SEQ ID NO: 10; wherein *Aspergillus fumigatus* UapC comprises an amino acid sequence that is at least 95% identical to the amino acid sequence set forth in SEQ ID NO: 11; wherein *Candida albicans* Xut1 comprises an amino acid sequence that is at least 95% identical to the amino acid sequence set forth in SEQ ID NO: 12; wherein *Schizosaccharomyces pombe* Q9HE12 comprises an amino acid sequence that is at least 95% identical to the amino acid sequence set forth in SEQ ID NO: 13; wherein *Bacillus subtilis* Puck comprises an amino acid sequence that is at least 95% identical to the amino acid sequence set forth in SEQ ID NO: 14; wherein *Bacillus subtilis* PucJ comprises an amino acid sequence that is at least 95% identical to the amino acid sequence set forth in SEQ ID NO: 15; wherein *Escherichia coli* YgfU comprises an amino acid sequence that is at least 95% identical to the amino acid sequence set forth in SEQ ID NO: 16; wherein *Zygosaccharomyces parabailii* AQZ18664.1 comprises an amino acid sequence that is at least 95% identical to the amino acid sequence set forth in SEQ ID NO: 17; wherein *Spirosoma* sp. KCTC 42546 WP_142773020 comprises an amino acid sequence that is at least 95% identical to the amino acid sequence set forth in SEQ ID NO: 18.

In one embodiment, the second exogenous polypeptide is presented at the surface of the microbial cell.

In some embodiments, the uric acid transporter transports uric acid from outside the microbial cell to the inside of the microbial cell. In some embodiments of the above aspects and embodiments, the microbial cell when administered to a subject is capable of reducing serum uric acid level in the subject. In some embodiments, the level of serum uric acid is reduced to about 6.8 mg/dl or less.

In some embodiments of the above aspects and embodiments, the engineered microbial cell is a eukaryotic cell. In some embodiments of the above aspects and embodiments, the engineered microbial cell is a fungal cell. In some embodiments of the above aspects and embodiments, the engineered microbial cell is *Saccharomyces boulardii*. In some embodiments of all aspects of the invention, the uric acid degrading polypeptide is not uricase. In some embodiments of all aspects of the invention, the uric acid degrading polypeptide is not *Candida utilis* uricase.

In another aspect, the disclosure provides an engineered microbial cell comprising a first exogenous polypeptide comprising a uric acid transporter, or a variant thereof.

In some embodiments, the first exogenous polypeptide is presented at the surface of the engineered microbial cell.

In some embodiments, the uric acid transporter transports uric acid from outside the microbial cell to the inside of the microbial cell.

In some embodiments of the above aspects and embodiments, the engineered microbial cell is a fungal cell, e.g. *Saccharomyces boulardii.*

In another aspect, the disclosure provides an engineered microbial cell comprising a first exogenous polypeptide comprising a uricase, or a variant thereof, and a second exogenous polypeptide comprising a uric acid transporter, or a variant thereof.

In another aspect, the disclosure provides an engineered microbial cell comprising a first exogenous polypeptide comprising *Candida utilis* uricase, or a variant thereof, and a second exogenous polypeptide comprising *Aspergillus nidulans* Uapa, or a variant thereof.

In another aspect, the disclosures provides an engineered microbial cell comprising a first exogenous polypeptide comprising *Candida utilis* uricase, or a variant thereof, and a second exogenous polypeptide comprising a uric acid transporter selected from the group consisting of *Aspergillus nidulans* UapA, *Aspergillus nidulans* UapC, *Aspergillus fumigatus* UapC, *Candida albicans* Xut1, *Schizosaccharomyces pombe* Q9HE12, *Bacillus subtilis* PucK, *Bacillus subtilis* PucJ, *Escherichia coli* YgfU, *Zygosaccharomyces parabailii* AQZ18664, or *Spirosoma* sp. KCTC 42546 WP_142773020.

In some embodiments of the above aspects, the engineered microbial cell is a fungal cell, e.g. *Saccharomyces boulardii.*

In another aspect, the disclosure provides a pharmaceutical composition comprising a plurality of the engineered microbial cells of any one of the above aspects and embodiments, and a pharmaceutically acceptable carrier. In some embodiments, the pharmaceutical composition comprises a therapeutically effective dose of the engineered microbial cells.

In another aspect, the disclosure provides a method of treating or preventing hyperuricemia in a subject, comprising administering to the subject the engineered microbial cell of any of the foregoing aspects and embodiments, in an amount effective to treat or prevent hyperuricemia in the subject. In some embodiments, the subject has a serum urate level greater than about 6.8 mg/dl prior to administering the engineered microbial cell. In some embodiments, the subject has a serum urate level greater than about 8.0 mg/dl prior to administering the engineered microbial cell. In some embodiments, the subject has a serum urate level less than about 6.8 mg/dl after administering the engineered microbial cell. In some embodiments, the subject has a serum urate level of about 6.0 mg/dl after administering the engineered microbial cell. In some embodiments, the subject has been diagnosed with a disease selected from the group consisting of: gout, rheumatoid arthritis, osteoarthritis, cerebral stroke, ischemic heart disease, arrhythmia, and chronic renal disease. In a further embodiment, the gout is chronic refractory gout. In some embodiments, the subject has one or more risk factors for hyperuricemia selected from the group consisting of insulin resistance, obesity, a purine rich diet and advanced age. In some embodiments, the subject has been diagnosed with symptomatic gout with at least 3 gout flares in the previous 18 months. In some embodiments, the subject has been diagnosed with at least 1 gout tophus or gouty arthritis. In some embodiments, the subject has previously been treated with a urate lowering therapy, and failed to normalize level of serum uric acid to about 6.8 mg/dl or less. In some embodiments, the subject has a contraindication to allopurinol. In some embodiments, the subject has a failure to normalize uric acid to less than 6 mg/dL after at least 3 months of allopurinol treatment.

In some embodiments, the engineered microbial cell is administered to the subject about thrice daily. In some embodiments, the method further comprises administration of a second agent.

In another aspect, the disclosure provides an engineered microbial cell (e.g., engineered fungal cell), comprising a first exogenous polypeptide comprising a uric acid degrading polypeptide, or a variant thereof, produced by a process comprising introducing an exogenous nucleic acid encoding the first exogenous polypeptide into a microbial cell and culturing the microbial cell under conditions suitable for production of the first exogenous polypeptide.

In another aspect, the disclosure provides an engineered microbial cell (e.g., engineered fungal cell), comprising a first exogenous polypeptide comprising a uric acid transporter, or a variant thereof, produced by a process comprising introducing an exogenous nucleic acid encoding the first exogenous polypeptide into a microbial cell (e.g., fungal cell); and culturing the microbial cell under conditions suitable for production of the first exogenous polypeptide.

In another aspect, the disclosure provides an engineered microbial cell (e.g., engineered fungal cell), comprising at a first exogenous polypeptide comprising a uric acid degrading polypeptide, or a variant thereof, and a second exogenous polypeptide comprising a uric acid transporter, or a variant thereof, produced by a process comprising introducing an exogenous nucleic acid encoding the first exogenous polypeptide into a microbial cell (e.g., fungal cell); introducing an exogenous nucleic acid encoding the second exogenous polypeptide into a microbial cell (e.g., fungal cell); and culturing the microbial cell under conditions suitable for production of the first exogenous polypeptide and the second exogenous polypeptide.

In some embodiments, the uric acid degrading polypeptide is a uricase, or a variant thereof. In some embodiments, the uric acid degrading polypeptide is an allantoinase, or variant thereof. In some embodiments of the foregoing aspects, the exogenous nucleic acid comprises DNA or RNA. In some embodiments, the introducing step comprises electroporation or chemical transformation.

In some embodiments of the foregoing aspects, the introducing step comprises introducing the first exogenous nucleic acid encoding the first exogenous polypeptide by electroporation of an episomal vector. In some embodiments of the foregoing aspects, the introducing step comprises introducing the first exogenous nucleic acid encoding the first exogenous polypeptide and the second exogenous nucleic acid encoding the second exogenous polypeptide by electroporation of an episomal vector, wherein the first exogenous nucleic acid and the second exogenous nucleic acid are contained in the same episomal vector.

In some embodiments of the foregoing aspects, the introducing step comprises introducing the first exogenous nucleic acid encoding the first exogenous polypeptide by electroporation of a first episomal vector, and introducing the second exogenous nucleic acid encoding the second exogenous polypeptide by electroporation of a second episomal vector.

In some embodiments of the foregoing aspects, the episomal vector comprises a promoter selected from the group consisting of *Saccharomyces boulardii* phosphoglycerate kinase 1 (PGK1), GPD (also known as TDH3 or GAPDH), GPM1, TPI1, or TEF1 promoter.

BRIEF DESCRIPTION OF DRAWINGS

Non-limiting and non-exhaustive examples of several of the various embodiments of the present subject matter are described with references to the following figures, and reference numbers refer to the same features throughout the various views and embodiments unless otherwise specified.

DETAILED DESCRIPTION OF THE DRAWINGS

Figure 1:
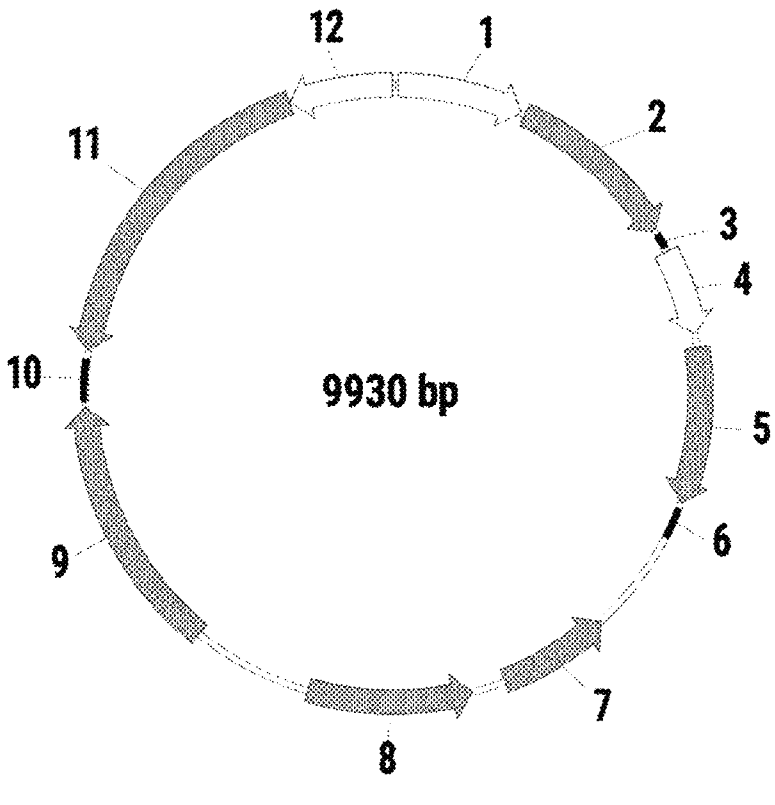
FIG. 1 is a genetic map of episomal plasmid used to transform *S. boulardii*, by way of an example embodiment, and provide it with the ability to degrade uric acid, as described in Example 1.

Now in reference to FIG. 1, it is a Genetic map of episomal plasmid used to transform 1 *S. boulardii* and provide it with the ability to degrade uric acid, as described in Example 1. The genetic map shows *Saccharomyces boulardii* GPD (TDH3) promoter [1]; *Candida utilis* uricase ORF [2]; *Saccharomyces boulardii* VPS13 terminator [3]; *Saccharomyces boulardii* TP11 promoter [4]; G418—Resistance ORF [5]; *Saccharomyces boulardii* [6]; F1 Origin of replication [7]; Ampicillin Resistance ORF [8]; *Saccharomyces boulardii* 2 micron plasmid origin of replication [9]; *Saccharomyces boulardii* Pm9 terminator [10]; *Aspergillus nidulans* UapA Uric acid transporter ORF [11]; and *Saccharomyces boulardii* Pgk1 promoter [12].

Figure 2:
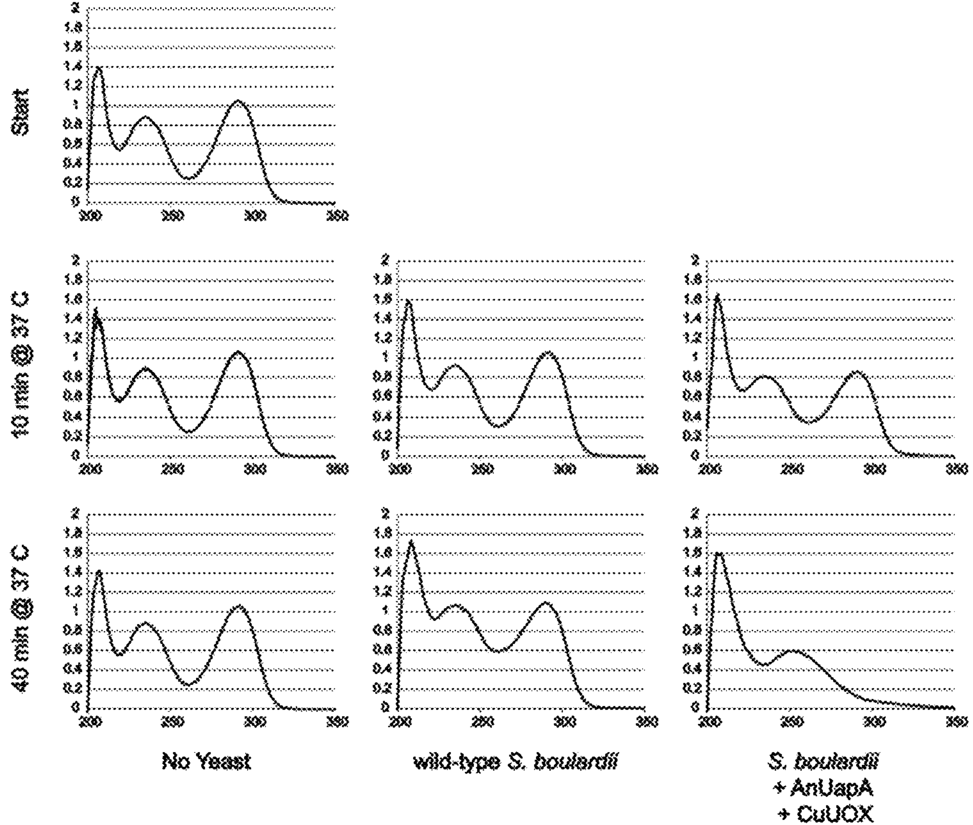
FIG. 2 shows the absorbance spectra of uric acid solutions in Phosphate Buffered Saline (PBS) with no addition of yeast, with non-modified wild-type *S. boulardii* cells added, and with modified *S. boulardii* cells expressing *Candida utilis* uricase and *Aspergillus nidulans* UapA uric acid transporter.

Now in reference to FIG. 2, it is an absorbance spectra of uric acid solutions in PBS with no addition ("No yeast", left 3 panels), with non-modified wild-type *S. boulardii* cells added ("wild-type *S. boulardii*", center 2 panels), and with modified *S. boulardii* cells expressing *Candida utilis* uricase and *Aspergillus nidulans* UapA uric acid transporter ("*S. boulardii*+AnUapA+CuUOX", right 2 panels). Top row: before addition of yeast. Center row: after 10' incubation at 37° C. Bottom row: after 40' incubation at 37° C. X-axis: wavelength. Y-axis: absorbance. Uric acid is progressively degraded in the Uric acid solution with modified *S. boulardii* cells expressing *Candida utilis* uricase and *Aspergillus nidulans* UapA uric acid transporter added, as indicated by the progressive reduction of the peak at 293 nm. In contrast, Uric acid is not degraded in the Uric acid solution with non-modified wild-type *S. boulardii* cells added, as indicated by the fact the peak at 293 nm did not change over time. Uric acid also was not degraded in the Uric acid solution no *S. boulardii* cells added, as indicated by the fact no decrease in the peak at 293 nm was observed over time.

Figure 3:
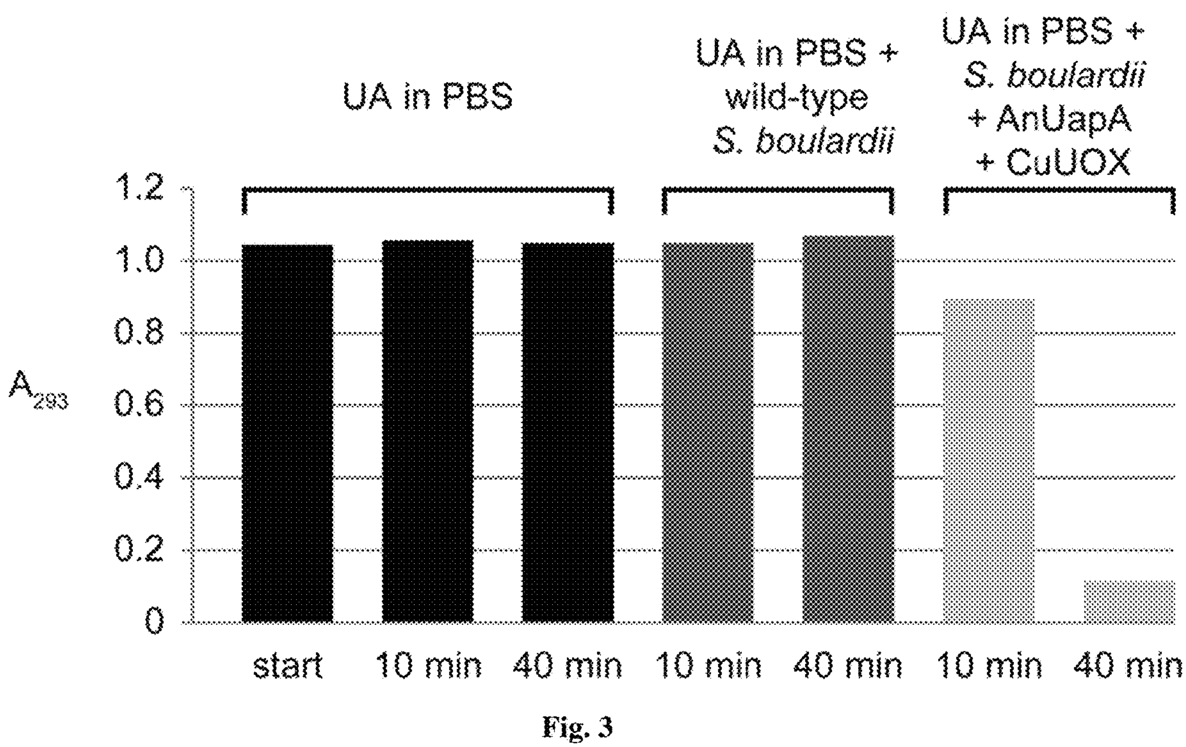
FIG. 3 shows the absorbance of: uric acid solutions in PBS, in PS with addition of non-modified wild-type *S. boulardii* cells, and in PBS with addition of modified *S. boulardii* cells expressing *Candida utilis* uricase and *Aspergillus nidulans* UapA uric acid transporter, observed over time at 293 nm.

Now in reference to FIG. 3, it shows absorbance at 293 nm of uric acid solutions in PBS with no addition ("UA in PBS", left 3 columns), with non-modified wild-type *S. boulardii* cells added ("UA in PBS+wild-type *S. boulardii",* 4$^{th}$ and 5$^{th}$ columns), and with modified *S. boulardii* cells expressing *Candida utilis* uricase and *Aspergillus nidulans* UapA uric acid transporter ("UA in PBS+*S. boulardii*+AnUapA+CuUOX", right 2 columns). X-axis: absorbance at 293 nm. Uric acid is progressively degraded in the Uric acid solution with modified *S. boulardii* cells expressing *Candida utilis* uricase and *Aspergillus nidulans* UapA uric acid transporter added, as indicated by the progressive decrease in Absorbance at 293 nm. In contrast, Uric acid is not degraded in the Uric acid solution with non-modified wild-type *S. boulardii* cells added, as indicated by the fact no decrease in Absorbance at 293 nm was observed over time. Uric acid also was not degraded in the Uric acid solution no *S. boulardii* cells added, as indicated by the fact no decrease in Absorbance at 293 nm was observed over time.

Figure 4:
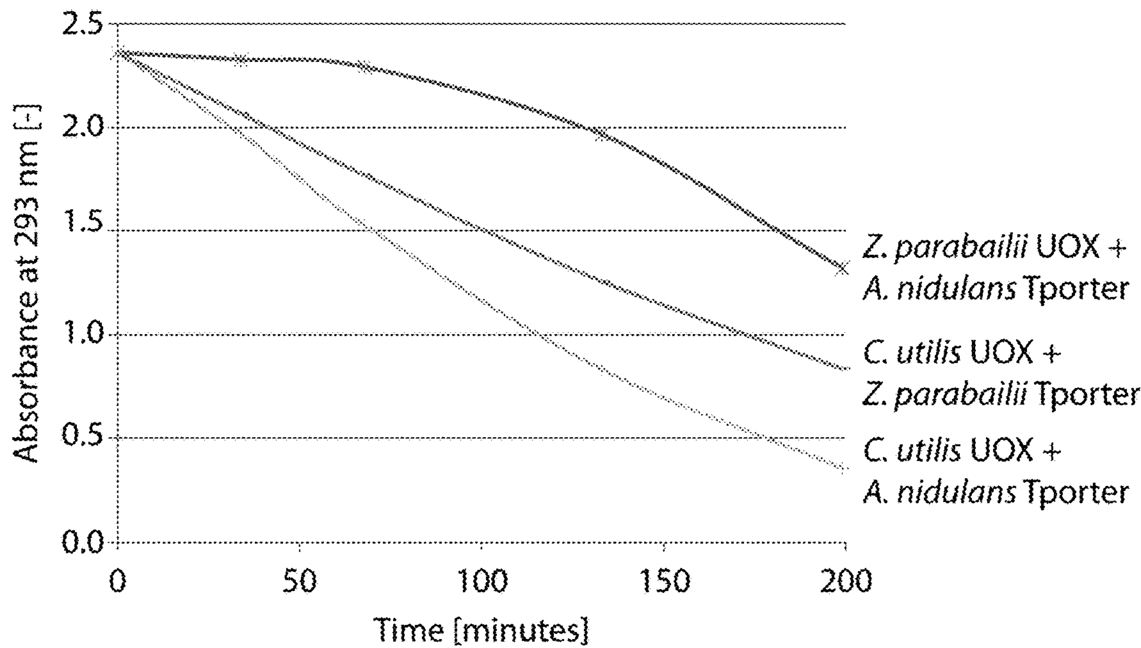
FIG. 4 shows the urate consumption assay comparing urate uptake and breakdown capacity for probiotic strains produced as outlined in Example 1, Example 7, and Example 8.

Now in reference to FIG. 4, it shows a Urate consumption assay comparing urate uptake and breakdown capacity for probiotic strains produced as outlined in Example 1, Example 7, and Example 8. *S. boulardii* cells expressing *Candida utilis* uricase and *Aspergillus nidulans* UapA uric acid transporter ("*C. utilis* UOX+*A. nidulans* Tporter"), produced as outlined in Example 1 most rapidly depleted urate in the assay buffer, followed by *S. boulardii* cells expressing *Candida utilis* uricase and *Zygosaccharomyces parabailii* uric acid transporter ("*C. utilis* UOX+*Z. parabailii* Tporter"), produced as outlined in Example 8, followed by *S. boulardii* cells expressing *Zygosaccharomyces parabailii* uricase and *Aspergillus nidulans* UapA uric acid transporter ("*Z. parabailii* UOX+*A. nidulans* Tporter").

DETAILED DESCRIPTION OF THE INVENTION

In this Specification, which includes the figures, claims, and this detailed description, reference is made to particular and possible features of the embodiments of the invention, including method steps. These particular and possible features are intended to include all possible combinations of such features, without exclusivity. For instance, where a feature is disclosed in a specific embodiment or claim, that feature can also be used, to the extent possible, in combination with and/or in the context of other aspects and embodiments of the invention, and in the invention generally. Additionally, the disclosed architecture is sufficiently configurable, such that it may be utilized in ways other than what is shown.

The purpose of the Abstract of this Specification is to enable the U.S. Patent and Trademark Office and the public generally, and especially the scientists, engineers and practitioners of the art who are not familiar with patent or legal terms or phrasing, to determine quickly from a cursory inspection the nature and essence of the technical disclosure of the application. The Abstract is not intended to be limiting as to the scope of the invention in any way.

In the following description, numerous specific details are given in order to provide a thorough understanding of the present embodiments. It will be apparent, however, to one having ordinary skill in the art, that the specific detail need not be employed to practice the present embodiments. On other instances, well-known materials or methods have not been described in detail in order to avoid obscuring the present embodiments. When limitations are intended in this Specification, they are made with expressly limiting or exhaustive language.

Reference throughout this Specification to "one embodiment", "an embodiment", "one example" or "an example" means that a particular feature, structure, or characteristic described in connection with the embodiment or example is included in at least one embodiment of the present embodiments. Thus, appearances of the phrases "in one embodiment", "according to an embodiment", "in an embodiment", "one example", "for example", "an example", or the like, in various places throughout this Specification are not necessarily all referring to the same embodiment or example. Furthermore, the particular features, structures, or characteristics may be combined in any suitable combinations and/or sub-combinations in one or more embodiments or examples.

The terms "comprises", "comprising", "includes", "including", "has", "having", "could", "could have" or their grammatical equivalents, are used in this Specification to mean that other features, components, materials, steps, etc. are optionally present as a non-exclusive inclusion. For instance, a device "comprising" (or "which comprises" or "is comprised of") components A, B, and C can contain only components A, B, and C, or can contain not only components A, B, and C but also one or more other components. For example, a method comprising two or more defined steps can be carried out in any order or simultaneously, unless the context excludes that possibility; and the method can include one or more other steps which are carried out before any of the defined steps, between two of the defined steps, or after all the defined steps, unless the context excludes that possibility.

Further, unless expressly stated to the contrary, "or" refers to an inclusive or and not to an exclusive or. For example, An embodiment could have optional features A, B, or C, so the embodiment could be satisfied with A in one instance, with B in another instance, and with C in a third instance, and probably with AB, AC, BC, or ABC if the context of features does not exclude that possibility.

Examples or illustrations given are not to be regarded in any way as restrictions on, limits to, or express definitions of any term or terms with which they are utilized. Instead, these examples or illustrations are to be regarded as being described with respect to one particular embodiment and as being illustrative only. Those of ordinary skill in the art will appreciate that any term or terms with which these example or illustrations are utilized will encompass other embodiments, which may or may not be given in this Specification, and all such embodiments are intended to be included within the scope of that term or terms. Language designating such nonlimiting examples and illustrations includes, but is not limited to "for example", "for instance", "etc.", "or otherwise", and "in one embodiment."

The phrase "at least" followed by a number is used to denote the start of a range beginning with that number, which may or may not be a range having an upper limit, depending on the variable defined. For instance, "at least 1" means 1 or more.

In this specification. "a" and "an" and similar phrases are to be interpreted as "at least one" and "one or more." In this specification, the term "may" or "can be" or "could be" is to be interpreted as "may, for example." In other words, the term "may" is indicative that the phrase following the term "may" is an example of one of a multitude of suitable possibilities that may, or may not, be employed to one or more of the various embodiments.

The phrase "a plurality of" followed by a feature, component, or structure is used to mean more than one, specifically including a great many, relative to the context of the component.

It is the applicant's intent that only claims that include the express language "means for" or "step for" be interpreted under 35 U.S.C. § 112. Claims that do not expressly include the phrase "means for" or "step for" are not to be interpreted under 35 U.S.C. § 112.

The disclosure of this patent document incorporates material which is subject to copyright protection. The copyright owner has no objection to the facsimile reproduction by anyone of the patent document or the patent disclosure, as it appears in the Patent and Trademark Office patent file or records, for the limited purpose required by law, but otherwise reserves all copyright rights whatsoever.

The present disclosure is based on the development of microbial cells, e.g., fungal cells, that have been engineered to include a uric acid degrading polypeptide, a uric acid transporter, or both a uric acid degrading polypeptide and a uric acid transporter.

According to embodiments of the present disclosure, the engineered microbial cells are fungal, bacterial, or archaeal cells. According to embodiments of the present disclosure, the uric acid degrading polypeptide is located inside the cell (e.g., expressed in a microbial cell) and the uric acid transporter is located at the surface of the microbial cell, such that the uric acid transporter promotes uptake of uric acid into the cell.

The engineered microbial cells of the present invention provide advantages to, for example, non-engineered cells. In contrast to the microbial cells of the present invention, which are engineered to comprise a uric acid degrading polypeptide inside the cell, a non-engineered microbial cell is limited with respect to the levels of polypeptide that may be present in the cell. According to embodiments of the present disclosure, the engineered microbial cells are fungal cells (e.g., *Saccharomyces boulardii*).

Moreover, the engineered microbial cells of the invention confer protection to bile acid, proteolytic enzymes, and/or acid pH to the uric acid degrading polypeptide, and/or the uric acid transporter, as compared to when the uric acid degrading polypeptide, and/or the uric acid transporter polypeptides are administered to a subject alone (i.e., not present in or on a microbial cell).

Many modifications and other embodiments of the inventions set forth herein will easily come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

As used herein, the terms "about", "approximate", and "substantially" when referring to a measurable value such as an amount, a temporal duration, and the like; would be understood by a person of ordinary skill in the art that the given feature is close enough to the exact feature or value that the invention can still be practiced; i.e., that the difference is not so significant as to render the present invention inoperable. From a quantifiable perspective, it might be helpful to think of these terms as encompassing variations of ±20% or ±10%, more preferably ±5%, even more preferably ±1%, and still more preferably ±0.1% from the specified value, as such variations are appropriate to perform the disclosed methods.

As used herein, any concentration range, percentage range, ratio range, or integer range is to be understood to include the value of any integer within the recited range and, when appropriate, fractions thereof (such as one tenth and one hundredth of an integer), unless otherwise indicated.

As used herein, the terms "such as", "for example" and the like are intended to refer to exemplary embodiments and not to limit the scope of the present disclosure.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, preferred materials and methods are described herein.

As used herein, a "microbial cell", or "microbe" refers to single-celled organisms, whether organized as colonies, suspensions, individual cells, or other configurations and collections; alive or dead or in a state of metabolic statis or suspension; including but not limited to organisms such as Bacteria, Archaea, Fungi, or Protists. Clearly, cells capable of enzymatic activity are needed to transport and degrade uric acid, and thus practice the invention. For example, bacterial microbes may include e.g., *Lactobacillus casei*, and fungal microbes may include e.g., *Saccharomyces boulardii*.

As used herein, an "additional therapeutic" refers to any therapeutic that is used in addition to another treatment. For example, when the method is one directed to treatment with the engineered microbial cells described herein, and the method comprises the use of an additional therapeutic, the additional therapeutic is in addition to the engineered microbial cells described herein. Generally, the additional therapeutic will be a different therapeutic. The additional therapeutic may be administered at the same time or at a different time and/or via the same mode of administration or via a different mode of administration, as that of the other therapeutic. In preferred embodiments, the additional therapeutic will be given at a time and in a way that will provide a benefit to the subject during the effective treatment window of the other therapeutic. When two compositions are administered with a specific time period, generally the time period is measured from the start of the first composition to the start of the second composition. As used herein, when two compositions are given within an hour, for example, the time before the start of the administration of the first composition is about an hour before the start of the administration of the second composition. In some embodiments, the additional therapeutic is another therapeutic for the treatment of gout or a condition associated with gout. As used herein, a "gout therapeutic" is any therapeutic that can be administered and from which a subject with gout may derive a benefit because of its administration. In some embodiments, the gout therapeutic is an oral gout therapeutic (i.e., a gout therapeutic that can be taken or given orally).

As used herein, "dose" refers to a specific quantity of a pharmacologically active material for administration to a subject for a given time. Unless otherwise specified, the doses recited refer to an engineered microbial cell comprising a uric acid degrading polypeptide as described herein, an engineered microbial cell comprising a uric acid transporter as described herein, or an engineered microbial cell comprising a uric acid degrading polypeptide and a uric acid transporter as described herein. In some embodiments, a dose of engineered microbial cells refers to an effective amount of engineered microbial cells. For example, in some embodiments a dose or effective amount of engineered microbial cells comprises at least 10^6 CFUs of engineered microbes per dose. In some embodiments, a dose or effective amount of engineered microbial cells refers to about 10^6-10^12 engineered microbial cells per dose. When referring to a dose for administration, in an embodiment of any one of the methods, compositions or kits provided herein, any one of the doses provided herein is the dose as it appears on a label/label dose.

As used herein, a "drug-induced" gout flare refers to an occurrence of or increased incidence of a gout flare associated with initiation of therapy to treat gout and/or administration of a therapeutic agent for the treatment of gout, for example, initiation of therapy with a xanthine oxidase inhibitor, urate oxidase, or a uricosuric agent. A gout flare is "associated" with initiation of gout therapy when the flare occurs contemporaneously or following at least a first administration of a therapeutic agent for the treatment of gout.

As used herein, an "elevated serum uric acid level" refers to any level of uric acid in a subject's serum that may lead to an undesirable result or would be deemed by a clinician to be elevated. In an embodiment, an elevated serum uric acid level refers to a level of uric acid considered to be above normal by the American Medical Association. In an embodiment, the subject of any one of the methods provided herein can have a serum uric acid level of >5 mg/dL, >6 mg/dL, or >7 mg/dL. Such a subject may be a hyperuricemic subject. Whether or not a subject has elevated blood uric acid levels can be determined by a clinician, and in some embodiments, the subject is one in which a clinician has identified or would identify as having elevated serum uric acid levels.

As used herein, the term "endogenous" is meant to refer to a native form of compound (e.g., a small molecule) or process. For example, in some embodiments, the term "endogenous" refers to the native form of a nucleic acid or polypeptide in its natural location in the organism or in the genome of an organism.

As used herein, the term "an engineered cell" is meant to refer to a genetically-modified cell or progeny thereof.

As used herein, the term "microbial" cell refers to a cell, e.g., a bacterial, fungal or archaeal cell, which may be a prokaryotic or eukaryotic cell. As used herein, a microbial cell includes a metabolically inactive spore or cell capable of germinating into or of being reconstituted into a metabolically active cell. As used herein, a microbial cell includes freeze-dried, spray-dried, or otherwise dried microbial cell.

As used herein, the term "probiotic" refers to live microbial cells that, when administered in adequate amounts, may or may not confer a health benefit on the host, and do not exert harmful effects.

As used herein, the term "exogenous," when used in the context of nucleic acid, includes a transgene and engineered nucleic acids.

As used herein, the term "exogenous nucleic acid" refers to a nucleic acid (e.g., a gene) which is not native to a cell, but which is introduced into the cell or a progenitor of the cell. An exogenous nucleic acid may include a region or open reading frame (e.g., a gene) that is homologous to, or identical to, an endogenous nucleic acid native to the cell. In some embodiments, the exogenous nucleic acid comprises RNA. In some embodiments, the exogenous nucleic acid comprises DNA. In some embodiments, the exogenous nucleic acid is integrated into the genome of the cell. In some embodiments, the exogenous nucleic acid is processed by the cellular machinery to produce an exogenous polypeptide. In some embodiments, the exogenous nucleic acid is not retained by the cell or by a cell that is the progeny of the cell into which the exogenous nucleic acid was introduced.

As used herein, the term "exogenous polypeptide" refers to a polypeptide that is not produced by a wild-type cell of that type or is present at a lower level in a wild-type cell than in a cell containing the exogenous polypeptide. In some embodiments, an exogenous polypeptide refers to a polypeptide that is introduced into or onto a cell, or is caused to be expressed by the cell by introducing an exogenous nucleic acid encoding the exogenous polypeptide into the cell or into a progenitor of the cell. In some embodiments, an exogenous polypeptide is a polypeptide encoded by an exogenous nucleic acid that was introduced into the cell, or a progenitor of the cell, which nucleic acid is optionally not retained by the cell.

As used herein, the term "express" or "expression" refers to the process to produce a polypeptide, including transcription and translation. Expression may be, e.g., increased by a number of approaches, including: increasing the number of genes encoding the polypeptide, increasing the transcription of the gene (such as by placing the gene under the control of a constitutive promoter), increasing the translation of the gene, knocking out of a competitive gene, or a combination of these and/or other approaches.

As used herein, the term "transcription regulatory sequence" refers to a first nucleotide sequence that regulates transcription of a second nucleotide sequence to which it is operatively linked.

A "promoter" is a transcription regulatory sequence at least sufficient to promote the transcription of a nucleotide sequence in DNA into an RNA transcript. A transcript transcribed from a promoter typically includes sequences from the promoter downstream of the transcription start site, as well as downstream sequences that, in the case of mRNA, encode an amino acid sequence. Promoters are the best-characterized transcriptional regulatory sequences because of their predictable location immediately upstream of transcription start sites. Promoters include sequences that modulate the recognition, binding and transcription initiation activity of the RNA polymerase. These sequences can be cis acting or can be responsive to trans acting factors. Promoters, depending upon the nature of the regulation, can be constitutive or regulated. They are often described as having two separate segments: core and extended promoter regions.

The core promoter includes sequences that are sufficient for RNA polymerase recognition, binding and transcription initiation. The core promoter includes the transcriptional start site, an RNA polymerase binding site, and other general transcription binding sites and is where the pre-initiation complex forms and the general transcription machinery assembles. The pre-initiation complex is generally within 50 nucleotides (nt) of the transcription start site (TSS).

The core promoter also includes a sequence for a ribosome binding site, necessary for translation of an mRNA into a polypeptide.

The extended promoter region includes the so-called proximal promoter, which extends to about 250 nucleotides upstream of the transcriptional start site (i.e., −250 nt). It includes primary regulatory elements such as specific transcription factor binding sites. It has been found that many genes have transcription regulatory elements located further upstream. In particular, a fragment that includes most of the transcription regulatory elements of a gene can extend up to 700 nt or more up-stream of the transcription start site. In certain genes, transcription regulatory sequences have been found thousands of nucleotides upstream of the transcriptional start site.

As used herein, a nucleotide sequence is "operatively linked" or "operably linked" with a transcription regulatory sequence when the transcription regulatory sequence functions in a cell to regulate transcription of the nucleotide sequence. This includes promoting transcription of the nucleotide sequence through an interaction between a polymerase and a promoter.

As used herein, a first nucleotide sequence is "heterologous" to a second nucleotide sequence if the first nucleotide sequence is not operatively linked with the second nucleotide sequence in nature. By extension, a polypeptide is "heterologous" to an expression control sequence if it is encoded by nucleotide sequence heterologous the promoter.

As used herein, the terms "first", "second" and "third", etc. with respect to exogenous polypeptides are used for convenience of distinguishing when there is more than one type of exogenous polypeptide. Use of these terms is not intended to confer a specific order or orientation of the exogenous polypeptides unless explicitly so stated.

As used herein, the term "fragment" refers to sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full-length sequence. Fragments may be derived from any contiguous portion of a nucleic acid or amino acid sequence of choice.

As used herein, the term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

As used herein, the term "gout" generally refers to a disorder or condition associated with the buildup of uric acid, such as deposition of uric crystals in tissues and joints, and/or a clinically relevant elevated serum uric acid level. Accumulation of uric acid may be due to overproduction of uric acid or reduced excretion of uric acid. Gout may range from asymptomatic to severe and painful inflammatory conditions. A "disease, condition or disorder associated with gout" refers to any condition in a subject where the subject experiences local and/or systemic effects of gout, including inflammation and immune responses, and in which the condition is caused or exacerbated by, or the condition can result in or exacerbate, gout. A gout flare is an attack or exacerbation of gout symptoms, which can happen at any time. Gout flares can include gout flares that occur after the administration of a uric acid lowering therapy. As used herein, the term "chronic refractory gout" refers to symptomatic gout in which conventional urate-lowering therapies are contraindicated or ineffective to control gout and/or hyperuricemia. Chronic refractory gout is often characterized by recurrent gout flares, chronic gout arthropathy with or without bony erosions, visible progressive tophi, physical disability, and/or poor health-related quality of life.

As used herein, the term "hyperuricemia" refers to the presence of high levels of uric acid in the blood. Hyperuricemia may occur because of decreased excretion. Hyperuricemia may also occur from increased production, or a combination of the two mechanisms.

As used herein the term "nucleic acid molecule" refers to a single or double-stranded polymer of deoxyribonucleotide or ribonucleotide bases. It includes chromosomal DNA and self-replicating plasmids, vectors, mRNA, tRNA, siRNA, etc. which may be engineered and from which exogenous polypeptides may be expressed when the nucleic acid is introduced into a cell.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity."

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches. Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, Nucleic Acids Research 16:10881-90 (1988); Huang, et al., CABIOS, 8:155-65 (1992), and Pearson, et al., Methods in Molecular Biology, 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al, Eds., Greene Publishing and Wiley-Interscience, New York (2003). Unless otherwise stated, sequence identity/similarity values provided herein refer to the value obtained using the BLAST 2.0 suite of programs using default parameters. Altschul et al, Nucleic Acids Res. 25:3389-3402 (1997). Software for performing BLAST analyses is publicly available, e.g., through the National Center for Biotechnology-Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always O). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff and Henikoff Proc. Natl. Acad. Sci. USA 89.10915 (1989). In addition to calculating percent sequence identity, the BLAST algorithm also performs a statistical analysis of the similarity between two sequences (see, e.g., Karlin and Altschul, Proc. Natl. Acad. Sci. USA 90:5873-5887 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wootton and Federhen, Comput. Chem., 17:149-163 (1993)) and XNU (Claverie and States, Comput. Chem., 17:191-201 (1993)) low-complexity filters may be employed alone or in combination The term "sequence identity" or "identity" in the context of two nucleic acid or polypeptide sequences is used herein to refer to the residues in the two sequences that are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Myers and Miller, CABIOS, 4:11-17 (1988) e.g., as implemented in the program PC/GENE (Intelligenetics, Mountain View, Calif., USA)

The term "percentage of sequence identity" is used herein mean the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 60% sequence identity, at least 70% sequence identity, at least 80% sequence identity, at least 90% sequence identity, or at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid. Mutations may also be made to the nucleotide sequences of the present proteins by reference to the genetic code, including taking into account codon degeneracy.

As used herein, the term "probiotic composition" refers to a composition comprising probiotic microorganisms and a physiologically acceptable carrier. Typically, a probiotic composition confers a health or wellness benefit on the host subject to whom it is administered.

As used herein, the term "physiologically acceptable" refers to a carrier that is compatible with the other ingredients of a composition and can be safely administered to a subject. Probiotic compositions and techniques for their preparation and use are known to those of skill in the art in light of the present disclosure. For a detailed listing of suitable pharmacological compositions and techniques for their administration one may refer to texts such as Remington's Pharmaceutical Sciences, 17th ed. 1985; Brunton et al., "Goodman and Gilman's The Pharmacological Basis of Therapeutics," McGraw-Hill, 2005; University of the Sciences in Philadelphia (eds.), "Remington: The Science and Practice of Pharmacy," Lippincott Williams & Wilkins, 2005; and University of the Sciences in Philadelphia (eds.), "Remington: The Principles of Pharmacy Practice," Lippincott Williams & Wilkins, 2008.

The probiotic composition may be a liquid formulation or a solid formulation. When the probiotic composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the probiotic composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

As used herein, the probiotic composition could be formulated as a food composition, a dietary supplement, a functional food, a medical food or a nutritional product as long as the required effect is achieved, e.g. treatment or prevention of an alcohol hangover. Said food composition may be chosen from the group consisting of beverages, yogurts, juices, ice creams, breads, biscuits, crackers, cereals, health bars, spreads, gummies and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins. As used herein, the terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation, and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural processes and by entirely synthetic methods, as well. According to some embodiments, the peptide is of any length or size.

As used herein, polypeptides referred to herein as "engineered" refers to polypeptides which have been produced by engineered DNA methodology, including those that are generated by procedures which rely upon a method of artificial recombination, such as the polymerase chain reaction (PCR) and/or cloning into a vector using restriction enzymes.

"Engineered" polypeptides are also polypeptides having altered expression, such as a naturally occurring polypeptide with engineeredly modified expression in a cell, such as a host cell.

As used herein, the terms "subject", "individual", "host", "recipient", "person", and "patient" are used interchangeably herein and refer to any mammalian subject for whom diagnosis, treatment, or therapy is desired, particularly humans. The methods described herein are applicable to both human therapy and veterinary applications. In some embodiments, the subject is a mammal, and in particular embodiments the subject is a human.

As used herein, the phrase "subject in need" refers to a subject that (i) will be administered an engineered microbial cell (or pharmaceutical composition comprising an engineered microbial cell) according to the described invention, (ii) is receiving an engineered microbial cell (or pharmaceutical composition comprising an engineered microbial cell) according to the described invention; or (iii) has received an engineered microbial cell (or pharmaceutical composition comprising an engineered microbial cell) according to the described invention; or (iv) is in need of and/or would benefit from administration of an engineered microbial cell (or pharmaceutical composition comprising an engineered microbial cell) according to the described invention, unless the context and usage of the phrase indicates otherwise As used herein, the term "suppress", "decrease", "interfere", "inhibit" and/or "reduce" (and like terms) generally refers to the act of reducing, either directly or indirectly, a concentration, level, function, activity, or behavior relative to the natural, expected, or average, or relative to a control condition.

As used herein, the terms "therapeutic amount", "therapeutically effective amount", an "amount effective", or "pharmaceutically effective amount" of an active agent (e.g. an engineered microbial cell as described herein) are used interchangeably to refer to an amount that is sufficient to provide the intended benefit of treatment. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods. Additionally, the terms "therapeutic amount", "therapeutically effective amounts" and "pharmaceutically effective amounts" include prophylactic or preventative amounts of the compositions of the described invention. In prophylactic or preventative applications of the described invention, pharmaceutical compositions or medicaments are administered to a patient susceptible to, or otherwise at risk of, a disease, disorder or condition in an amount sufficient to eliminate or reduce the risk, lessen the severity, or delay the onset of the disease, disorder or condition, including biochemical, histologic and/or behavioral symptoms of the disease, disorder or condition, its complications, and intermediate pathological phenotypes presenting during development of the disease, disorder or condition. It is generally preferred that a maximum dose be used, that is, the highest safe dose according to some medical judgment. The terms "dose" and "dosage" are used interchangeably herein.

As used herein the term "therapeutic effect" refers to a consequence of treatment, the results of which are judged to be desirable and beneficial. A therapeutic effect can include, directly or indirectly, the arrest, reduction, or elimination of a disease manifestation. A therapeutic effect can also include, directly or indirectly, the arrest reduction or elimination of the progression of a disease manifestation.

For any therapeutic agent described herein the therapeutically effective amount may be initially determined from preliminary in vitro studies and/or animal models. A therapeutically effective dose may also be determined from human data. The applied dose may be adjusted based on the relative bioavailability and potency of the administered agent. Adjusting the dose to achieve maximal efficacy based on the methods described above and other well-known methods is within the capabilities of the ordinarily skilled artisan. General principles for determining therapeutic effectiveness, which may be found in Chapter 1 of Goodman and Gilman's The Pharmacological Basis of Therapeutics, 12th Edition, McGraw-Hill (New York) (2001) are summarized below.

Pharmacokinetic principles provide a basis for modifying a dosage regimen to obtain a desired degree of therapeutic efficacy with a minimum of unacceptable adverse effects. In situations where the drug's plasma concentration can be measured and related to the therapeutic window, additional guidance for dosage modification can be obtained.

As used herein, the terms "treat", "treating", and/or "treatment" include abrogating, substantially inhibiting, slowing or reversing the progression of a condition, substantially ameliorating clinical symptoms of a condition, or substantially preventing the appearance of clinical symptoms of a condition, obtaining beneficial or desired clinical results. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

Beneficial or desired clinical results, such as pharmacologic and/or physiologic effects include, but are not limited to, preventing the disease, disorder or condition from occurring in a subject that may be predisposed to the disease, disorder or condition but does not yet experience or exhibit symptoms of the disease (prophylactic treatment), alleviation of symptoms of the disease, disorder or condition, diminishment of extent of the disease, disorder or condition, stabilization (i.e., not worsening) of the disease, disorder or condition, preventing spread of the disease, disorder or condition, delaying or slowing of the disease, disorder or condition progression, amelioration or palliation of the disease, disorder or condition, and combinations thereof, as well as prolonging survival as compared to expected survival if not receiving treatment.

As used herein, a "disease or disorder associated with hyperuricemia" refers to a disease or disorder typically associated with elevated levels of uric acid, including, but not limited to a metabolic disorder, e.g., metabolic syndrome, hyperuricemia, gout (e.g., chronic refractory gout, gout tophus and gouty arthritis), tumor-lysis syndrome, Lesch-Nyhan syndrome, cardiovascular disease, diabetes, hypertension, renal disease, or uric acid nephrolithiasis. Such disorders may optionally be acute or chronic. Elevated levels refer to levels that are higher than levels that are considered normal by the American Medical Association, although significantly lower levels are common in vegetarians due to a decreased intake of purine-rich meat.

As used herein, "uric acid", also known as urate (the two terms are used interchangeably herein), refers to an end product of purine metabolism. Humans produce large quantities of uric acid. In human blood, uric acid concentrations between 3.6 mg/dL (~214 pmol/L) and 8.3 mg/dL (~494 pmol/L) (1 mg/dL=59.48 pmol/L) are considered normal by the American Medical Association. Uric acid concentrations can be measured in samples from a subject, e.g., blood or urine samples, using known methods.

As used herein, a "uric acid degrading polypeptide" or "uric acid degrading enzyme" refers to any polypeptide (enzyme) that is involved in catabolizing or degrading uric acid. Examples of uric acid degrading polypeptides include urate oxidase (also known as uricase), allantoinase and allantoicase. Other examples of uric acid degrading polypeptides are described herein and are not intended to be limiting. In an embodiment, a uric acid degrading polypeptide has uric acid as its substrate. In an embodiment, a uric acid degrading polypeptide catalyzes the hydrolysis of uric acid.

As used herein, "uricolytic activity" refers to the activity of degradation of uric acid. Uricolytic activity is measured in units, where one unit of activity is defined as degradation of 1 umol of uric acid per minute. In an embodiment, a uric acid degrading polypeptide alone has uricolytic activity. In an embodiment, two or more uric acid degrading polypeptides contribute to uricolytic activity.

As used herein, the term "variant" refers to a polypeptide which differs from the original protein from which it was derived (e.g., a wild-type protein) by one or more amino acid substitutions, deletions, insertions (i.e., additions), or other modifications. In some embodiments, these modifications do not significantly change the biological activity of the original protein. In many cases, a variant retains at least 10%, 20%, 30%, 40%, 50%, 60%, 70%, 80%, 90%, 95%, or 100% of the biological activity of original protein. The biological activity of a variant can also be higher than that of the original protein. A variant can be naturally-occurring, such as by allelic variation or polymorphism, or be deliberately engineered. For example, a variant may comprise a substitution at one or more amino acid residue positions to replace a naturally-occurring amino acid residue for a structurally similar amino acid residue. Structurally similar amino acids include: (I, L and V); (F and Y); (K and R); (Q and N); (D and E); and (G and A). In some embodiments, variants include (i) polymorphic variants and natural or artificial mutants, (ii) modified polypeptides in which one or more residues is modified, and (iii) mutants comprising one or more modified residues. Variants may differ from the reference sequence (e.g., by truncation, deletion, substitution, or addition) by no more than 1, 2, 3, 4, 5, 8, 10, 20, or 50 residues, and retains (or encodes a polypeptide that retains) a function of the wild-type protein from which they were derived.

The amino acid sequence of a variant is substantially identical to that of the original protein. In many embodiments, a variant shares at least 50%, 60%, 70%, 75%, 80%, 85%, 90%, 91%, 92%, 93%, 94%, 95%, 96%, 97%, 98%, or 99%, or more global sequence identity or similarity with the original protein. Sequence identity or similarity can be determined using various methods known in the art, such as Basic Local Alignment Tool (BLAST), dot matrix analysis, or the dynamic programming method. In one example, the sequence identity or similarity is determined by using the Genetics Computer Group (GCG) programs GAP (Needleman-Wunsch algorithm) The amino acid sequences of a variant and the original protein can be substantially identical in one or more regions, but divergent in other regions. A variant may include a fragment (e.g., a biologically active fragment of a polypeptide). In some embodiments, a fragment may lack up to about 1, 2, 3, 4, 5, 10, 20, 30, 40, 50, or 100 amino acid residues on the N-terminus, C-terminus, or both ends (each independently) of a polypeptide, as compared to the full-length polypeptide.

Engineered Microbial Cells

The present disclosure features engineered microbial cells that are engineered to include at least one exogenous polypeptide comprising a uric acid degrading polypeptide, a uric acid transporter, or both. In some embodiments the microbial cell is a fungal cell.

The present disclosure provides microbial cells that are engineered to degrade uric acid by expression of a uric acid degrading polypeptide, a uric acid transporter, or both a uric acid degrading polypeptide and a uric acid transporter. In some embodiments the microbial cell is a fungal cell.

The engineered cells may be advantageously used to reduce uric acid concentration in the milieu surrounding the cell (e.g., in vitro or in vivo). For example, the engineered cells provided herein may be administered to a subject (e.g., a human subject) to reduce the concentration of uric acid in the subject (e.g., in the intestinal lumen, in the digestive tract, blood, plasma, or serum of the subject, or elsewhere in the subject).

In some embodiments, the disclosure provides an engineered microbial cell comprising at least one (e.g., one, two, three, four, or more) exogenous polypeptides, wherein each exogenous polypeptide may comprise either at least one uric acid degrading polypeptide, at least one uric acid transporter, or both a uric acid degrading polypeptide and a uric acid transporter.

Any condition, disease or disorder in which a reduction of uric acid levels is desired may be treated by administering the engineered cells provided herein.

In some embodiments of any of the aspects herein, the engineered microbial cell is a fungal cell.

Uric Acid

Uric acid is an end product of purine metabolism in humans. Xanthine oxidase oxidizes oxypurines such as xanthine and hypoxanthine to uric acid. In humans and higher primates, uric acid is the final oxidation product of purine catabolismin most other mammals, uricase (uricase) further oxidizes uric acid to 5-hydroxyisourate, which is then further catabolized to allantoin.

In contrast to other mammals, humans lack the capacity to metabolize urate by hepatic uricase, due to mutational silencing of the enzyme. The loss of uricase in higher primates parallels the similar loss of the ability to synthesize ascorbic acid. This may be because in higher primates, uric acid partially replaces ascorbic acid. Both uric acid and ascorbate are strong reducing agents and potent antioxidants. In humans, about half the antioxidant capacity of plasma comes from urate. The urate body pool is about 1-1.2 g, with daily turnover being approximately 0.6-0.7 g. Two-thirds of the newly produced uric acid is excreted in urine, while the remaining one third has a biliary or intestinal elimination or undergoes bacterial uricolysis. It emerges, therefore, that in typical healthy human adults the kidney is the main regulator of uric acid balance.

Humans produce large quantities of uric acid. In human blood, uric acid concentrations between 3.6 mg/dL (–214 pmol/L) and 8.3 mg/dL (–494 pmol/L) (1 mg/dL=59.48 pmol/L) are considered normal by the American Medical Association, although significantly lower levels are common in vegetarians due to a decreased intake of purine-rich meat. Uric acid is a weak organic acid of molecular weight 168 Daltons, with dissociation constants pKal=5.75 and pKa2=10.3 [I]. Therefore, at physiological blood pH, almost all the urate species are in the form of monovalent-anion. The solubility of urate in blood is about 7.0 mg/dL, above which it may deposit in tissues as monosodium-urate-monohydrate.

Only about 4-5% of urate is bound to plasma proteins. Relative to other mammals, humans have high urate levels in plasma, ranging between 3.5 and 7.5 mg/dL (200-450 pmol/L), males having 1.2 times greater urate levels than healthy females.

Disorders associated with high uric acid levels (hyperuricemia) include metabolic syndrome, hyperuricemia, gout (e.g., chronic refractory gout, gout tophus and gouty arthritis), tumor lysis syndrome, Lesch-Nyhan syndrome, cardiovascular disease, diabetes, hypertension, renal disease, metabolic syndrome, or uric acid nephrolithiasis. Such disorders can be treated with an engineered microbial cell of the invention comprising a uric acid degrading polypeptide, a uric acid transporter polypeptide, or an engineered microbial cell comprising a uric acid degrading polypeptide and a uric acid transporter polypeptide, e.g., a composition (e.g., a pharmaceutical composition) comprising said engineered microbial cells, as described herein. In addition, such disorders can be treated by a combination of the engineered microbial cells described herein, and another agent (e.g., a xanthine-oxidase inhibitor and/or a uricosuric and/or an antacid and/or a proton pump inhibitor). The treatment of various diseases and disorders associated with hyperuricemia is described herein.

Uric acid, a weak organic acid, has very low pH-dependent solubility in aqueous solutions. About 70% of urate elimination occurs in urine, the kidney standing as a major determinant of plasma levels. The complex renal handling results in a fractional clearance of less than 10%. Recently identified urate-specific transporter/channels are involved in tubular handling and extracellular transport. Extracellular fluid, rather than urine output, is the main regulator of urate excretion. A number of interfering agents, including widely used drugs such as aspirin, losartan, diuretics, may decrease or increase urate elimination.

Hyperuricemia induced by hypouricosuria often accompanies metabolic syndrome, and insulin resistance has been hypothesized as the common underlying defect. Hyperuricosuria, associated with dehydration or exercise, results in acute uric acid nephropathy, and causes an obstructive acute renal failure (ARF).

Uric Acid Degrading Enzymes

In one aspect, the present disclosure provides a microbial cell engineered to degrade uric acid, comprising an exogenous polypeptide comprising at least one uric acid degrading polypeptide, or a variant thereof. In some embodiments, the microbial cell comprises more than one (e.g., two, three, four, five, or more) exogenous polypeptides, each comprising at least one uric acid degrading polypeptide, or a variant thereof. In some embodiments, the engineered cells described herein comprise more than one type of exogenous polypeptide, wherein each exogenous polypeptide comprises a uric acid degrading polypeptide, and wherein the uric acid degrading polypeptides are not the same (e.g., the uric acid degrading polypeptides may comprise different types of uric acid degrading polypeptides, or variants of the same type of uric acid degrading polypeptide). For example, in some embodiments, the engineered cell may comprise a first exogenous polypeptide comprising a uricase, or a variant thereof, and a second exogenous polypeptide comprising a uric acid degrading polypeptide that is not a uricase. In addition, an exogenous polypeptide may comprise more than one (e.g., one, two, three, four, five, or more) uric acid degrading polypeptide (e.g., two different uricases).

Many uric acid degrading polypeptides are known in the art and may be used as described herein. For example, the uric acid catabolism pathway includes several uric acid degrading enzymes. Urate oxidase is the first of three enzymes to convert uric acid to S-(+)-allantoin (allantoin). After uric acid is converted to 5-hydroxyisourate by urate oxidase, 5-hydroxyisourate (HIU) is converted to 2-oxo-4-hydroxy-4-carboxy-5-ureidoimidazoline (OHCU) by HIU hydrolase, and then to S-(+)-allantoin (allantoin) by 2-oxo-4-hydroxy-4-carboxy-5-ureidoimidazoline decarboxylase (OHCU decarboxylase). Allantoin is converted to allantoate by allantoinase. Allantoate is converted to urea by allantoicase. (Lee et al. 2013 PloS ONE 8 (5):e64292). Any one or more of the enzymes involved in uric acid catabolism (i.e., uric acid degrading polypeptides) can be included in the microbial cells described herein.

In some embodiments, the at least one uric acid degrading polypeptide is any enzyme that is capable of degrading uric acid (e.g., a uricase). In some embodiments, the at least one uric acid degrading polypeptide is any enzyme having uric acid as a substrate. In some embodiments, the at least one uric acid degrading polypeptide is any enzyme that is involved in uric acid catabolism, for example, an enzyme that degrades HIU (e.g., an HIU hydrolase), an enzyme that degrades OHCU (e.g., an OHCU decarboxylase), an enzyme that degrades allantoin (e.g., an allantoinase), or an enzyme that degrades allantoate (e.g., an allantoicase).

In some embodiments, the at least one uric acid degrading polypeptide, or variant thereof, can be derived from any source or species, e.g., mammalian, fungal, plant or bacterial sources, or can be engineeredly engineered. In some embodiments, the uric acid degrading polypeptide can be a chimeric uric acid degrading polypeptide, e.g., derived from two different species.

The exogenous polypeptides included in the engineered cells provided herein may comprise an exogenous polypeptide comprising any uric acid degrading polypeptide. In some embodiments, the uric acid degrading polypeptide comprises a uricase, or a variant thereof.

Uricases (also referred to as urate oxidase), and variants thereof, are described in detail below.

In some embodiments, the uric acid degrading polypeptide comprises or consists of a variant of the wild-type uric acid degrading polypeptide having at least 60%, sequence identity to the amino acid sequence of a corresponding wild-type uric acid degrading polypeptide.

Uricase

The disclosure provides, in one aspect, a microbial cell engineered to degrade uric acid, comprising a first exogenous polypeptide comprising a uricase, or a variant thereof. In some embodiments, the microbial cell comprises more than one (e.g., two, three, four, or five) exogenous polypeptide comprising a uricase.

Uricase (also referred to as UO, urate oxidase, urate: oxygen oxidoreductase (E.C.1.7.3.3)) is an enzyme in the purine degradation pathway that catalyzes the oxidation of uric acid to 5-hydroxyisourate. Uricase is the first in a pathway of three enzymes to convert uric acid to S-(+)-allantoin. After uric acid is converted to 5-hydroxyisourate by urate oxidase, 5-hydroxyisourate (HIU) is converted to 2-oxo-4-hydroxy-4-carboxy-5-ureidoimidazoline (OHCU) by HIU hydrolase, and then to S-(+)-allantoin by 2-oxo-4-hydroxy-4-carboxy-5-ureidoimidazoline decarboxylase (OHCU decarboxylase). Without HIU hydrolase and OHCU decarboxylase, HIU will spontaneously decompose into racemic allantoin.

Uricase is an enzyme endogenous to most mammals, with the exception of humans and certain other primates, and is also found in plants, fungi, yeast, and bacteria. Humans do not produce enzymatically active uricase as a result of mutations in the gene for uricase acquired during the evolution of higher primates (see Wu, et al, J Mol Evol 34:78-84 (1992)). As a consequence, in susceptible individuals, excessive concentrations of uric acid in the blood (hyperuricemia) and in the urine (hyperuricosuria) can lead to gout, disfiguring urate deposits (tophi), renal failure, and other related disorders, as described herein.

An engineered microbial cell of the disclosure may comprise an exogenous polypeptide comprising a uricase, or variant thereof, wherein the uricase is derived from any source(s) known in the art, including mammalian, plant or microbial sources, as well as by engineered technologies.

In some embodiments, the uricase, or uricase variant, is obtained from a fungal (including yeast) source. In some embodiments, the uricase is derived from *Candida utilis* (e.g., as described in Koyama et al, J. Biochem., 120:969-973 (1996)). In some embodiments, the uricase is derived from the fungus *Aspergillus flavus*. In some embodiments, the uricase is the *Aspergillus flavus* uricase contained in rasburicase (ELITEK®; FASTURTEC®, Sanofi Genzyme). Other fungal sources of uricases can include, for example, Schizosaccaromyces (e.g. *Schizosaccharomyces pombe*) or *Zygosaccharomyces* (*Zygosaccharomyces parabailii*).

In some embodiments, the uricase, or uricase variant, is derived from a bacterium, such as *Arthrobacter* (e.g., *Arthrobacter globiformis*) or *Bacillus* (e.g., *Bacillus subtilis*)

In some embodiments, the uricase is a chimeric uricase, in which portions of the uricase are derived from different sources. For example, a portion of the chimeric uricase may be obtained (e.g., derived) from one organism and one or more other portions of the chimeric uricase may be obtained (e.g., derived) from another organism. In some embodiments, a portion of the chimeric uricase is obtained from a pig and another portion of the chimeric uricase is obtained from a baboon. In some embodiments, the chimeric uricase may contain portions of porcine liver and/or baboon liver uricase. For example, the chimeric uricase may comprise all or a portion of a porcine uricase (*Sus scrofa* NP_999435) sequence, wherein the sequence contains the mutations R291K and T301S (PKS uricase). Alternatively, the uricase may comprise all or a portion of a baboon liver uricase (*Papio hamadryas* A36227) sequence in which tyrosine at amino acid residue 97 has been replaced by histidine, whereby the specific activity of the uricase may be increased by at least about 60% as compared to the wild-type uricase from which it was derived (i.e., lacking the amino acid substitution). In some embodiments, the chimeric uricase comprises a chimeric uricase described in U.S. Pat. No. 6,783,965, or comprises pegloticase (KRYSTEXXA®) (Horizon Rheumatology, Inc.). In some embodiments, the chimeric uricase comprises or consists of the amino acid sequence set forth in SEQ ID NO: 4.

Alternatively, in some embodiments, the uricase, or uricase variant, may comprise an invertebrate uricase, a plant uricase, a mammalian uricase.

In some preferred embodiments of the disclosure, the uricase (or variant thereof) comprises or consists of a uricase selected from those set forth in Table 1, below, including a uricase derived from *Candida utilis, Aspergillus flavus, Arthrobacter globiformis*, Baboon/porcine (chimera), *Schizosaccharomyces pombe* (Fission yeast), *Bacillus subtilis*, or *Zygosaccharomyces parabailii*. In some embodiments, the uricase comprises an amino acid sequence of SEQ ID NO:1, SEQ ID NO:2, SEQ ID NO:3, SEQ ID NO:4, SEQ ID NO:5, SEQ ID NO: 6, SEQ ID NO:7, or SEQ ID NO:8.

In some embodiments, the uricase comprises the *Candida utilis* uricase comprising the amino acid sequence set forth in SEQ ID NO: 1. In some embodiments, the uricase comprises the *Aspergillus flavus* uricase comprising the amino acid sequence set forth in SEQ ID NO:2. In some embodiments, the uricase comprises the *Arthrobacter globiformis* uricase comprising the amino acid sequence set forth in SEQ ID NO:3. In some embodiments, the uricase comprises the baboon/porcine chimeric uricase comprising the amino acid sequence set forth in SEQ ID NO:4. In some embodiments, the uricase comprises the *Schizosaccharomyces pombe* (Fission yeast) uricase comprising the amino acid sequence set forth in SEQ ID NO:5. In some embodiments, the uricase comprises the *Bacillus subtilis* uricase comprising the amino acid sequence set forth in SEQ ID NO:6. In some embodiments, the uricase comprises the *Zygosaccharomyces parabailii* uricase comprising the amino acid sequence set forth in SEQ ID NO:7. In some embodiments, the uricase comprises the *Spirosoma* sp. KCTC 42546 uricase comprising the amino acid sequence set forth in SEQ ID NO:8.

In some embodiments, the uricase comprises a variant of a wild-type uricase having at least 60% sequence identity to the amino acid sequence of any one of SEQ ID NO: 1, SEQ ID NO: 2, SEQ ID NO:3, SEQ ID NO:4, SEQ ID NO:5, SEQ ID NO:6, SEQ ID NO:7 or SEQ ID NO: 8. In some embodiments, the uricase variant possesses a function of the uricase from which it was derived (e.g., the ability to catalyze the oxidation of uric acid (urate) to 5-hydroxyisourate).

In a particular embodiment, the uricase consists of the amino acid sequence of any one of SEQ ID NO: 1, SEQ ID NO:2, SEQ ID NO:3, SEQ ID NO:4, SEQ ID NO:5, SEQ ID NO: 6, SEQ ID NO:7 or SEQ ID NO:8.

In some embodiments, the uricase, or variant thereof, is engineered to delete a peroxisome targeting signal (e.g., a native peroxisome targeting signal). In some embodiments, the uricase, or variant thereof, lacks a peroxisome targeting signal.

In general, a variant uricase, from any origin, may be produced, for example, to enhance production of the protein in an engineered cell, to improve turnover/half-life of the protein or mRNA encoding the protein, and/or to modulate (enhance or reduce) the enzymatic activity of the uricase.

The uricase, whatever the source, may also be in a form that is truncated, either at the amino terminal, or at the carboxyl terminal, or at both terminals.

In some embodiments, the invention provides an engineered microbial cell (e.g. an engineered fungal cell) comprising a nucleic acid sequence encoding a uric acid degrading polypeptide as described herein. In some embodiments, the invention provides an engineered microbial cell prepared by using a nucleic acid sequence encoding a uric acid degrading polypeptide (e.g. a uricase) as described herein. In some embodiments, the nucleic acid sequence encodes a uricase as described herein.

In some embodiments, the exogenous polypeptide is a fusion polypeptide comprising a uricase, or a variant thereof, linked to a heterologous protein sequence (e.g., via a linker).

Uric Acid Transporters

In one aspect, the disclosure provides an engineered microbial cell comprising a first exogenous polypeptide comprising a uric acid transporter, or a variant thereof. In some embodiments, the disclosure provides an engineered microbial cell comprising at least one (e.g., one, two, three, four, or more) exogenous polypeptide comprising a uric acid transporter. In some embodiments, the disclosure provides an engineered microbial cell comprising more than one exogenous polypeptide, each comprising a uric acid transporter.

In another aspect, the disclosure provides a microbial cell engineered to degrade uric acid, wherein the cell comprises a first exogenous polypeptide comprising a uric acid degrading polypeptide, e.g., uricase, or a variant thereof, and further comprises a second exogenous polypeptide comprising a uric acid transporter, or a variant thereof.

In yet another aspect, the disclosure provides an engineered cell comprising at least one (e.g., one two, three, four, or more) exogenous polypeptide, wherein the exogenous polypeptide comprises both a uric acid degrading polypeptide (or a variant thereof) and a uric acid transporter (or a variant thereof). Without wishing to be bound by any particular theory, engineered cells comprising an exogenous polypeptide that comprises both a uric acid degrading polypeptide and a uric acid transporter may improve turnover of uric acid (e.g., the catalysis of uric acid) by facilitating the transfer of uric acid from the uric acid transporter to the uric acid degrading polypeptide, thereby microcompartmentalizing the channeling and catalysis of uric acid.

In humans, uric acid transporters regulate uric acid transport in the kidney and thereby regulate plasma uric acid levels (see, So and Thorens, J. Clin. Investigation, 120:1791-1799 (2010)).

Uric acid transporters capable of excreting or re-absorbing uric acid are also expressed in the intestine in humans, and thereby contribute to the regulation of plasma uric acid levels (Xu, et al, Pharmaceutical Biology, 54:3151-3155 (2016)).

In microbes, uric acid transporters contribute to the uptake of uric acid from the environment (See e.g., Pantazopoulou and Diallinas, FEMS Microbiology Reviews, 31:657-675 (2007)). Typically, microbial uric acid transporters enable the use of uric acid as a carbon and/or nitrogen source, and/or as an energy source, enabling growth and division of the microbe (Middelhoven, et al, Antonie van Leeuwenhoek, 50:369-378 (1984)).

Microbial uric acid transporters include archaeal, fungal, and bacterial uric acid transporters. It is expected any microbial organisms whose genome encodes gene products predicted to be involved in uric acid degradation (e.g., uricase) will also have uric acid transporters encoded in their genome. In some prokaryotes, these would be multipass transmembrane proteins encoded in the same operon that encodes the uricase.

Microbial uric acid transporters may be able to transport other purine or purine metabolites (e.g., Xanthine), in addition to uric acid, from outside the cell to inside the cell. These other purines may be transporter in preference to uric acid, with about the same preference, or may be less preferred.

Well characterized microbial uric acid transporters that could be used to engineer microbial cells of the present invention in order to improve uric acid transport and facilitate uric acid degradation include, but are not limited to: *Bacillus subtilis* PucK (genbank accession number O32140) and PucJ (genbank accession number O32139), as described by Schultz et al, Journal of Bacteriology 183:3293-3302 (2001); *Aspergillus nidulans* UapA (genbank accession number Q07307) and UapC (genbank accession number P487777), as described by Diallinas et al, The EMBO journal 17:3827-3837 (1998), Gorfinkiel et al, J Biol Chem 268:23376-23381 (1993), Alguel et al, Nature Communications 7:11336 (2016), and Krypotou and Diallinas, Fungal Genetics and Biology 63:1-8 (2014); *Aspergillus fumigatus* UapA (genbank accession number XP748919), as described by Goudela et al, Fungal Genetics and Biology. 45:459-472 (2008). *Candida albicans* Xut1 (genbank accession number AAX2221), as described by Goudela et al, Molecular membrane biology, 22:263-275 (2005), *Escherichia coli* YgfU (genbank accession number EFJ59310), as described by Papakostas et al, Journal of Biological Chemistry, 287: 15684-15695 (2012).

In some embodiments, a microbial cell of the disclosure comprises an exogenous polypeptide comprising a uric acid transporter selected from the group consisting of *Aspergillus nidulans* UapA, *Aspergillus nidulans* UapC, *Aspergillus fumigatus* UapC, *Candida albicans* Xut1, *Schizosaccharomyces pombe* Q9HE12, *Bacillus subtilis* PucK, *Bacillus subtilis* PucJ, *Escherichia coli* YgfU, *Zygosaccharomyces parabailii* AQZ18664, or *Spirosoma* sp. KCTC 42546 WP_142773020.

In some embodiments, the engineered microbial cell provided herein comprises at least one exogenous polypeptide comprising a uric acid transporter selected from the group consisting of *Aspergillus nidulans* UapA, *Aspergillus nidulans* UapC, *Aspergillus fumigatus* UapC, *Candida albicans* Xut1, *Schizosaccharomyces pombe* Q9HE12, *Bacillus subtilis* Puck, *Bacillus subtilis* PucJ, *Escherichia coli* YgfU, *Zygosaccharomyces parabailii* AQZ18664, *Spirosoma* sp. KCTC 42546 WP_142773020, or a variant thereof. In some embodiments, the uric acid transporter is derived from or is a microbial uric acid transporter.

In some preferred embodiments, the microbial cell of the disclosure comprises an exogenous polypeptide comprising a uric acid transporter selected from those set forth in Table 2, below, comprising or consisting of the amino acid sequence of any one of SEQ ID NO: 9, SEQ ID NO: 10, SEQ ID NO: 11, SEQ ID NO: 12, SEQ ID NO:13, SEQ ID NO:14, SEQ ID NO: 15, SEQ ID NO:16, SEQ ID NO:17, SEQ ID NO: 18, or a variant thereof. In some embodiments, the uric acid transporter comprises a *Aspergillus nidulans* UapA comprising the amino acid sequence set forth in SEQ ID NO: 9. In some embodiments, the uric acid transporter comprises a *Aspergillus nidulans* UapC comprising the amino acid sequence set forth in SEQ ID NO: 10. In some embodiments, the uric acid transporter comprises a *Asper-*

*gillus fumigatus* UapC comprising the amino acid sequence set forth in SEQ ID NO: 11. In some embodiments, the uric acid transporter comprises a *Candida albicans* Xut1 comprising the amino acid sequence set forth in SEQ ID NO:12. In some embodiments, the uric acid transporter comprises a *Schizosaccharomyces pombe* Q9HE12 comprising the amino acid sequence set forth in SEQ ID NO: 13. In some embodiments, the uric acid transporter comprises a *Bacillus subtilis* Puck comprising the amino acid sequence set forth in SEQ ID NO: 14. In some embodiments, the uric acid transporter comprises a *Bacillus subtilis* PucJ comprising the amino acid sequence set forth in SEQ ID NO: 15. In some embodiments, the uric acid transporter comprises a *Escherichia coli* YgfU comprising the amino acid sequence set forth in SEQ ID NO: 16. In some embodiments, the uric acid transporter comprises a *Zygosaccharomyces parabailii* AQZ18664 comprising the amino acid sequence set forth in SEQ ID NO: 17. In some embodiments, the uric acid transporter comprises a *Spirosoma* sp. KCTC 42546 WP_142773020 comprising the amino acid sequence set forth in SEQ ID NO: 18.

In some embodiments, the uric acid transporter comprises a variant of a wild-type uric acid transporter having at least 60% sequence identity to the amino acid sequence of any one of SEQ ID NO: 9, SEQ ID NO: 10, SEQ ID NO: 11, SEQ ID NO: 12, SEQ ID NO:13, SEQ ID NO: 14, SEQ ID NO:15, SEQ ID NO:16 or SEQ ID NO:17, or SEQ ID NO: 18. In some embodiment the variant of the uric acid transporter possesses a function of the wild-type uric acid transporter from which it was derived (e.g., the ability to t uric acid).

In a particular embodiment, the uric acid transporter consists of the amino acid sequence of any one of SEQ ID NO: 9, SEQ ID NO: 10, SEQ ID NO: 11, SEQ ID NO: 12, SEQ ID NO: 13, SEQ ID NO:14, SEQ ID NO:15, SEQ ID NO: 16, SEQ ID NO:17, or SEQ ID NO: 18.

In general, a variant uric acid transporter, may be produced, for example, to enhance production of the protein in an engineered cell, to improve turnover/half-life of the protein or mRNA encoding the protein, and/or to modulate (enhance or reduce) the activity of the uric acid transporter. The uric acid transporter may also be in a form that is truncated, either at the amino terminal, or at the carboxyl terminal, or at both terminals.

In some embodiments, the invention provides an engineered microbial cell (e.g. an engineered fungal cell) comprising a nucleic acid sequence encoding a uric acid transporter as described herein. In some embodiments, the invention provides an engineered microbial cell prepared by using a nucleic acid sequence encoding a uric acid transporter as described herein. In some embodiments, the nucleic acid sequence encodes a uric acid transporter (*Aspergillus nidulans* UapA, *Aspergillus nidulans* UapC, *Aspergillus fumigatus* UapC, *Candida albicans* Xut1, *Schizosaccharomyces pombe* Q9HE12, *Bacillus subtilis* PucK, *Bacillus subtilis* PucJ, *Escherichia coli* YgfU, *Zygosaccharomyces parabailii* AQZ18664, or *Spirosoma* sp. KCTC 42546 WP_142773020) as described herein.

Polypeptides and Nucleic Acids

In one aspect, the disclosure provides isolated uric acid degrading polypeptides (e.g., uricase) and uric acid transporters described herein. In some embodiments, the uric acid degrading polypeptides comprise an amino acid sequence having at least 60% sequence identity to the amino acid sequences of a uric acid degrading polypeptide described herein. In some embodiments, the uric acid transporters comprise an amino acid sequence having at least 60% sequence identity to the amino acid sequences of a uric acid transporter described herein. In some embodiments, the uric acid degrading polypeptides and uric acid transporters are engineered. Methods for producing engineered proteins are known in the art and described herein.

In another aspect, the disclosure provides nucleic acids (e.g., DNA or RNA (e.g., mRNA)) encoding a uric acid degrading polypeptide described herein. In another aspect, the disclosure provides nucleic acids (e.g., DNA or RNA (e.g., mRNA)) encoding a uric acid transporter described herein. In some embodiments, the nucleic acids are codon-optimized for expression in a desired cell type (e.g., a bacterial or fungal or archaeal cell).

Furthermore, any of the genes encoding the foregoing enzymes (or any others mentioned herein (or any of the regulatory elements that control or modulate expression thereof)) may be optimized by genetic/protein engineering techniques, such as directed evolution or rational mutagenesis, which are known to those of ordinary skill in the art. Such action allows those of ordinary skill in the art to optimize the enzymes for expression, activity, stability, or other desirable parameters.

Populations of Engineered Microbial Cells

In one aspect, the invention features cell populations comprising the engineered microbial cells of the invention, e.g., a plurality or population of the microbial cells. In various embodiments, the engineered microbial cell population comprises predominantly fungal cells.

It will be understood that during the preparation of the engineered microbial cells of the invention, some fraction of cells may not contain the exogenous polypeptide or be transformed to express an exogenous polypeptide. Accordingly, in some embodiments, a population of engineered microbial cells provided herein comprises a mixture of engineered microbial cells and unmodified microbial cells, i.e., some fraction of cells in the population will not comprise, present, or express an exogenous polypeptide.

Urate Consumption Assays

Urate consumption assays can be used to quantify uptake and/or biodegradation of uric acid from media surrounding intact cells.

The reduction of absorbance at wavelengths between 290 and 295 nm has been used to measure uric acid concentrations by converting urate into 5-hydroxyisourate through addition of purified uricase enzyme (Prætorius and Poulsen, Scandinavian Journal of Clinical and Laboratory Investigation, 5273-280 (1953)). Urate consumption by intact cells can be measured by quantifying growth of microbial strains on culture media containing uric acid as the sole nitrogen source as compared to growth on culture media containing alternative nitrogen sources, as outlined for example in Martzoukou et al, J. Molec. Biol. 427:2679-2696 (2015), or in Schultz et al, Journal of Bacteriology 183:3293-3302 (2001). Assays that quantify urate consumption by intact cells can also rely on the use of expensive and hazardous radiolabeled compounds, e.g., $^{3}$H-labeled or $^{14}$C-labeled uric acid, as outlined for example in Goudela et al, Molecular membrane biology, 22.263-275 (2005).

The invention contemplates a much simpler, faster, easier and safer assay that quantifies uric acid consumption by intact cells by spectrophotometrically tracking depletion of uric acid in medium or buffer surrounding said cells. Intact cells require a uric acid transporter to transport urate into cells, where it is broken down by a uricase enzyme. Both a functional uric acid transporter and a functional uricase are required. Uric acid is depleted over time in a culture medium or buffer containing uric acid if intact cells are added that have the ability to take up uric acid from the culture medium or buffer and break it down to allow continued importation of uric acid from the medium or buffer surrounding cells into said intact cells. The rate of uric acid depletion is dependent on the rate of uric acid consumption by the intact cells, allowing uric acid consumption to be quantified. The uric acid concentration can be tracked spectrophotometrically by measuring absorbance at a wavelength where urate strongly absorbs, preferably between 275 nm and 350 nm, most preferably 293 nm, following separation of the intact cells from the medium or buffer.

Methods of Obtaining Engineered Microbial Cells

Various methods of obtaining genetically engineered microbial cells, e.g., fungal cells, are contemplated by the present disclosure.

Methods of manufacturing microbial cells comprising an exogenous agent (e.g., a polypeptide) are described, e.g., in Yeast Protocols Handbook, Clontech Laboratories, Mountain View, USA, 2009.

In one aspect, the disclosure features an engineered microbial cell (e.g., engineered fungal cell), comprising a first exogenous polypeptide comprising a uric acid degrading polypeptide, or a variant thereof, produced by a process comprising introducing an exogenous nucleic acid encoding the first exogenous polypeptide into a microbial cell; and culturing the microbial cell under conditions suitable for production of the first exogenous polypeptide.

In another aspect, the disclosure features an engineered microbial cell (e.g., engineered fungal cell), comprising a first exogenous polypeptide comprising a uric acid transporter, or a variant thereof, produced by a process comprising introducing an exogenous nucleic acid encoding the first exogenous polypeptide into a microbial cell; and culturing the microbial cell under conditions suitable for production of the first exogenous polypeptide.

In another aspect, the disclosure features an engineered microbial cell (e.g., engineered fungal cell), comprising a first exogenous polypeptide comprising a uric acid degrading polypeptide, or a variant thereof, and a second exogenous polypeptide comprising a uric acid transporter, or a variant thereof, produced by a process comprising introducing an exogenous nucleic acid encoding the first exogenous polypeptide into a microbial cell; introducing an exogenous nucleic acid encoding the second exogenous polypeptide into a microbial cell; and culturing the microbial cell under conditions suitable for production of the first exogenous polypeptide and the second exogenous polypeptide.

In some embodiments, the uric acid degrading polypeptide is a uricase, or a variant thereof. In some embodiments, more than one uric acid degradation polypeptide, or variant thereof, may be combined in one or more microbial cells, as described herein.

The processes of making the engineered microbial cells are described in more detail below.

Probiotic Cells

Provided herein are engineered microbial cells, and methods of making the engineered microbial cells.

As used herein, the term "probiotic" refers to a live microbial cells that, when administered in adequate amounts, may or may not confer a health benefit on the host, and do not exert harmful effects on the host. Probiotic cells may be referred to or sold using alternative designations, for example as "nutraceuticals", "dietary supplements", "supplements", "food additives", "dietary ingredients", "food ingredients", and "ingredients".

The engineered microbial cells can be probiotic cells. The engineered probiotic cells can be eukaryotic, e.g., fungal, e.g. *Saccharomyces boulardii*, e.g., *Candida utilis*, e.g. from the genus *Kluyveromyces*, bacterial, e.g. from the genus *Lactobacillus*, or can be archeal. The engineered microbial cell can be from the genus *Escherichia*, e.g., *Escherichia coli* Nissle. The engineered microbial cell can be from the genus *Bacteroides*, e.g., *Bacteroides ovatus, Bacteroides fragilis, Bacteroides thetaiotaomicron, Bacteroides vulgatus, Bacteroides ovatus*, or *Bacteroides uniformis*. The engineered microbial cell can be from the genus *Clostridium*. The engineered microbial cell can be from the genus *Bacillus*.

Expression of Exogenous Polypeptides

In some embodiments, the engineered microbial cells described herein are generated by contacting a suitable isolated cell, e.g., a microbial cell, with an exogenous nucleic acid encoding a polypeptide of the disclosure (e.g., a uricase and/or a uric acid transporter).

In some embodiments, the exogenous polypeptide is encoded by a DNA, which is contacted with a microbial cell. In some embodiments, the exogenous polypeptide is encoded by an RNA, which is contacted with a microbial cell.

An exogenous polypeptide may be expressed from a transgene introduced into an microbial cell, e.g. by electroporation, chemical or polymeric transfection; an exogenous polypeptide that is over-expressed from the native locus by the introduction of an external factor, e.g., a transcriptional activator, transcriptional repressor, or secretory pathway enhancer.

In certain embodiments, the introducing step comprises electroporation. In some embodiments, the introducing step comprises chemical transformation (e.g., PEG-mediated transformation).

In some embodiments, the introducing step comprises introducing the first exogenous nucleic acid encoding the first exogenous polypeptide by electroporation of an episomal plasmid.

Exogenous polypeptides (e.g., a uricase or a uric acid transporter) can be introduced by transfection of single or multiple copies of genes, transformation, or electroporation in the presence of DNA or RNA. Methods for expression of exogenous proteins in microbial cells are well known in the art.

In some embodiments, when there is more than one polypeptide (e.g., two or more), the polypeptides may be encoded in a single nucleic acid, e.g., a single vector. When both the uricase and uric acid transporter are encoded in the same vector, there are multiple possible sub-strategies useful for this method of co-expression. In some embodiments, the single vector has a separate promoter for each gene, or any other suitable configuration. In some embodiments, the engineered nucleic acid comprises a gene encoding a first exogenous polypeptide, wherein the first exogenous polypeptide is uricase, or a variant thereof, and a gene encoding a second exogenous polypeptide, wherein the second exogenous polypeptide is a uric acid transporter, or a variant thereof.

For dual expression via 2 promoters, the PGK1 promoter may be used as promoter #1 and the GPD (TDH3) promoter as promoter #2, although the disclosure is not to be limited by these two exemplary promoters. Another strategy is to express both uricase and uric acid transporter proteins by inserting an internal ribosome entry site (IRES) between the two genes. Still another strategy is to express uricase and uric acid transporter as direct peptide fusions separated by a linker.

In some embodiments, the two or more polypeptides are encoded in two or more nucleic acids, e.g., each vector encodes one of the polypeptides.

In certain embodiments, the expression vector comprises a promoter selected from the group consisting of *Saccharomyces* PDC1p, FBA1p, TEF2p, PGK1p, PGI1p, ADH1p, TDH2p, PYK1p, ENO2p, GPDp, GPM1p, TPI1p, TEF1p, and HXT7p promoters, as described in Sun et al, Biotechnology and Bioengineering 109:2082-2092 (2012).

Nucleic acids such as DNA expression vectors or mRNA for producing the exogenous polypeptides may be introduced into progenitor cells that are suitable to produce the exogenous polypeptides described herein. In some instances, the expression vectors can be designed such that they can incorporate into the genome of cells by homologous or non-homologous recombination by methods known in the art.

According to some embodiments, one or more exogenous polypeptides may be cloned into plasmid constructs for transfection. Methods for transferring expression vectors or genes into cells that are suitable to produce the engineered microbial cells described herein include, but are not limited to, transformation, chemical or polymeric transformation.

According to some embodiments, engineered DNA encoding each exogenous polypeptide may be cloned into a suitable integrative plasmid for integration into microbial cells. In some embodiments, the episomal or integrative vector comprises DNA encoding a single exogenous polypeptide for integration into microbial genomes. For example, in some embodiments, the episomal or integrative vector comprises DNA encoding a uricase polypeptide for integration into microbial cells. In some embodiments, the episomal or integrative vector comprises DNA encoding a uric acid transporter for integration into microbial cells. In other embodiments, the episomal or integrative vector comprises two, three, four or more exogenous polypeptides as described herein for integration into microbial cells. For example, in some embodiments, the episomal or integrative vector comprises DNA encoding a uricase polypeptide and a uric acid transporter polypeptide for integration into microbial cells. According to some embodiments, engineered DNA encoding the one or more exogenous polypeptides may be cloned into a plasmid DNA construct encoding a selectable trait, such as an antibiotic resistance gene or an auxotrophy complementation gene. According to some embodiments, engineered DNA encoding the exogenous polypeptides may be cloned into a plasmid construct that is adapted to stably express each engineered protein in the microbial cells.

In some embodiments, the engineered microbial cell is generated by contacting a suitable isolated microbial precursor cell with an exogenous nucleic acid encoding one or more exogenous polypeptides. In some embodiments, the exogenous polypeptide is encoded by a DNA, which is contacted with a microbial precursor cell.

The one or more exogenous polypeptides may be genetically introduced into a microbial cell (e.g., fungal cell), using a variety of DNA techniques, including transient or stable transfections and gene transfer approaches. The exogenous polypeptides may be expressed on the surface and/or in the cytoplasm and/or in other subcellular compartments of the engineered microbial cells.

Optionally, electroporation methods may be used to introduce a plasmid vector into suitable microbial cells. Electroporation allows for the introduction of various molecules into the cells including, for example, DNA and RNA. As such, microbial cells are isolated and cultured as described herein.

Electroporation may be done using, for example, a MicroPulser Electroporator or Gene Pulser (Bio-Rad), as described in Benatuil et al, Protein Eng Des Sel. 23:155-159 (2010), Supplementary Methods.

Microbial cells may be transformed with an integrative expression vector which is unable to self-replicate. Alternatively, microbial cells may be transformed with a vector which may persist as autonomously replicating genetic units without integration into chromosomes. These vectors (e.g., plasmids) may exploit genetic elements derived from plasmids that are normally extrachromosomally replicating in cells. Such plasmids include, for example, the episomal *Saccharomyces* 2 micron plasmid. Self-replicating vectors may also include chromosomal elements that allow for independent replication. Such self-replicating vectors exploit the cell's endogenous replication and chromosome segregation machinery to persist like mini-chromosomes. Chromosomal elements that can be used to produce self-replicating vectors include, for example, an autonomously replicating sequence (ARS) and a centromere (CEN), as described for example in Gnügge and Rudolf, Yeast 34:205-221 (2017).

Exogenous nucleic acids encoding one or more exogenous polypeptides may be assembled into expression vectors by standard molecular biology methods known in the art, e.g., restriction digestion, overlap-extension PCR, and Gibson assembly.

In certain embodiments, the engineered microbial cell is a microbial cell that presents a first exogenous polypeptide that is conjugated with a second exogenous polypeptide.

Methods of Use and Treatment

The present disclosure provides methods of treating or preventing hyperuricemia in a subject, comprising administering to the subject the engineered microbial cell as described herein, in an amount effective to treat or prevent hyperuricemia in the subject.

Methods of administering engineered microbial cells comprising (e.g., presenting) exogenous agents (e.g., polypeptides) are described, e.g., in Govender et al, Aaps PharmSciTech 15:29-43 (2014).

In embodiments, the engineered microbial cells described herein (e.g., engineered fungal cells) are orally administered to a subject, e.g., a mammal, e.g., a human. The methods described herein are applicable to both human therapy and veterinary applications.

In one aspect, the present disclosure provides a method of treating or preventing hyperuricemia in a subject, comprising orally administering to the subject an engineered microbial cell as described herein (e.g. an engineered microbial cell comprising a uric acid degrading polypeptide, e.g., uricase, an engineered microbial cell comprising a uric acid transporter, an engineered microbial cell comprising a uric acid degrading polypeptide, e.g., uricase and a uric acid transporter), in an amount effective to treat or prevent hyperuricemia in the subject.

The normal range of uric acid in blood is between 3.4 mg/dL and 7.0 mg/dL in men, between 2.4 mg/dL and 6.0 mg/dL in premenopausal women, and from 2.5 mg/dL to 5.5 mg/dL in children. Urate crystal formation/precipitation typically occurs in men at levels of 6.6 mg/dL or higher and in women at levels of 6.0 mg/dL or higher. Also, what may be in the normal range for the population as a whole may be elevated for the individual.

Cardiovascular and other consequences of elevated uric acid can occur with blood levels well within these "normal" ranges. Therefore, a diagnosis of hyperuricemia is not necessarily a prerequisite for the beneficial effects of the engineered microbial cells of the invention.

In some embodiments, the subject has a serum urate level greater than about 6.8 mg/dl prior to administering the engineered microbial cell.

In some embodiments, the methods described herein comprise selecting a subject having a serum urate level greater than about 6.8 mg/dl, and administering an engineered microbial cell described herein.

In some embodiments, the subject has a serum urate level less than about 6.8 mg/dl, after administering the engineered microbial cell. In some embodiments, the subject has a serum urate level of about 6.0 mg/dl after administering the engineered microbial cell, for example 6.0, 5.9, 5.8, 5.7, 5.6, 5.5, 5.4, 5.3, 5.2, 5.1, 5.1 mg/dL or less, after administering the engineered microbial cell.

Hyperuricemia

Hyperuricemia is the presence of high levels of uric acid in the blood. Hyperuricemia may occur because of decreased excretion. Hyperuricemia may also occur from increased production, or a combination of the two mechanisms. Underexcretion accounts for the majority of cases of hyperuricemia. Overproduction accounts for only a minority of patients presenting with hyperuricemia. Consumption of purine-rich diets is one of the main causes of hyperuricemia. Other dietary causes are ingestion of high protein and fat, and starvation. Starvation results in the body metabolizing its own muscle mass for energy, in the process releasing purines into the bloodstream. Purine bases composition of foods varies. Foods with higher content of purine bases adenine and hypoxanthine are suggested to be more potent in exacerbating hyperuricemia.

Humans lack uricase, an enzyme which degrades uric acid. Increased levels predispose for gout and, if very high, renal failure. Apart from normal variation (with a genetic component), tumor lysis syndrome produces extreme levels of uric acid, mainly leading to renal failure. The Lesch-Nyhan syndrome is also associated with extremely high levels of uric acid. The Metabolic syndrome often presents with hyperuricemia, while a hyperuricemic syndrome is also common in Dalmatian dogs. A uric acid degrading polypeptide, e.g., uricase, described herein and a pH increasing agent, alone or in combination with another agent, e.g., another agent described herein, can be used to treat hyperuricemia.

Asymptomatic hyperuricemia is the term for an abnormally high serum urate level, without gouty arthritis or nephrolithiasis. Hyperuricemia is defined as a serum urate concentration greater than about 6.8 mg per dL, the approximate level at which urate is supersaturated in plasma. Serum uric acid levels above 360 μM are considered pathogenic.

Although gouty arthritis characteristically occurs in patients with hyperuricemia, hyperuricemia is not necessarily associated with clinical gout. Researchers from the Normative Aging Study followed 2,046 initially healthy men for 15 years by taking serial measurements of serum urate levels. The five-year cumulative incidence rates of gouty arthritis were 2.0 percent for a serum urate level of 8.0 mg per dL (475 pmol per L) or lower, 19.8 percent for urate levels from 9.0 to 10.0 mg per dL (535 to 595 pmol per L) and 30 percent for a serum urate level higher than 10 mg per dL (595 pmol per L). Hyperuricemia predisposes patients to both gout and nephrolithiasis, but therapy is occasionally not warranted in the asymptomatic patient. Recognizing hyperuricemia in the asymptomatic patient, however, provides the physician with an opportunity to modify or correct underlying acquired causes of hyperuricemia.

Hyperuricosuria

Hyperuricosuria is defined as urinary excretion of uric acid greater than 800 mg/d in men and greater than 750 mg/d in women. This may be due to either excess dietary intake of purine-rich foods or endogenous uric acid overproduction. Hyperuricosuria may be associated with hyperuricemia.

Gout

Gout is a condition that results from crystals of uric acid depositing in tissues of the body. Gout is characterized by an overload of uric acid in the body and recurring attacks of joint inflammation (arthritis). Chronic gout can lead to deposits of hard lumps of uric acid in and around the joints, decreased kidney function, and kidney stones.

Gout is generally divided into four categories based upon progressively more severe symptoms:

Asymptomatic. Elevated uric acid levels in the blood, but no overt symptoms.

Acute gouty arthritis: Sudden onset of symptoms, often in a single joint (commonly a big toe), and then involving other joints. Symptoms include pain, swelling, redness and fever. Intercritical gout: Asymptomatic phases between gout attacks.

Chronic tophaceous gout: A chronic condition that may include frequent attacks, constant mild pain and inflammation of joints, destruction of cartilage and bone, development of uric acid crystal deposits, kidney dysfunction and kidney stones.

Excess serum accumulation of uric acid can lead to a type of arthritis known as gout (gouty arthritis). Gouty arthritis is usually an extremely painful attack with a rapid onset of joint inflammation. The joint inflammation is precipitated by deposits of uric acid crystals in the joint fluid (synovial fluid) and joint lining (synovial lining). Intense joint inflammation occurs as white blood cells engulf the uric acid crystals and release chemicals of inflammation, causing pain, heat, and redness of the joint tissues.

The small joint at the base of the big toe is the most common site of an acute gout attack. Other joints that can be affected include the ankles, knees, wrists, fingers, and elbows. Acute gout attacks are characterized by a rapid onset of pain in the affected joint followed by warmth, swelling, reddish discoloration, and marked tenderness.

Hyperuricemia and gout are particularly significant issues in organ transplant recipients (Stamp et al, Drugs 65:2593-2611 (2005)). Uric acid is often elevated in patients with renal transplants, and common immunosuppressive drugs such as cyclosporine can cause particularly severe hyperuricemia. In transplant patients, allopurinol is contra indicated due to interactions with some immunosupressants such as azathioprine, and due to bone marrow failure caused by the combination. Furthermore, elevated uric acid may contribute to graft failure (Armstrong et al, Transplantation 80:1565-1571 (2005).

Lesch-Nyhan Syndrome

Lesch-Nyhan syndrome (LNS), also known as Nyhan's syndrome, is a rare, inherited disorder caused by a deficiency of the enzyme hypoxanthine-guanine phosphoribosyltransferase (HGPRT). LNS is an X-linked recessive disease: the gene is carried by the mother and passed on to her son. LNS is present at birth in baby boys. Patients have severe mental and physical problems throughout life. The lack of HGPRT causes a build-up of uric acid in all body fluids, and leads to problems such as severe gout, poor muscle control, and moderate mental retardation, which appear in the first year of life.

Abnormally high uric acid levels can cause sodium uric acid crystals to form in the joints, kidneys, central nervous system and other tissues of the body, leading to gout-like swelling in the joints and severe kidney problems. Neurological symptoms include facial grimacing, involuntary writhing, and repetitive movements of the arms and legs similar to those seen in Huntington's disease. The direct cause of the neurological abnormalities remains unknown. Because a lack of HGPRT causes the body to poorly utilize vitamin B 12, some boys may develop a rare disorder called megaloblastic anemia.

The symptoms caused by the buildup of uric acid (arthritis and renal symptoms) respond well to treatment with drugs such as allopurinol that reduce the levels of uric acid in the blood. There is no cure, but many patients live to adulthood. LNS is rare, affecting about one in 380,000 live births.

Uric Acid Nephrolithiasis

Uric acid stones account for about 5% to 10% of all kidney stones in Western countries and Japan. The stones can be composed of uric acid alone or admixed with calcium oxalate. Sex distribution indicates a male to female ratio of more than one, which tends to diminish in the post-menopausal age. Kidney stones, also called renal calculi, are solid concretions (crystal aggregations) of dissolved minerals in urine; calculi typically form inside the kidneys or ureters. The terms nephrolithiasis and urolithiasis refer to the presence of calculi in the kidneys and urinary tract, respectively.

The formation of uric acid stones is associated with conditions that cause high blood uric acid levels, such as gout, leukemias/lymphomas treated by chemotherapy (secondary gout from the death of leukemic cells), and acid/base metabolism disorders where the urine is excessively acid resulting in uric acid precipitation.

Vascular Conditions

Diseases related to elevated soluble uric acid often involve vascular problems: hypertension (Sundstrom et al, Hypertension 45:28-33 (2005)), prehypertension (Syamela et al, J Hypertens 25:1583-1589 (2007)), atherosclerosis (Ishizaka et al, Arterioscler Thromb Vasc Biol 5:1038-1044 (2005)), peripheral artery disease (Shankar, et al, Atherosclerosis 196:749-755 (2007)), vascular inflammation (Zoccali et al, J Am Soc Nephrol. 17:1466-1471 (2006)), heart failure (Strasak et al, Clin Chem. 54:273-284 (2008); Pascual-Figal et al, Eur J Heart Fail 9:518-524 (2006); Çengel et al, Acta Cardiol 60:489-492 (2005)), myocardial infarctions (Strasak et al, Clin Chem. 54:273-284 (2008); (Bos et al, Stroke 37:1503-1507 (2006)), renal dysfunction (Cirillo et al, J Am Soc Nephrol 17 (12 Suppl 3): S165-S168 (2006)), and strokes (Bos et al, Stroke 37:1503-1507 (2006)). Uric acid directly causes endothelial dysfunction (Kanellis et al, Semin Nephrol. 25:39-42 (2005); Khosla et al, Kidney Int. 67:1739-1742 (2005)). In children, early-onset essential hypertension is associated with elevated serum uric acid, and reduction of uric acid with allopurinol reduced blood pressure in a small cohort of patients (Feig and Johnson, J Ren Nutrition 17:79-83 (2007)). Hyperuricemia is an independent risk factor in all of these conditions.

Diabetes

Elevated levels of uric acid are associated with prediabetes, insulin resistance, the development of Type 2 diabetes, and an increased probability of a variety of undesirable conditions in people with diabetes, such as peripheral artery disease, strokes, and increased mortality risk. Studies have shown that high serum uric acid is associated with higher risk of type 2 diabetes independent of obesity, dyslipidemia, and hypertension. Serum uric acid is a strong predictor of stroke in patients with non-insulin dependent diabetes mellitus.

Metabolic Syndrome

Metabolic syndrome is a cluster of conditions that occur together, increasing the risk of heart disease, stroke and diabetes. Metabolic syndrome involves having several disorders related to metabolism at the same time, including: obesity; elevated blood pressure; an elevated level of triglycerides; a low level of high-density lipoprotein (HDL) cholesterol; high blood pressure and/or high insulin levels. Hyperuricemia is associated with components of metabolic syndrome, and may play a pathogenic role in the metabolic syndrome.

Inflammatory Responses

Elevated soluble uric acid is also associated with or directly induces inflammatory responses. For example, uric acid is transported into vascular smooth muscle cells via organic acid transporters, especially the uric acid transporter URAT1, and then stimulates vascular smooth muscle cells to produce C-reactive protein, MCP-1 and other cytokines, thereby stimulating proliferation and other changes associated with atherosclerosis (Price et al, J Am Soc Nephrol 17:1791-1795 (2006); Kang et al, Am J Nephrol. 25:425-433 (2005); Yamamoto et al, Hypertens. Res. 29:915-921 (2006), stimulates human mononuclear cells to produce IL-1 b, IL-6 and TNF-a, causes marked increases in TNF-a when infused into mice, activates endothelial cells and platelets, and increases platelet adhesiveness (Coutinho et al, Amer. J. Hypertens. 20:83-89 (2007); Levya et al, Eur. Heart J. 19:1814-1822 (1998)). Uric acid has also been shown to inhibit bioavailability of endothelial nitric oxide and activate the renin-angiotensin system.

Cognitive Impairment

Hyperuricemia is also associated with cognitive impairment and other forms of central nervous system dysfunction.

(Schretlen et al, Neuropsychology 21:136-140 (2007); Watanabe et al, J. Health Science 52:730-737 (2006)).

An engineered microbial cell as described herein (e.g. an engineered microbial cell comprising a uric acid degrading polypeptide, e.g., uricase, an engineered microbial cell comprising a uric acid transporter, or an engineered microbial cell comprising a uric acid degrading polypeptide, e.g., uricase and a uric acid transporter), alone or in combination with another agent, e.g., another agent described herein, can be used to treat hyperuricemia, asymptomatic hyperuricemia, hyperuricosuria, gout, refractory gout, Lesch-Nyhan syndrome, kidney stones and nephrolithiasis, e.g., kidney stones and/or nephrolithiasis caused by, or associated with, elevated uric acid concentrations, cardiovascular disease caused by, or associated with, elevated uric acid concentrations, diabetes caused by, or associated with, elevated uric acid concentrations, metabolic syndrome caused by, or associated with, elevated uric acid concentrations, inflammatory responses caused by, or associated with, elevated uric acid concentrations, cognitive impairment caused by, or associated with, elevated uric acid concentrations.

In some embodiments, a subject has refractory gout if they have demonstrated contraindication to allopurinol, or have a medical history of failure to normalize uric acid (e.g., to less than 6 mg/dL) with at least 3 months of allopurinol treatment at the maximum medically appropriate dose.

Dosing

In one embodiment, a dose of engineered microbial cells as described herein comprises about 10^6-10^12 engineered microbial cells per dose.

In one example, administration of the engineered microbial cell is initiated at a dose which is minimally effective, and the dose is increased over a pre-selected time course until a positive effect is observed. Subsequently, incremental increases in dosage are made limiting to levels that produce a corresponding increase in effect while taking into account any adverse effects that may appear.

Any one of the doses provided herein for an engineered microbial cell as described herein can be used in any one of the methods or kits provided herein. Generally, when referring to a dose to be administered to a subject the dose is a label dose. Thus, in any one of the methods provided herein the dose(s) are label dose(s).

Also provided herein are a number of possible dosing schedules. Accordingly, any one of the subjects provided herein may be treated according to any one of the dosing schedules provided herein. As an example, any one of the subject provided herein may be treated with an engineered microbial cell as described herein. In certain embodiments, the engineered microbial cell comprises a first exogenous polypeptide comprising uricase, or a variant thereof, and a second exogenous polypeptide comprising a uric acid transporter, or a variant thereof.

Each dose of engineered microbial cells can be administered at intervals such as thrice, twice, or once daily, once weekly, twice weekly, once monthly, or twice monthly. In some embodiments, a subject is dosed on a monthly dosing schedule.

The mode of administration for the composition(s) of any one of the treatment methods provided may be by oral administration, such as a capsule containing (freeze-) dried microbes, a powder containing (freeze-) dried microbes, or a suspension containing live microbes, prior to, during, or after a meal. Additionally, any one of the methods of treatment provided herein may also include administration of an additional therapeutic, as described in more detail below. The administration of the additional therapeutic may be according to any one of the applicable treatment regimens provided herein.

In some embodiments of any one of the methods provided herein, the level of uric acid is measured in the subject at one or more time points before, during and/or after the treatment period.

The methods described herein are intended for use with any subject that may experience the benefits of these methods. Thus, "recipients" "subjects," "patients," and "individuals" (used interchangeably) include humans as well as non-human subjects, particularly domesticated animals. Subjects provided herein can be in need of treatment according to any one of the methods or compositions or kits provided herein. Such subjects include those with elevated serum uric acid levels or uric acid deposits. Such subjects include those with hyperuricemia. It is within the skill of a clinician to be able to determine subjects in need of a treatment as provided herein.

In some embodiments, the subject and/or animal is a mammal, e g., a human. In some embodiments, the human is a pediatric human. In other embodiments, the human is an adult human. In other embodiments, the human is a geriatric human. In other embodiments, the human may be referred to as a patient.

In other embodiments, the subject is a non-human animal, and therefore the disclosure pertains to veterinary use. In a specific embodiment, the non-human animal is a household pet. In another specific embodiment, the non-human animal is a livestock animal. In certain embodiments, the subject is a human cancer patient that cannot receive chemotherapy, e.g. the patient is unresponsive to chemotherapy or too ill to have a suitable therapeutic window for chemotherapy (e.g. experiencing too many dose- or regimen-limiting side effects). In certain embodiments, the subject is a human subject having gout or another disease or condition associated with hyperuricemia. In other certain embodiments, the subject is a human subject having chronic refractory gout.

In some embodiments, any one of the subjects for treatment as provided in any one of the methods provided has gout or a condition associated with gout or another condition as provided herein. In some embodiments, any one of the subjects for treatment as provided in any one of the methods provided has been diagnosed with a disease selected from the group consisting of gout, rheumatoid arthritis, osteoarthritis, cerebral stroke, ischemic heart disease, arrhythmia, and chronic renal disease. In some embodiments, any one of the subjects for treatment as provided in any one of the methods provided has chronic refractory gout. In some embodiments, any one of the subjects for treatment as provided in any one of the methods provided the subject has had or is expected to have gout flare. In some embodiments, any one of the subjects for treatment as provided in any one of the methods provided has one or more risk factors for hyperuricemia selected from the group consisting of insulin resistance, obesity, a purine rich diet and advanced age. In some embodiments, any one of the subjects for treatment as provided in any one of the methods provided has been diagnosed with symptomatic gout with at least 3 gout flares in the previous 18 months. In some embodiments, any one of the subjects for treatment as provided in any one of the methods provided has been diagnosed with at least 1 gout tophus or gouty arthritis. In some embodiments, any one of the subjects for treatment as provided in any one of the methods provided has a contraindication to allopurinol. Contraindications to allopurinol include extreme loss of body water, chronic heart failure, allergic reaction causing inflammation of blood vessels, liver problems and moderate to severe kidney impairment. In some embodiments, any one of the subjects for treatment as provided in any one of the methods provided has a failure to normalize uric acid to less than 6 mg/dL after at least 3 months of allopurinol treatment.

In some embodiments, the subject has or is at risk of having an elevated uric acid level, e.g., an elevated plasma or serum uric acid level. When blood levels of uric acid may exceed the physiologic limit of solubility, the uric acid may crystallize in the tissues, including the joints, and may cause gout and gout-associated conditions.

In some embodiments, serum uric acid levels >5 mg/dL, >6 mg/dL, or >7 mg/dl are indicative that a subject may be a candidate for treatment with any one of the methods or compositions or kits described herein.

In some embodiments, the subject has, or is at risk of having, hyperuricemia. In some embodiments, the subject has, or is at risk of having, gout, acute gout, acute intermittent gout, gouty arthritis, acute gouty arthritis, acute gouty arthropathy, acute polyarticular gout, recurrent gouty arthritis, chronic gout (with our without tophi), tophaceous gout, chronic tophaceous gout, chronic advanced gout (with our without tophi), chronic polyarticular gout (with our without tophi), chronic gouty arthropathy (with our without tophi), idiopathic gout, idiopathic chronic gout (with or without tophi), primary gout, chronic primary gout (with or without tophi), refractory gout, such as chronic refractory gout, axial gouty arthropathy, a gout attack, a gout flare, podagra (i.e., monarticular arthritis of the great toe), chiragra (i.e., monarticular arthritis of the hand), gonagra (i.e., monarticular arthritis of the knee), gouty bursitis, gouty spondylitis, gouty synovitis, gouty tenosynovitis, gout that affects tendons and ligaments, lead-induced gout (i.e., saturnine gout), drug induced gout, gout due to renal impairment, gout due to kidney disease, chronic gout due to renal impairment (with or without tophi), chronic gout due to kidney disease (with or without tophi), erosive bone disease associated with gout, stroke associated with gout, vascular plaque associated with gout, cirrhosis or steatohepatitis associated with gout, liver-associated gout, incident and recurrent gout, diabetes associated with damage to pancreas in gout, general inflammatory diseases exacerbated by gout, other secondary gout, or unspecified gout.

In some embodiments, the subject has, or is at risk of having, a condition associated with the renal system, for example, calculus of urinary tract due to gout, uric acid urolithiasis, uric acid nephrolithiasis, uric acid kidney stones, gouty nephropathy, acute gouty nephropathy, chronic gouty nephropathy, urate nephropathy, uric acid nephropathy, and gouty interstitial nephropathy.

In some embodiments, the subject has, or is at risk of having, a condition associated with the nervous system, for example, peripheral autonomic neuropathy due to gout, gouty neuropathy, gouty peripheral neuropathy, gouty entrapment neuropathy, or gouty neuritis.

In some embodiments, the subject has, or is at risk of having, a condition associated with the cardiovascular system, for example, metabolic syndrome, hypertension, obesity, diabetes, myocardial infarction, stroke, dyslipidemia, hypertriglyceridemia, insulin resistance/hyperglycemia, coronary artery disease/coronary heart disease, coronary artery disease or blockage associated with gout or hyperuricemia, heart failure, peripheral arterial disease, stroke/cerebrovascular disease, peripheral vascular disease, and cardiomyopathy due to gout.

In some embodiments, the subject has, or is at risk of having, a condition associated with the ocular system including, for example, gouty iritis, inflammatory disease in the eye caused by gout, dry eye syndrome, red eye, uveitis, intraocular hypertension, glaucoma, and cataracts.

In some embodiments, the subject has, or is at risk of having, a condition associated with the skin including, for example, gout of the external ear, gouty dermatitis, gouty eczema, gouty panniculitis, and miliarial gout.

In some embodiments, the subject is selected for treatment with an microbial cell engineered to degrade uric acid of the present disclosure. In some embodiments, the subject is selected for treatment of hyperuricemia with an engineered microbial cell of the present disclosure. In some embodiments, the subject is selected for treatment of gout with an engineered microbial cell of the present disclosure. In some embodiments, the subject is selected for treatment of chronic refractory gout with an engineered microbial cell of the present disclosure.

In certain embodiments, the methods of the present disclosure provide treatment of gout and diseases or disorders associated with hyperuricemia to human patients suffering therefrom. The treatment population is thus human subjects diagnosed as suffering from gout or hyperuricemia. The invention encompasses the treatment of a human subject at risk of suffering from a recurrent gout episode or for developing hyperuricemia or gout.

The present disclosure also encompasses treating a population of patients with drug-induced gout flares, including flares induced by gout therapeutics such as xanthine oxidase inhibitors, such as allopurinol and febuxostat; flares induced by urate oxidase, for example, uricase, rasburicase and pegylated uricase; and flares induced by uricosuric agents, such as probenecid, sulfinpyrazone, benzbromarone, and fenofibrate. By "drug-induced" gout flare is meant occurrence of or increased incidence of a gout flare associated with initiation of therapy to treat gout and/or administration of a therapeutic agent for the treatment of gout, for example, initiation of therapy with a xanthine oxidase inhibitor, urate oxidase, or a uricosuric agent. A gout flare is "associated" with initiation of gout therapy when the flare occurs contemporaneously or following at least a first administration of a therapeutic agent for the treatment of gout.

Pharmaceutical Compositions

The present disclosure encompasses the preparation and use of pharmaceutical compositions comprising an engineered microbial cell (e.g., engineered fungal cells) of the disclosure as an active ingredient. Such a pharmaceutical composition may consist of the active ingredient alone, as a combination of at least one active ingredient (e.g., an effective dose of an engineered fungal cell) in a form suitable for administration to a subject, or the pharmaceutical composition may comprise the active ingredient and one or more pharmaceutically acceptable carriers, one or more additional (active and/or inactive) ingredients, or some combination of these.

In some embodiments, a pharmaceutical composition comprises a plurality of the engineered fungal cells described herein, and a pharmaceutically acceptable carrier. In further embodiments, the pharmaceutical composition comprises a therapeutically effective dose of the engineered microbial cells.

In some embodiments, the pharmaceutical composition comprises between 10^6 and 10^12 engineered microbial cells.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The administration of the pharmaceutical compositions may be carried out in any convenient manner, including by aerosol inhalation, injection, ingestion, transfusion, implantation or transplantation. The compositions of the present disclosure may be administered to a patient orally.

As used herein, the term "pharmaceutically acceptable carrier" means a chemical composition with which the active ingredient may be combined and which, following the combination, can be used to administer the active ingredient to a subject.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the disclosure is contemplated include, but are not limited to, humans and other primates, mammals including commercially relevant mammals such as non-human primates, cattle, pigs, horses, sheep, cats, and dogs.

Pharmaceutical compositions that are useful in the methods of the disclosure may be prepared, packaged, or sold in formulations suitable for oral, or another route of administration.

A pharmaceutical composition of the disclosure may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the disclosure will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the disclosure may further comprise one or more additional pharmaceutically active agents.

Controlled- or sustained-release formulations of a pharmaceutical composition of the disclosure may be made using conventional technology.

The pharmaceutical compositions may be prepared, packaged, or sold in the form of a capsule or pill containing (freeze-) dried or metabolically active engineered microbes, a powder containing (freeze-) dried or metabolically active engineered microbes, or a suspension containing (freeze-) dried or metabolically active live microbes. These solids or liquids may be formulated according to the known art, and may comprise, in addition to the active ingredient, additional ingredients such as the dispersing agents, wetting agents, or suspending agents described herein. Such formulations may be prepared using a non-toxic orally-acceptable substance, such as cellulose, for example.

Other acceptable substances include, but are not limited to, guar gum, hypromellose (hydroxypropyl methylcellulose), inulin, fructooligosaccharides, gelatin, magnesium stearate, Silicon dioxide, rice bran extract, and lactose.

Formulation methods are described by e.g., Martins et al, Letters in Applied Microbiology 49:738-744 (2009), and by Joshi and Thorat, Drying Technology, 29:749-757 (2011).

The engineered microbial cell of the disclosure can be administered to an animal, e.g., a human. Where the engineered microbial cell are administered, they can be administered in an amount ranging from about 10^6 to about 10^12 cells wherein the cells are administered to the animal, preferably, a human patient in need thereof. While the precise dosage administered will vary depending upon any number of factors, including but not limited to, the type of animal and type of disease state being treated, the age of the animal and the route of administration.

The engineered microbial cell may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

An engineered microbial cell may be co-administered with the various other compounds (e.g. other therapeutic agents). Alternatively, the compound(s) may be administered in advance of or after administration of the engineered microbial cell. The frequency and administration regimen will be readily apparent to the skilled artisan and will depend upon any number of factors such as, but not limited to, the type and severity of the disease being treated, the age and health status of the animal, the identity of the compound or compounds being administered, the route of administration of the various compounds and the engineered microbial cell, and the like.

In some embodiments, the disclosure features a pharmaceutical composition comprising a plurality of the engineered microbial cells described herein, and a pharmaceutical carrier. In other embodiments, the disclosure features a pharmaceutical composition comprising a population of engineered microbial cells as described herein, and a pharmaceutical carrier. It will be understood that any single engineered microbial cell, plurality of engineered microbial cells, or population of engineered microbial cells as described elsewhere herein may be present in a pharmaceutical composition of the invention.

In some embodiments, the pharmaceutical compositions provided herein comprise engineered (i.e. modified) microbial cells and unmodified microbial cells. For example, a single unit dose of microbial cells (e.g., modified and unmodified microbial cells) can comprise, in various embodiments, about, at least, or no more than 10%, 20%, 30%, 40%, 50%, 60%, 70%, 75%, 80%), 85%, 90%, 95%, or 99% engineered microbial cells, wherein the remaining microbial cells in the composition are not engineered.

In some embodiments of the above aspects and embodiments, the engineered microbial cell is a fungal cell, e.g. *Saccharomyces boulardii.*

Combination Therapies

According to some embodiments, the disclosure provides methods that further comprise administering an additional agent (e.g. an additional therapeutic) to a subject. In some embodiments, the disclosure pertains to co-administration and/or co-formulation.

Additional therapeutics for elevated uric acid levels, gout, gout flares, or conditions associated with gout, may be administered to any one of the subjects provided herein, such as for the reduction of uric acid levels and/or gout treatment and/or gout flare prevention. Any one of the methods provided herein may include the administration of one or more of these additional therapeutics. In some embodiments, any one of the methods provided herein do not comprise the concomitant administration of an additional therapeutic. Examples of additional therapeutics include, but are not limited to, the following. Other examples will be known to those of skill in the art.

Additional therapeutics include anti-inflammatory therapeutics (i.e., any therapeutic that can act to reduce inflammation). Anti-inflammatory therapeutics include, but are not limited to, corticosteroids or derivatives of cortisol (hydrocortisone). Corticosteroids include, but are not limited to, glucocorticoids and mineralocorticoids. Still other examples of corticosteroids include, but are not limited to, those that are natural and those that are synthetic. Corticosteroids, particularly glycocorticoids, have anti-inflammatory and immunosuppressive effects that may be effective in managing symptoms, including pain and inflammation associated with gout, gout flare, and/or conditions associated with gout.

Administration of corticosteroids may also aid in reducing hypersensitivity reactions associated with one or more additional therapies, for example uricase replacement therapy.

Still other non-limiting examples of corticosteroids include prednisone, prednisolone, Medrol, and methylprednisolonc.

Additional therapeutics include short term therapies for gout flare or pain and inflammation associated with any of the symptoms associated with gout or a condition associated with gout include nonsteroidal anti-inflammatory drugs (NSAIDS), colchicine, and oral corticosteroids. Non-limiting examples of NSAIDS include both over-the-counter NSAIDS, such as ibuprofen, aspirin, and naproxen, as well as prescription NSAIDS, such as celecoxib, diclofenac, diflunisal, etodolac, indomethacin, ketoprofen, ketorolac, nabumetrone, oxaprozin, piroxiam salsalate, sulindac, and tolmetin.

Colchicine is an anti-inflammatory agent that is generally considered as an alternative for NSAIDs for managing the symptoms, including pain and inflammation associated with gout, gout flare, and/or conditions associated with gout.

Further examples of additional therapeutics include xanthine oxidase inhibitors, which are molecules that inhibit xanthine oxidase, reducing or preventing the oxidation of xanthine to uric acid, thereby reducing the production of uric acid. Xanthine oxidase inhibitors are generally classified as either purine analogues or other types of xanthine oxidase inhibitors. Examples of xanthine oxidase inhibitors include allopurinol, oxypurinol, tisopurine, febuxostat, topiroxostat, inositols (e.g., phytic acid and myo-inositol), flavonoids (e.g., kaempferol, myricetin, quercetin), caffeic acid, and 3,4-dihydrox-5-nitrobenzaldehyde (DHNB).

Still other examples of additional therapeutics include uricosuric agents. Uricosuric agents aim to increase excretion of uric acid in order to reduce serum levels of uric acid by modulating renal tubule reabsorption. For example, some uricosuric agents modulate activity of renal transporters of uric acid (e.g., URAT1/SLC22A12 inhibitors). Non-limiting examples of uricosuric agents include probenecid, benzbromarone, lesinurad, and sulfinpyrazone. Other additional therapeutics may also have uricosuric activity, such as aspirin.

Additional therapeutics also include other uricase-based therapies, which include pegylated uricase. Such therapies, such as when infused into humans, have been shown to reduce blood uric acid levels and improve gout symptoms. Rasburicase (ELITEK), an unpegylated engineered uricase cloned from *Aspergillus flavus*, is approved for management of uric acid levels in patients with tumor lysis syndrome. KRYSTEXXA (pegloticase) is a engineered uricase (primarily porcine with a carboxyl-terminus sequence from baboon) bound by multiple 10 kDa PEG molecules approved for the treatment of chronic refractory gout.

The treatments provided herein may allow patients to switch to oral gout therapy, such as with xanthine oxidase inhibitors, unless and until such patients experience a subsequent manifestation of uric acid deposits at which time a new course of treatment as provided herein according to any one of the methods provided is then undertaken. Any one of the methods provided herein, thus, can include the subsequent administration of an oral gout therapeutic as an additional therapeutic after the treatment regimen according to any one of the methods provided is performed. It is believed that oral therapy may not completely prevent the buildup over time of uric acid crystals in patients with a history of chronic tophaceous gout. As a result, it is anticipated that treatment as provided herein is likely to be required intermittently in such patients. Thus, in such subjects, the subject is also further administered one or more compositions according to any one of the methods provided herein.

The treatments provided herein may allow patients to subsequently be treated with a uric acid lowering therapeutic, such as a uricase.

Treatment according to any one of the methods provided herein may also include a pre-treatment with an anti-gout flare therapeutic, such as with colchicine or NSAIDS.

Accordingly, any one of the methods provided herein may further comprise such an anti-gout flare therapeutic whereby the anti-gout flare therapeutic is concomitantly administered with the composition comprising uricase and the composition comprising synthetic nanocarriers comprising an immunosuppressant.

Monitoring of a subject, such as the measurement of serum uric acid levels and/or ADAs, may be an additional step further comprised in any one of the methods provided herein. In some embodiments, should such subject develop an undesired immune response, the subject is further administered one or more compositions according to any one of the methods provided herein. In some embodiments of any one of the methods provided herein, the subject is monitored with dual energy computed tomography (DECT), that can be used to visualize uric acid deposits in joints and tissues. Imaging, such as with DECT, can be used to assess the efficacy of treatment with any one of the methods or compositions provided herein. As a result, any one of the methods provided herein can further include a step of imaging, such as with DECT. In some embodiments of any one of the methods provided herein, the subject is one in which the gout, such as chronic tophaceous gout, or condition associated with gout has been diagnosed with such imaging, such as with DECT.

Identifying Uric Acid Degradation

A method to identify uric acid degrading polypeptides can comprise the steps of functionally expressing a candidate uric acid degrading polypeptide by operably linking it to a promoter in a cell functionally expressing one or more of the uric acid transporters of SEQ ID NO: 9-18, or polypeptide having uric acid transporter activity; identifying cells with increased urate consumption by quantifying urate uptake and biodegradation of cells from step 1. using a urate consumption assay and comparing their urate consumption to cells functionally expressing only the one or more of the uric acid transporters of SEQ ID NO: 9-18 or polypeptide having uric acid transporter activity. The cells that show increased urate consumption functionally express a uric acid degrading polypeptide, thereby confirming the candidate uric acid degrading polypeptide can functionally break down uric acid and encodes a uricase (EC 1.7.3.3).

A method to identify uric acid transporters can comprise the steps of functionally expressing a candidate uric acid transporting polypeptide by operably linking it to a promoter in a cell functionally expressing one or more of the uricases of SEQ ID NO: 1-8, or polypeptide having uricase activity; identifying cells with increased urate consumption by quantifying urate uptake and biodegradation of cells from step 1. using a urate consumption assay and comparing their urate consumption to cells functionally expressing only the one or more of the uricases of SEQ ID NO:1-8 or polypeptide having uricase activity. The cells that show increased urate consumption functionally express a uric acid transporter polypeptide, thereby confirming the candidate uric acid transporting polypeptide can functionally transport uric acid from outside the cell to inside the cell and encodes a uric acid transporter.

An assay to quantify urate uptake and biodegradation by cells can comprise collecting cells followed by resuspension in assay buffer containing dissolved uric acid with A293 between 0.0 and 3.0; incubating resuspended cells under conditions suitable for uric acid uptake and biodegradation; removing aliquots at designated intervals; collecting the supernatant; and spectrophotometrically determining the reduction in urate concentration by measuring absorbance at a wavelength where urate strongly absorbs, preferably between 275 nm and 350 nm, most preferably 293 nm.

Example 1

Example 1: "*Saccharomyces boulardii* cells genetically engineered to comprise *Candida utilis* uricase and *Aspergillus nidulans* UapA uric acid transporter"

Episomal expression vector encoding *Candida utilis* uricase and *Aspergillus nidulans* UapA uric acid transporter:

An episomal plasmid shuttle vector was constructed encoding genes for the expression of *Candida utilis* uricase (SEQ ID NO: 1) (CuUOX) and *Aspergillus nidulans* UapA uric acid transporter (SEQ ID NO: 9) (AnUapA). A schematic drawing of the map is provided in FIG. 1. The sequence of this episomal plasmid shuttle vector is included in SEQ ID NO: 19

This vector is able to replicate in *E. coli* cells grown in the presence of Ampicillin by virtue of the Ampicillin resistance gene (β-Lactamase) and the bacterial F1 origin of replication. The vector is able to replicate in *S. boulardii* cells grown in the presence of G418 disulphate by virtue of the bacterial aminoglycoside phosphotransferase (from transposon Tn903) and the *S. cerevisiae* 2 micron plasmid origin of replication.

The vector encodes *Candida utilis* uricase under control of the *S. boulardii* GPD (aka TDH3) promoter, and *Aspergillus nidulans* UapA uric acid transporter under control of the *S. boulardii* Pgk1 promoter.

Salient features of SEQ ID: 19 include: GPD (TDH3) promoter in the 13-663 nucleotides; *Candida* Uricase in the 687-1598 nucleotides; VPS13 terminator in the 1599-1701 nucleotides; TPI1 promoter in the 1714-2163 nucleotides; EM7 promoter in the 2164-2231 nucleotides; KanR in the 2232-3041 nucleotides; *Ashbya gossypii* TEF terminator in the 3047-3244 nucleotides; Pgk1 promoter in the 9925-9388 (antisense) nucleotides; UapA UA transporter in the 9387-7663 (antisense) nucleotides; Prm9 terminator in the 7662-7413 (antisense) nucleotides; yeast 2μ plasmid origin of replication in the 6033-7378 nucleotides; AmpR in the 5403-4543 (antisense) nucleotides; F1 Origin of replication in the 4372-3784 (antisense) nucleotides.

The vector was amplified in *E. coli* DH5a cells (Cat no. 18265017, Thermo Fisher Scientific, Grand Island, NY 14072, USA), and extracted using methods well known in the art, as described e.g. in Sambrook and Russell, Molecular cloning: a laboratory manual. Ed. 3. Cold spring harbor laboratory press, 2001. The vector DNA was further purified using silica spin columns.

*Saccharomyces boulardii* cells (Kirkman, Lake Oswego, OR 97035) were grown in YPD medium by transferring the content of a capsule into 50 mL YPD medium in a 125 mL shake flask. The *S. boulardii* starter culture was grown on a platform shaker at 225 rpm and 30° C. to stationary phase (OD 600 to or about 3) overnight. The next morning, a 5 mL aliquot of the overnight culture was inoculated into 100 mL YPD media in a 250 mL shake flask to initiate a culture at approx. OD600 0.3. The inoculated cells were grown in a shaking incubator at 30° C. and 225 rpm until OD600 was approximately 1.6. Yeast cells were pelleted by centrifugation at 3000 rpm for 5 minutes and the media was aspirated. Cell were resuspended in 20 mL ice cold water, and pelleted again by centrifugation at 3000 rpm for 5 min. The supernatant was aspirated, and cells were resuspended in 20 mL ice cold water, and pelleted again by centrifugation at 3000 rpm for 5 min. The supernatant was aspirated, and cells were resuspended in 50 mL ice-cold electroporation buffer (1 M Sorbitol/1 mM CaCl2 in distilled water), and pelleted again by centrifugation at 3000 rpm for 5 min.

Cells were resuspended in 20 mL 0.1 M LiOAc/10 mM DTT, transferred to a 125 mL shake flask and shaked at 100 rpm for 30 minutes at 30° C. Cells were pelleted by centrifugation at 3000 rpm for 3 min, the supernatant removed, and cells were gently resuspended in 20 mL ice-cold electroporation buffer. Cells were pelleted by centrifugation at 3000 rpm for 3 min and the supernatant removed. Cells were resuspended in electroporation buffer to reach a final volume of 1 mL. 40 μL DNA solution was transferred into a pre-chilled electroporation cuvette (2 mm electrode gap) on ice, and 400 μL resuspended electrocompetent yeast cells was added. The cuvette was kept on ice for 5 minutes until electroporation. The cells were electroporated at 2.5 kV, 25 μF and 200 Ohm. Electroporated cells were transferred from each cuvette into 10 mL of 1:1 mix of 1 M Electroporation buffer: YPD medium. The cells were recovered by incubation on a platform shaker at 225 rpm and 30° C. for 2 hours. The cells were pelleted by centrifugation, the supernatant removed, and the cells resuspended in 1 mL YPD medium. Cells were pelleted again, the supernatant removed, and cells were resuspended in 200 μL YPD medium. Cells were plate on YPD plates with 600 μg/mL G418 disulphate, taped shut with parafilm, and incubate at 30° C. for 2 days. Colonies were picked used to inoculate liquid YPD cultures with 200 600 μg/mL G418 sulphate, and cells were grown for 48 hours to approximately stationary phase.

A control culture consisting of parental, untransformed *S. boulardii* was grown in YPD medium without antibiotics, and these cells were also grown for 48 hours to approximately stationary phase. 1 mL of cell suspension was removed from the culture, transformed cells were pelleted in a 1.7 mL Eppendorf tube by centrifugation. The supernatant was removed, and cells were resuspended in 1 mL of phosphate buffered saline, pH 7.4, to wash the cells. Cells were then resuspended in 1 mL phosphate buffered saline containing uric acid at a concentration yielding an optical density at 293 nm (OD293) of approximately A293=1.0. A control consisted of uric acid solution in PBS without any cells. The suspensions were then incubated on a tumbler at 37° C. for 10 minutes.

Following incubation, cells were pelleted again, 500 μL of supernatant was assayed spectrophotometrically using a quartz glass cuvette with 1 cm pathlength in a Nanodrop spectrophotometer (see Prætorius and Poulsen, Scandinavian Journal of Clinical and Laboratory Investigation, 5:273-280 (1953)). The cell pellet was resuspended in the remaining supernatant, and cells were incubated for an additional 30 minutes on a tumbler at 37° C. Following the second incubation, cells were pelleted again, and the remaining 500 μL of supernatant was assayed spectrophotometrically using a quartz glass cuvette with 1 cm pathlength in a Nanodrop spectrophotometer. It should be noted uric acid has an absorbance peak at 293 nm, where the degradation product as produced by uricase does not absorb at this wavelength.

Results are shown in FIG. 2 (absorbance spectra 200-350 nm) and FIG. 3 (absorbance at 293 nm). Results showed that uric acid in the suspension containing *S. boulardii* engineered with the shuttle vector (SEQ ID: 19) was partially degraded after 10 minutes, and essentially completely degraded after 40 minutes. In contrast, uric acid in the suspension containing wild-type *S. boulardii* was not degraded, as was uric acid in the solution without *S. boulardii*. In both of the latter, uric acid levels were the same as before treatment.

Example 2

Example 2. "*Escherichia coli* strain Nissle cells genetically engineered to overexpress *Escherichia coli* YgfU uric acid transporter and *Arthrobacter globiformis* uricase induced by low oxygen conditions"

A synthetic plasmid encoding an expression cassette comprising the *Arthrobacter globiformis* uricase operably linked to a promoter induced by the oxygen level-dependent FNR protein from *N. gonorrhoeae* (see, e.g., Isabella et al, BMC Genomics 12:1471-2164 (2011)) (a promoter that is induced by low-oxygen or anaerobic conditions); and, with translation terminated by the synthetic BBa_B1002 terminator, and with said operon flanked by 50 bps sequences facilitating homologous recombination into the malE/K locus, e.g. as set forth in SEQ ID NO: 20, is obtained from a synthetic DNA vendor, e.g. Twist Bioscience (San Francisco, CA) or Integrated DNA Technologies (Coralville, IA). The fragment may additionally comprise antibiotic selection markers or other selectable markers.

This fragment is flanked by appropriate unique NotI restriction sites. This fragment is excised from a large scale preparation of the plasmid, purified, and used to transform *E. coli* Nissle cells.

A synthetic plasmid encoding an expression cassette comprising the *Escherichia coli* YgfU uric acid transporter operably linked to a promoter induced by the oxygen level-dependent FNR protein from *N. gonorrhoeae* (see, e.g., Isabella et al, BMC Genomics 12:1471-2164 (2011)) (a promoter that is induced by low-oxygen or anaerobic conditions); and, with translation terminated by the synthetic Bba_B1006 terminator, and with said operon flanked by 50 bps sequences facilitating homologous recombination into the lacZ locus, eg as set forth in SEQ ID NO: 21, is obtained from a synthetic DNA vendor, e.g. Twist Bioscience (San Francisco, CA) or Integrated DNA Technologies (Coralville, IA). The fragment may additionally comprise antibiotic selection markers or other selectable markers.

This fragment is flanked by appropriate unique NotI restriction sites. This fragment is excised from a large-scale preparation of the plasmid, purified, and used to transform *E. coli* Nissle cells.

Lambda red recombination is used to make chromosomal modifications, e.g., to express *Escherichia coli* YgfU uric acid transporter and *Arthrobacter globiformis* uricase in *E. coli* Nissle. Lambda red recombinase mediated recombineering is a procedure using recombination enzymes from a bacteriophage lambda to insert a piece of custom (e.g., synthetic) DNA into the chromosome of *E. coli.* pKD46 (CGSC #7669, Yale *Coli* Genetic Stock Center, Dept. of Molecular, Cellular, and Developmental Biology, Yale University, New Haven, CT 06520, USA) is a temperature-sensitive plasmid that encodes the lambda red recombinase genes. The pKD46 plasmid is transformed into the *E. coli* Nissle host strain (PZN: 03840841, Mutaflor®, ArdeyPharm, Herdecke, Nordrhein-westfalen, Germany). *E. coli* Nissle cells are grown overnight in LB media. The overnight culture is diluted 1:100 in 5 mL of LB media and grown until it reaches an OD600 of 0.4-0.6. All tubes, solutions, and cuvettes are pre-chilled to 4° C. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 1 ng of pKD46 plasmid DNA is added to the *E. coli* cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 30° C. for 1 hr. The cells are spread out on a selective media plate containing antibiotics and incubated overnight at 30° C.

DNA sequences comprising the desired urate catabolism genes and transporters, e.g., those shown above are ordered from a gene synthesis company. The lambda enzymes are used to insert this construct into the genome of *E. coli* Nissle through homologous recombination. The construct is inserted into a specific site in the genome of *E. coli* Nissle based on its DNA sequence. In one example, the construct encodes *Escherichia coli* YgfU uric acid transporter, which is inserted at the lacZ site in the *E. coli* Nissle genome. In another example, the construct encodes *Arthrobacter globiformis* uricase, which is inserted at the MalE/Ksite in the *E. coli* Nissle genome.

The homologous sequences are ordered as part of the synthesized gene. Alternatively, the homologous sequences may be added by PCR. The construct is used to replace the natural sequence in the *E. coli* Nissle genome. The construct may include an antibiotic resistance marker that may be removed by recombination.

The constructs comprising the desired urate catabolism genes and transporters are transformed into *E. coli* Nissle comprising pKD46. All tubes, solutions, and cuvettes are pre-chilled to 4° C. An overnight culture is diluted 1:100 in 5 mL of LB media containing ampicillin and grown until it reaches an OD600 of 0.1. 0.05 mL of 100× L-arabinose stock solution is added to induce pKD46 lambda red expression. The culture is grown until it reaches an OD600 of 0.4-0.6. The *E. coli* cells are centrifuged at 2,000 rpm for 5 min. at 4° C., the supernatant is removed, and the cells are resuspended in 1 mL of 4° C. water. The *E. coli* are centrifuged at 2,000 rpm for 5 min. at 4° C., the supernatant is removed, and the cells are resuspended in 0.5 mL of 4° C. water. The *E. coli* are centrifuged at 2,000 rpm for 5 min. at 4° C., the supernatant is removed, and the cells are resuspended in 0.1 mL of 4° C. water. The electroporator is set to 2.5 kV. 0.5 μg of the constructs comprising the desired urate catabolism genes and transporters is added to the cells, mixed by pipetting, and pipetted into a sterile, chilled cuvette. The dry cuvette is placed into the sample chamber, and the electric pulse is applied. 1 mL of room-temperature SOC media is immediately added, and the mixture is transferred to a culture tube and incubated at 37° C. for 1 hr. The cells are spread out on an LB plate and incubated overnight.

The presence of the mutation is verified by colony PCR. Colonies are picked with a pipette tip and resuspended in 20 μl of cold ddH2O by pipetting up and down. 3 μL of the suspension is pipetted onto an index plate with appropriate antibiotic for use later. The index plate is grown at 37° C. overnight. A PCR master mix is made using 5 μL of 10×PCR buffer, 0.6 μL of 10 mM dNTPs, 0.4 μL of 50 mM Mg2SO4, 6.0 μL of 10× enhancer, and 3.0 μL of ddH2O (15 μL of master mix per PCR reaction). A 10 UM primer mix is made by mixing 2 μL of primers unique to the argA mutant construct (100 μM stock) into 16 μL of ddH2O. For each 20 μL reaction, 15 μL of the PCR master mix, 2.0 μL of the colony suspension (template), 2.0 μL of the primer mix, and 1.0 μL of Pfx Platinum DNA Pol are mixed in a PCR tube. The PCR thermocycler is programmed as follows, with steps 2-4 repeating 34 times: 1) 94° C. at 5:00 min., 2) 94° C. at 0:15 min., 3) 55° C. at 0:30 min., 4) 68° C. at 2:00 min., 5) 68° C. at 7:00 min., and then cooled to 4° C. The PCR products are analyzed by gel electrophoresis using 10 μL of each amplicon and 2.5 μL 5×dye. The PCR product only forms if the mutation has inserted into the genome.

Next, the antibiotic resistance is removed by transforming cells with pCP20 plasmid (CGSC #14177, Yale *Coli* Genetic Stock Center, Dept. of Molecular, Cellular, and Developmental Biology, Yale University, New Haven, CT 06520, USA)

pCP20 has the yeast Flp recombinase gene, FLP, chloramphenicol and ampicillin resistant genes, and temperature sensitive replication. Bacteria are grown in LB media containing the selection antibiotic at 37° C. until OD600 reaches 0.4-0.6. 1 mL of cells are pelleted at 16,000×g for 1 min, the supernatant is discarded and the pellet is resuspended in 1 mL ice-cold 10% glycerol. This wash step is repeated 3 times. The pellet is then resuspended in 70 μl ice-cold 10% glycerol. Next, cells are electroporated with 1 μg pCP20 plasmid DNA, and 1 mL SOC supplemented with 3 mM thymidine is immediately added to the cuvette. Cells are resuspended and transferred to a culture tube and are grown at 30° C. for 1 hour. Cells are then pelleted at 10,000×g for 1 minute, the supernatant is discarded, and the cell pellet is resuspended in 100 μL LB containing 3 mM thymidine and spread on LB agar plates containing 3 mM thy and 100 μg/mL carbenicillin. Cells are grown at 30° C. for 16-24 hours. Next, transformants are colony purified non-selectively (in the absence of antibiotics) at 42° C.

To test the colony-purified transformants, a colony is picked from the 42° C. plate with a pipette tip and resuspended in 10 μL LB. 3 μL of the cell suspension is pipetted onto a set of 3 plates: Cam, (37° C.: tests for the presence/absence of CamR gene in the genome of the host strain), Amp, (30° C.: tests for the presence/absence of AmpR from the pCP20 plasmid) and LB only (37° C., desired cells that have lost the chloramphenicol cassette and the pCP20 plasmid). Colonies were considered cured if there is no growth in neither the Cam or Amp plate, picked, and re-streaked on an LB plate to get single colonies, and grown overnight at 37° C.

Example 3

Example 3: "*Bacteroides* Cells Genetically Engineered to Comprise *Spirosoma* Uricase and Uric Acid Transporter"

Adding urate-degradation capabilities to a member of the genus *Bacteroides* can be accomplished by addition of transgenes from other organisms (e.g. species from the Bacteroidetes phylum, e.g. a species from the *Spirosoma* genus).

A synthetic conjugative plasmid containing an expression cassette comprising a synthetic operon encoding a *Spirosoma* uricase (SEQ ID NO: 8) and *Spirosoma* urate transporter SEQ ID NO: 18), operably linked to a phage derived promoter, e.g. P_BfP1E6 (as described in Russ et al, WO2020123483), e.g. as set forth in SEQ ID NO: 22, is obtained from a synthetic DNA vendor, e.g. Twist Bioscience (San Francisco, CA) or Integrated DNA Technologies (Coralville, IA). The plasmid may carry an NBU2 integrase gene, which catalyzes genomic integration of the plasmid at the 3' end of a serine-tRNA gene in the *Bacteroides* genome. The plasmid may additionally comprise antibiotic selection markers or other selectable markers. Multiple selective markers (such as tetracycline, erythromycin, or chloramphenicol) can be used to deliver multiple constructs into a single *Bacteroides* strain. The plasmid has the RK2/RP4 transfer origin.

The plasmid is transformed into *Escherichia coli* S17-1 donor cells (Catalog number 47055, ATCC). The RK2 conjugative machinery allows for conjugative transfer of plasmids bearing an RP4 transfer origin to a variety of species, including *Bacteroides*. DNA is transformed with addition of 20 μL of chemically competent *E. coli* S17-1 cells (mid-log cells resuspended 1:20 in TSS/KCM: LB medium with 8.3% PEG-3350, 4.2% DMSO, 58 mM MgCI2, 167 mM CaCI2 and 457 mM KCI), followed by a 90 second heat shock at 42° C., recovery at 37° C. for 30 minutes, a dilution into 600 μL LB medium with Ampicillin in a deep well 96-well plate (Corning 07-200-700) and aerobic growth at 37° C. A *Bacteroides* culture is prepared with overnight anaerobic growth in trypticase yeast extract-glucose (TYG) growth medium. At mid to late log growth, 200 μL of the transformed S17-1 cells are spun down, resuspended with 10 μL of a 1:10 concentration of the *Bacteroides* culture, and added to a deep well 96-well plate containing 400 μL of solidified Brain Heart Infusion Blood Agar (BHI-BA) per well. After at least 16 hours, the lawn of S17-1 and *Bacteroides* are resuspended in 400 μL of TYG by vortex or pipetting, 200 μL of the resuspension are spun down and resuspended in 15 μL TYG and several dilutions in TYG are made. 3 μL of the resuspension and its dilutions are spotted onto a 120×120 mm square petri dish containing BHI-BA plus the appropriate antibiotics (200 μg/mL gentamycin, and 25 μg/mL erythromycin or 2 μg/mL tetracycline). *Bacteroides* colonies can be picked after a 24 hour anaerobic incubation at 37° C.

Example 4. "*Bacillus* Cells Genetically Engineered to Overexpress Uricase and/or Uric Acid Transporter"

Various bacterial species in the genus *Bacillus*, e.g. *B. subtilis*, appear to endogenously comprise genes involved in uric acid catabolism genes, including uricase and/or one or (putative) more uric acid transporter(s). The ability of *Bacillus* cells to take up and break down uric acid may be improved by overexpression of uricase, e.g. PucL, and/or uric acid (purine) transporters, e.g. PucJ and/or PucK (see e.g. Schultz et al, Journal of Bacteriology 183:3293-3302 (2001)). The flgM gene may be removed to yield a *Bacillus* strain with enhanced gene expression from the hag promoter (as described in Abbott, US 2020/0345793 A1). Deletion of flgM greatly enhances constitutive expression and activity of SigD, and consequently results in higher and more constitutive transcription of the flagellar operon and specifically the hag gene.

The *B. subtilis* strain PY79 from the *Bacillus* Genetic Stock Center is used (strain 1A747) for all manipulations. The CsrA-binding site in the *Bacillus* hag promoter may be mutated to constitutively enhance promoter activity (as described in Abbott, US 2020/0345793 A1). Bacteria are grown in LB medium (1% tryptone, 0.5% yeast extract, 0.5% sodium chloride, with addition of 1.5% agar for solid media. For MLS resistance selection, 1 μg/mL erythromycin and 25 μg/mL lincomycin are used. For transformation experiments, bacteria are grown in modified competence (MC) medium (100 mM phosphate buffer, 2% glucose, 3 mM trisodium citrate, 22 mg/L ferric ammonium citrate, 0.1% casein hydrolysate, 0.16% glutamic acid, 3 mM magnesium sulfate). The plasmid used to make genetic modifications may be pMiniMAD (Catalog #ECE765, *Bacillus* Genetic Stock Center, Biological Sciences 556, 484 W. 12th Ave, Columbus, OH 43210-1214) as described in Patrick and Kearns, Mol. Microbiol. 70:1166-1179 (2008). The hag (flagellin) gene is replaced with an operon encoding uric acids transporter(s) and urate catabolism genes.

A synthetic plasmid encoding an expression cassette comprising a partial Puc operon comprising the *Bacillus* PucJ and PucL purine transporters (SEQ ID. NO: 14 and SEQ ID. NO: 15), the *Bacillus* PucL uricase/OHCU decarboxylase fusion protein (SEQ ID. NO: 6), and a *Bacillus* HIUHase operably linked to a *Bacillus* hag promoter, flanked by 800 base pairs 5' and 3' of the hag gene (as described in Abbott, US 2020/0345793 A1), e.g. as set forth in SEQ ID NO: 23, is obtained from a synthetic DNA vendor, e.g. Twist Bioscience (San Francisco, CA) or Integrated DNA Technologies (Coralville, IA).

This fragment is excised using the BamHI restriction enzyme, subcloned into the pMiniMAD plasmid linearized with BamHI and dephosphorylated with Calf intestinal phosphatase as recommended by the manufacturer (New England Biolabs). Plasmid DNA is used as the DNA source for chromosomal modifications. A single colony of *Bacillus* strain PY79 is picked, and inoculated in 2 mL of MC medium in a 15 mL test tube. The culture is grown at 37° C. with shaking at 275 rmp for 4.5 hours, or approx. 1 hour after the end of the exponential growth phase. 400 μL of the culture is transferred to a new 15 mL test tube, and 1 μg of pMiniMAD plasmid containing the fragment from SEQ ID NO: 23 is added. The culture with DNA is returned to the 37° C. shaker for 1.5 hours. Cultures are plated on LB agar with 1 μg/mL erythromycin and 25 μg/mL lincomycin, and incubated overnight at 37° C. Isolated colonies are screened for mutant allele via PCR using primer pairs where one primer anneals to a region outside the insert, and the other anneals to a region inside the insert. If the insert has recombined into the chromosome at the expected locus, PCR products of the expected size are obtained. A positive colony is then inoculated in 3 mL LB broth without antibiotics. This culture is grown overnight at room temperature with shaking at 275 rpm. 10 uL of the overnight culture is streaked on LB without antibiotics and grown at 37° C. overnight. Because of the lack of antibiotic selection, the plasmid is lost during overnight replication. The observed stability of this plasmid is about 90%, with about 1 colony in 10 losing the plasmid at this stage. Isolated colonies are duplicate streaked on LB plates with and without selection antibiotics (1 μg/mL erythromycin and 25 μg/mL lincomycin), and grown overnight at 37° C. Antibiotic sensitive colonies are screened again with the same primer pairs to identify strains with the mutant allele.

Example 5. "*Kluyveromyces* Cells Genetically Engineered to Comprise *Candida utilis* Uricase and *Aspergillus nidulans* UapA Uric Acid Transporter"

*Kluyveromyces* cells such as *K. lactis* or *K. marxianus* may be engineered to express uricase and/or uric acid transporter polypeptides using protocols and methods described in eg. Rajkumar et al, Front. Bioeng. Biotechnol. 7:97, doi: 10.3389/fbioe.2019.0009 (2019).

A synthetic integrative plasmid encoding two expression cassettes, one comprising a *Kluyveromyces* PGK1 promoter driving expression of the *Aspergillus nidulans* AnUapA uric acid transporter, with transcription terminated by the *Kluyveromyces* INUI terminator, and the other comprising a *Kluyveromyces* PDC1 promoter driving expression of the *Candida albicans* uricase, with transcription terminated by the *Kluyveromyces* PGK1 terminator, flanked by 878 base pairs 5' and 3' of the LAC4 β-galactosidase gene (as described in Rajkumar et al, Front. Bioeng. Biotechnol. 7:97, doi: 10.3389/fbioe.2019.0009 (2019)), and a kanMX antibiotic resistance marker, e.g. as set forth in SEQ ID NO: 24, is obtained from a synthetic DNA vendor, e.g. Twist Bioscience (San Francisco, CA) or Integrated DNA Technologies (Coralville, IA).

*Kluyveromyces* may be transformed using the LiOAc/PEG method as outlined by Gietz, Yeast Protocols 33-44. Humana Press, New York, NY, 2014.

*Kluyveromyces* cells are grown in 3 mL YPD at 250 rpm and 30° C. overnight. The following day, cultures are diluted in 50 mL YPD and allowed to grow until they reach an OD600 of approx. 0.8. Cells from 50 mL YPD cultures are collected by centrifugation (2700 rcf, 2 min, 25° C.). The cells are washed with 50 mL sterile water and collected by centrifugation at 2700 rcf for 2 min at RT. The cells are washed again with 25 mL sterile water and collected by centrifugation at 2700 rcf for 2 min at RT. The cells are resuspended in 1 mL 100 mM lithium acetate and transferred to a 1.5 mL Eppendorf tube. The cells are collected by centrifugation for 10 sec at 18,000 rcf at RT. The cells are resuspended in a volume of 100 mM lithium acetate that is approximately 4× the volume of the cell pellet.

The expression cassette is excised from the integrative plasmid using AscI (New England Biolabs). A volume of 10-15 μL of DNA, 72 μL 50% PEG 3350, 10 μL 1 M lithium acetate, 3 μL denatured salmon sperm DNA, and sterile water is combined to a final volume of 100 μL for each transformation. In a 1.5 mL tube, 15 μL of the cell suspension is added to the DNA mixture and the transformation suspension is vortexed with 5 short pulses. The transformation is incubated for 30 min at 30° C., followed by incubation for 22 min at 42° C. The cells are collected by centrifugation for 10 sec at 18,000 rcf at RT. The cells are resuspended in 400 μL of an appropriate medium and spread on YPGal (2% galactose, 2% peptone, 1% yeast extract) plates containing 200 μg/mL G418 and 40 μg/mL X-Gal. Correctly integration of the expression cassette into the LAC4 locus results in the inability of cells to metabolize X-Gal, yielding white instead of blue colonies.

After 48 h growth on selective medium, white transformant colonies are inoculated into 2 mL YPD with G418 and grown overnight at 30° C. with 200 rpm agitation. The following day, the cultures are diluted 100-fold into 2 mL SD medium with 150 μg/mL G418 (approximately corresponding to a starting optical density of 0.1) and grown at 30° C. for 24 h with 200 rpm shaking.

Example 6. "Identification of a Functional *Zygosaccharomyces parabailii* Uricase"

A putative *Zygosaccharomyces parabailii* uricase was identified by a BLASTP search of *Zygosaccharomyces* (taxid: 4953) proteins through the public online interface available on the world wide web at blast.ncbi.nlm.nih.gov/Blast.cgi with the default settings with the *Aspergillus flavus* uricase (SEQ ID NO: 2) as the query. One of the search results, accession number AQZ10287.1 was 45.60% identical with an E-value of 5e-85. A search against the conserved domain database through the public online interface available on the world wide web at ncbi.nlm.nih.gov/Structure/cdd/wrpsb.cgi with the default settings showed this *Zygosaccharomyces parabailii* protein putatively encoded a uricase with extensive similarity to TIGR03383 (E-value of 2.60e-128)

A synthetic DNA encoding the putative *Zygosaccharomyces parabailii* uricase accession number AQZ10287.1 with codon usage optimized towards *Saccharomyces cerevisiae* through the online codon optimizer available on the world wide web at idtdna.com/CodonOpt with flanking BstBI and NdeI restriction sites (as exemplified in SEQ ID NO:25) was obtained from Integrated DNA Technologies (Coralville, IA). The BstBI/NdeI fragment was excised and subcloned into the BstBI/NdeI sites of the shuttle vector of Example 1 (SEQ ID NO: 19), resulting in the functional replacement of the *Candida utilis* uricase ORF with the putative *Zygosaccharomyces parabailii* uricase ORF.

The shuttle vector encoding the *Zygosaccharomyces parabailii* uricase ORF was transformed into *S. boulardii* cells as exemplified in Example 1. Cells were selected on YPD plates containing 600 μg/mL G418, a colony was inoculated into YPD medium containing 200 μg/mL G418, and a control culture consisting of *S. boulardii* cells transformed with the vector of Example 1 (SEQ ID NO: 18) was grown in YPD medium without antibiotics.

Example 7. "Identification of a Functional *Zygosaccharomyces parabailii* Uric Acid Transporter"

A putative *Zygosaccharomyces parabailii* uric acid transporter was identified by a BLASTP search of *Zygosaccharomyces* (taxid: 4953) proteins through the public online interface available on the world wide web at blast.ncbi.nlm.nih.gov/Blast.cgi with the default settings with the *Aspergillus* nidulas UapA (SEQ ID NO: 9) as the query. One of the search results, accession number AQZ18664.1 was 56.28% identical with an E-value of 0. A search against the conserved domain database through the public online interface available on the world wide web at ncbi.nlm.nih.gov/Structure/cdd/wrpsb.cgi with the default settings showed this *Zygosaccharomyces parabailii* protein putatively encoded a uracil-xanthine permease with extensive similarity to TIGR00801 (E-value of 6.94c-115).

A synthetic DNA encoding the putative *Zygosaccharomyces parabailii* uricase accession number AQZ18664.1 with codon usage optimized towards *Saccharomyces cerevisiae* through the online codon optimizer available on the world wide web atidtdna.com/CodonOpt with flanking KpnI and NheI restriction sites (as exemplified in SEQ ID NO: 26) was obtained from Integrated DNA Technologies (Coralville, IA). The KpnI/NheI fragment was excised and subcloned into the KpnI/NheI sites of the shuttle vector of Example 1 (SEQ ID NO: 19), resulting in the functional replacement of the *Aspergillus* nidulas UapA uric acid transporter ORF with the putative *Zygosaccharomyces parabailii* uric acid transporter ORF.

The shuttle vector encoding the *Zygosaccharomyces parabailii* uric acid transporter ORF was transformed into *S. boulardii* cells as exemplified in Example 1. Cells were selected on YPD plates containing 600 μg/mL G418, a colony was inoculated into YPD medium containing 200 μg/mL G418, and a control culture consisting of *S. boulardii* cells transformed with the vector of Example 1 (SEQ ID NO: 18) was grown in YPD medium without antibiotics.

Example 8. "Urate Consumption Assay"

A urate consumption assay was developed. The assay was performed using an pH 7.0 phosphate buffer (yellow pH 7.0 standard) as the assay buffer (Biopharm UPC 721272377576). The assay solution consisted of assay buffer with 10 mM glucose and uric acid at A293 1.5-2.0. A uric acid stock solution was prepared by dissolving a small amount of uric acid (3 mm at tip of small metal spatula) in 20 mL assay buffer in a 50 mL conical tube, and briefly heated up in microwave. Undissolved uric acid was pelleted by centrifuging 5 minutes at 3000×g. The supernatant was then used for assays. A BioRad SmartSpec™ Plus spectrophotometer was used with a 1 cm quartz glass microcuvetter. The spectrophotometer was blanked using buffer only at 293 nm. A dilution was prepared with an A293 of 1.5-2.0.

Glucose was added to the assay buffer to a final concentration of 10 mM using the 2 M (200×) stock solution prepared in assay buffer.

Mid-log phase exponentially growing cells were harvested and OD600 (absorbance at 600 nm) of the culture was measured using a BioRad SmartSpec™ Plus spectrophotometer and the spectrophotometer was blanked using water. Cultures were diluted 1:10 in water, and OD600 was measured in the spectrophotometer. The volume of cell culture that is needed was calculated to obtain a final assay solution cell concentration of OD600=2. For 4 mL of assay solution at OD600=2, an equivalent of 8 OD600 was transferred to a 1.7 mL Eppendorf tube. Cells were pelleted by centrifugation at 20000×G for 2 minutes. The supernatant was aspirated with a p1000 micro pipette, cells were washed by resuspension in 500 μL H2O, pelleted again, and the supernatant was carefully aspirated with a p1000 micro pipette. The cell pellet was resuspended in 4 mL assay solution in a round bottom capped falcon tube (BD Falcon #352006). Falcon tubes were then transferred to a shaker incubator set at 37° C. and 350 RPM. 500 μL cell suspension aliquots were sampled at intervals, and transferred to a 1.7 mL Eppendorf tube. Cells were pelleted by centrifugation at 20000×G for 2 minutes. 400 μL of the clarified supernatant was transferred to a 1 cm path length quartz glass cuvette, and A293 was measured. At the end of the assay, OD600 of the cell suspension was measured to confirm suspensions contained equal amounts of cells.

Cells produced in Example 1, Example 7, and Example 8 were assayed using this urate consumption assay with results shown in FIG. 4. The graph clearly shows that cells produced as outlined in Example 1 reduced the uric acid concentration in the medium as determined by A293 most rapidly, followed by cells produced as outlined in Example 8, with cells produced as outlined in Example 7 consumed uric acid the slowest.

What is claimed is:

1. An engineered bacterial cell, the cell comprising:

a first nucleic acid encoding an intracellular uric acid degrading polypeptide operatively linked to a constitutive heterologous promoter; and a second nucleic acid encoding a uric acid transporter operatively linked to a heterologous promoter, wherein the uric acid transporter transports uric acid into the engineered bacterial cell;

wherein the engineered bacterial cell has increased intracellular uric acid degrading activity and has increased uric acid uptake activity as compared to an otherwise identical non-engineered bacterial cell that does not comprise the first and second nucleic acids.

2. The engineered bacterial cell of claim 1, wherein the uric acid transporter comprises an amino acid sequence having at least 95% sequence identity with the full length amino acid sequence of any one of SEQ ID NOs: 9-17.

3. The engineered bacterial cell of claim 1, wherein the uric acid degrading polypeptide is a uricase.

4. The engineered bacterial cell of claim 3, wherein the uricase is a fungal uricase.

5. The engineered bacterial cell of claim 3, wherein the uricase comprises an amino acid sequence having at least 95% sequence identity to the full length amino acid sequence of one of SEQ ID NOs: 1-7.

6. The engineered bacterial cell of claim 3, wherein the uricase is a bacterial uricase.

7. A method of lowering uric acid in a gastrointestinal tract of a recipient, the method comprising:

administering to the gastrointestinal tract of the recipient the engineered bacterial cell of claim 1.

8. The method of claim 7, wherein the recipient suffers from a condition selected from the group consisting of: gout, rheumatoid arthritis, cerebral stroke, heart disease, arrhythmia, chronic renal disease, and chronic refractory gout.

9. The method of claim 7, wherein the recipient suffers from chronic refractory gout.

10. The method of claim 7, wherein the engineered bacterial cell is administered to the gastrointestinal tract of the recipient by oral administration.

11. The method of claim 7, wherein the recipient is administered $10^6$ to $10^{12}$ of the engineered bacterial cells.

12. The method of claim 7, further comprising determining that the recipient has a serum uric acid level of ≥6.8 mg/dl prior to administration.

13. The engineered bacterial cell of claim 1, wherein the first and second nucleic acids are integrated into the chromosome of the engineered bacterial cell.

14. The engineered bacterial cell of claim 1, wherein the uric acid degrading polypeptide and the uric acid transporter encoded by the first and second nucleic acids are endogenous to the engineered bacterial cell.

15. The engineered bacterial cell of claim 1, wherein the first and second nucleic acids are located in a single operon wherein mRNA transcribed from the first and second nucleic acids is independently translated to produce distinct protein products.

* * * * *